(12) United States Patent
Sondek et al.

(10) Patent No.: US 9,540,620 B2
(45) Date of Patent: Jan. 10, 2017

(54) METHODS AND COMPOSITIONS FOR MODULATING G-ALPHA-Q SIGNALING

(71) Applicant: The University of North Carolina at Chapel Hill, Chapel Hill, NC (US)

(72) Inventors: John Sondek, Chapel Hill, NC (US); Thomas Kendall Harden, Westfield, NC (US); Gary Lynn Waldo, Chapel Hill, NC (US); Matthew Owen Barrett, Carrboro, NC (US); Thomas Henry Charpentier, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/398,678

(22) PCT Filed: Mar. 8, 2013

(86) PCT No.: PCT/US2013/029920
§ 371 (c)(1),
(2) Date: Nov. 3, 2014

(87) PCT Pub. No.: WO2013/165554
PCT Pub. Date: Nov. 7, 2013

(65) Prior Publication Data
US 2015/0218538 A1    Aug. 6, 2015

Related U.S. Application Data

(60) Provisional application No. 61/643,670, filed on May 7, 2012, provisional application No. 61/642,368, filed on May 3, 2012.

(51) Int. Cl.
| | | |
|---|---|---|
| *A61K 38/00* | (2006.01) | |
| *C12N 9/16* | (2006.01) | |
| *A61K 38/46* | (2006.01) | |
| *C07K 14/47* | (2006.01) | |
| *A61K 47/48* | (2006.01) | |
| *C12Q 1/34* | (2006.01) | |

(52) U.S. Cl.
CPC ............... *C12N 9/16* (2013.01); *A61K 38/465* (2013.01); *A61K 47/48046* (2013.01); *A61K 47/48246* (2013.01); *C07K 14/4703* (2013.01); *C12Q 1/34* (2013.01); *C12Y 301/04011* (2013.01); *G01N 2333/914* (2013.01); *G01N 2500/02* (2013.01); *G01N 2500/04* (2013.01); *G01N 2500/20* (2013.01)

(58) Field of Classification Search
None
See application file for complete search history.

(56) References Cited

U.S. PATENT DOCUMENTS

| | | |
|---|---|---|
| 5,726,025 A | 3/1998 | Kirschner et al. |
| 5,972,621 A | 10/1999 | Tartaglia et al. |
| 5,985,829 A | 11/1999 | Harris et al. |
| 6,015,692 A | 1/2000 | Gyuris et al. |
| 7,807,400 B2 | 10/2010 | Sondek et al. |
| 2004/0053821 A1 | 3/2004 | Mosberg |
| 2011/0070221 A1 | 3/2011 | Bastian et al. |

FOREIGN PATENT DOCUMENTS

| | | |
|---|---|---|
| WO | WO 02/072778 A2 | 9/2002 |
| WO | WO 2004/009770 A2 | 1/2004 |

OTHER PUBLICATIONS

Xiao et al, Tumor Suppression by Phospholipase C-b3 via SHP-1-Mediated Dephosphorylation of Stat5 (Cancer Cell 16, 161-171, Aug. 4, 2009).*
Jhon et al, Cloning, Sequencing, Purification, and Gq-dependent Activation of Phospholipase C-,b3 (J Biol Chem, Mar. 25, 1993;268(9):6654-61).*
Schartl et al, A Mutated EGFR Is Sufficient to Induce Malignant Melanoma with Genetic Background-Dependent Histopathologies (Journal of Investigative Dermatology (2010) 130, 249-258).*
Ross, Gaq and Phospholipase C-b3: Turn on, Turn Off, and Do It Fast (Sci Signal., Feb. 8, 2011;4(159):pe5).*
Augustine et al. "Sorafenib, a Multikinase Inhibitor, Enhances the Response of Melanoma to Regional Chemotherapy" *Molecular Cancer Therapeutics* 9(7):2090-2101 (2010).
Bembenek et al. "Development of a High-Throughput Assay for Two Inositol-Specific Phospholipase Cs Using a Scintillation Proximity Format" *Assay and Drug Development Technologies* 1(3):435-443 (2003).
Bemis et al. "The Properties of Known Drugs. 1. Molecular Frameworks" *Journal of Medical Chemistry* 39:2887-2893 (1996).
Bernal et al. "Reactivation of the p53 Tumor Suppressor Pathway by a Stapled p53 Peptide" *Journal of the American Chemical Society* 129:2456-2457 (2007).
Bird et al. "Hydrocarbon double-stapling remedies the proteolytic instability of a lengthy peptide therapeutic" *Proceedings of the National Academy of Sciences* 107(32):14093-14098 (2010).
Blackwell et al. "Ring-Closing Metathesis of Olefinic Peptides: Design, Synthesis, and Structural Characterization of Macrocyclic Helical Peptides" *The Journal of Organic Chemistry* 66:5291-5302 (2001).
Bower et al. "Topoisomerase IIα maintains genomic stability through decatenation $G_2$ checkpoint signaling" *Oncogene* 29(34):4787-4799 (2010).
Ellis et al. "Catalytic Domain of Phosphoinositide-specific Phospholipase C (PLC): Mutational Analysis of Residues Within the Active Site and Hydrophobic Ridge of PLCδ1" *The Journal of Biological Chemistry* 273(19):11650-11659 (1998).

(Continued)

*Primary Examiner* — Karlheinz R Skowronek
*Assistant Examiner* — Sergio Coffa
(74) *Attorney, Agent, or Firm* — Myers Bigel, P.A.

(57) ABSTRACT

The present invention provides compositions and methods for modulating G-alpha-q activity and methods of screening of test substances for the ability to modulate G-alpha-q activity.

17 Claims, 10 Drawing Sheets

(56) References Cited

OTHER PUBLICATIONS

Fritz et al. "Rho GTPases Are Over-Expressed in Human Tumors" *International Journal of Cancer* 81:682-687 (1999).
Haluska et al. "Therapeutic Targets in Melanoma. MAPKinase Pathway" *Current Oncology Reports* 8:400-405 (2006).
Hawes et al. "Distinct Pathways of $G_i$- and $G_q$-mediated Mitogen-activated Protein Kinase Activation" *The Journal of Biological Chemistry* 270(29):17148-17153 (1995).
Hicks et al. "General and Versatile Autoinhibition of PLC Isozymes" *Molecular Cell* 31:383-394 (2008).
Inamdar et al. "Targeting the MAPK Pathway in Melanoma: Why some approaches succeed and other fail" *Biochemical Pharmacology* 80(5):624-637 (2010).
International Preliminary Report on Patentability corresponding to International Patent Application No. PCT/US2013/029920:9 pages (mailed Nov. 13, 2014).
Jacobsen et al. "Structural and Pharmacological Effects of Ring-Closing Metathesis in Peptides" *Molecules* 15:6638-6677 (2010).
Kimple et al. "A High-Throughput Fluorescence Polarization Assay for Inhibitors of the GoLoco Motif/G-alpha Interaction" *Combinatorial Chemistry & High Throughput Screening* 11(5):396-409 (2008).
Küsters-Vandevelde et al. "Activating mutations of the *GNAQ* gene: a frequent event in primary melanocytic neoplasms of the central nervous system" *Acta Neuropathologica* 119:317-323 (2010).
Lambright et al. "The 2.0 Å crystal structure of a heterotrimeric G protein" *Nature* 379:311-319 (1996).
Lutz et al. "The Guanine Nucleotide Exchange Factor p63RhoGEF, a Specific Link between $G_{q/11}$-coupled Receptor Signaling and RhoA" *The Journal of Biological Chemistry* 280(12):11134-11139 (2005).
Lutz et al. "Structure of $G\alpha_q$-p63RhoGEF-RhoA Complex Reveals a Pathway for the Activation of RhoA by GPCRs" *Science* 318:1923-1927 (2007).
Lyon et al. "An Autoinhibitory Helix in the C-Terminal Region of Phospholipase C-β Mediates $G\alpha_q$ Activation" *Nature Structural & Molecular Biology* 18(9):999-1005 (2012).
Miller et al. "Synthesis of Conformationally Restricted Amino Acids and Peptides Employing Olefin Metathesis" *Journal of the American Chemical Society* 117:5855-5856 (1995).
Moellering et al. "Direct inhibition of the NOTCH transcription factor complex" *Nature* 462:182-190 (2009).
Owicki, John C. "Fluorescence Polarization and Anisotropy in High Throughput Screening: Perspectives and Primer" *Journal of Biomolecular Screening* 5(5):297-306 (2000).
Rojas et al. "$G\alpha_q$ Directly Activates p63RhoGEF and Trio via a Conserved Extension of the Dbl Homology-associated Pleckstrin Homology Domain" *The Journal of Biological Chemistry* 282(40):29201-29210 (2007).
Romano et al. "Treatment implications of the emerging molecular classification system for melanoma" *The Lancet Oncology* 12:913-922 (2011).
Sah et al. "Rho Is Required for $G\alpha_q$ and $\alpha_1$-Adrenergic Receptor Signaling in Cardiomyocytes: Dissociation of Ras and Rho Pathways" *The Journal of Biological Chemistry* 271(49):31185-31190 (1996).
Saldanha et al. "High *BRAF* Mutation Frequency Does Not Characterize All Melanocytic Tumor Types" *International Journal of Cancer* 111:705-710 (2004).
Seo et al. "*Pasteurella multocida* Toxin Stimulates Mitogen-activated Protein Kinase via $G_{q/11}$-dependent Transactivation of the Epidermal Growth Factor Receptor" *The Journal of Biological Chemistry* 275(3):2239-2245 (2000).
Shields et al. "Lack of Extracellular Signal-Regulated Kinase Mitogen-Activated Protein Kinase Signaling Shows a New Type of Melanoma" *Cancer Research* 67(4):1502-1512 (2007).
Sjöblom et al. "The Consensus Coding Sequences of Human Breast and Colorectal Cancers" *Science* 314:268-273 (2006).
Slep et al. "Structural determinants for regulation of phosphodiesterase by a G protein at 2.0 Å" *Nature* 409:1071-1077 (2001).
Stennicke et al. "Catalytic properties of the caspases" *Cell Death and Differentiation* 6:1054-1059 (1999).
Tesmer et al. "Two-Metal-Ion Catalysis in Adenylyl Cyclase" *Science* 285:756-760 (1999).
Tesmer et al. "Snapshot of Activated G Proteins at the Membrane: The $G\alpha_q$-GRK2-Gβγ Complex" *Science* 310:1686-1690 (2005).
Van Raamsdonk et al. "Frequent somatic mutations of *GNAQ* in uveal melanoma and blue naevi" *Nature* 457:599-603 (2009).
Van Raamsdonk et al. "Mutations in *GNA11* in Uveal Melanoma" *The New England Journal of Medicine* 363(23):2191-2199 (2010).
Waldo et al. "Kinetic Scaffolding Mediated by a Phospholipase C-β and $G_q$ Signaling Complex" *Science* 330(6006):974-980 (2010).
Wei et al. "Exome sequencing identifies GRIN2A as frequently mutated in melanoma" *Nature Genetics* 43(5):442-448 (2011).
Whitehurst et al. "Synthetic lethal screen identification of chemosensitizer loci in cancer cells" *Nature* 446:815-819 (2007).
Zhang et al. "A Simple Statistical Parameter for Use in Evaluation and Validation of High Throughput Screening Assays" *Journal of Biomolecular Screening* 4(2):67-73 (1999).
Zuidervaart et al. "Activation of the MAPK pathway is a common event in uveal melanomas although it rarely occurs through mutation of *BRAF* or *RAS*" *British Journal of Cancer* 92:2032-2038 (2005).
Bedikian, Agop Y. "Metastic Uveal Melanoma Therapy: Current Options" *International Ophthalmology Clinics* 46(1):151-166 (2006).
Begley, David J. "The Blood-brain Barrier: Principles for Targeting Peptides and Drugs to the Central Nervous System" *Journal of Pharmacology and Pharmacotherapeutics* 48:136-146 (1996).
Bourdon et al. "Quantification of Isozyme-Specific Activation of Phospholipase C-β2 by Rac GTPases and Phospholipase C-ϵ by Rho GTPases in an Intact cell Assay System" *Methods in Enzymology* 406:489-499 (2006).
Cao et al. "In Vivo Delivery of a Bcl-xL Fusion Protein Containing the TAT Protein Transduction Domain Protects against Ischemic Brain Injury and Neuronal Apoptosis" *The Journal of Neuroscience* 22(13):5423-5431 (2002).
Chen et al. "Molecular transporters for peptides: delivery of a cardioprotective ϵPKC agonist peptide into cells and intact ischemic heart using a transport system, $R_7$" *Chemistry & Biology* 8:1123-1129 (2001).
Derer et al. "A novel approach to induce cell cycle reentry in terminally differentiated muscle cells" *The FASEB Journal* 16:12 pages (2001).
Derossi et al. "Cell Internalization of the Third Helix of the Antennapedia Homeodomain Is Receptor-independent" *The Journal of Biological Chemistry* 271(30):18188-18193 (1996).
Egan et al. "Epidemiologic Aspects of Uveal Melanoma" *Survey of Ophthalmology* 32(4):239-251 (1988).
Elliott et al. "Intercellular Trafficking and Protein Delivery by a Herpesvirus Structural Protein" *Cell* 88:223-233 (997).
Fawell et al. "Tat-mediated delivery of heterologous proteins into cells" *Proceedings of the National Academy of Sciences* 91:664-668 (1994).
Fecher et al. "The MAPK pathway in melanoma" *Current Opinion in Oncology* 20:183-189 (2008).
Frankel et al. "Cellular Uptake of the Tat Protein from Human Immunodeficiency Virus" *Cell* 55:1189-1193 (1988).
Green et al. "Autonomous Functional Domains of Chemically Synthesized Human Immunodeficiency Virus Tat *Trans*-Activator Protein" *Cell* 55:1179-1188 (1988).
Gustafsson et al. "TAT Protein Transduction Into Isolated Perfused Hearts: TAT-Apoptosis Repressor With Caspase Recruitment Domain Is Cardioprotective" *Circulation* 106:735-739 (2002).
Ho et al. "Synthetic Protein Transduction Domains: Enhanced Transduction Potential in Vitro and in Vivo" *Cancer Research* 61:474-477 (2001).
Morris et al. "A peptide carrier for the delivery of biologically active proteins into mammalian cells" *Nature Biotechnology* 19:1173-1176 (2001).

(56) References Cited

OTHER PUBLICATIONS

Nagahara et al. "Transduction of full-length TAT fusion proteins into mammalian cells: TAT-p27$^{Kip1}$ induces cell migration" *Nature Medicine* 4(12):1449-1452 (1998).

Nicholas et al. "Pharmacological and second messenger signalling selectivities of cloned P2Y receptors" *Journal of Autonomic Pharmacology* 16:319-323 (1996).

Pietersz et al. "A16-mer peptide (RQIKIWFQNRRMKWKK) from antennapedia preferentially targets the Class I pathway" *Vaccine* 19(11-12):1397-1405 (2001) (Abstract Only).

Pooga et al. "Cell penetration by transportan" *The FASEB Journal* 12:67-77 (1998).

Populo et al. "Analysis of GNAQ mutations, proliferation and MAPK pathway activation in uveal melanomas" *British Journal of Ophthalmology* 95:715-719 (2011).

Rathinam et al. "Role of Rho GTPases and their regulators in cancer progression" *Frontiers in Bioscience (Landmark Edition)* 16:2561-2571 (2011) (Abstract Only).

Rothbard et al. "Arginine-Rich Molecular Transporters for Drug Delivery: Role of Backbone Spacing in Cellular Uptake" *Journal of Medicinal Chemistry* 45:3612-3618 (2002).

Schwarze et al. "In Vivo Protein Transduction: Delivery of a Biologically Active Protein into the Mouse" *Science* 285:1569-1572 (1999).

Schwarze et al. "In Vivo protein transduction: intracellular delivery of biologically active proteins, compounds and DNA" *Trends in Pharmacological Sciences* 21:45-48 (2000).

Service, Robert F. "Chemical Tags Speed Delivery Into Cells" *Science* 288(5463):28-29 (2000).

Shields et al. "Ocular melanoma: relatively rare but requiring respect" *Clinics in Dermatology* 27:122-133 (2009).

Singh et al. "Genetic aspects of uveal melanoma: a brief review" *Seminars in Oncology* 23(6):768-772 (1996) (Abstract Only).

Singh et al. "Survival Rates with Uveal Melanoma in the United States: 1973-1997" *Ophthalmology* 110(5):962-965 (2003).

Singh et al. "Uveal melanoma: epidemiologic aspects" *Ophthalmology Clinics of North America* 18(1):75-84 (2005) (Abstract Only).

Tan et al. "Stereoselective Synthesis of over Two Million Compounds Having Structural Features Both Reminiscent of Natural Products and Compatible with Miniaturized Cell-Based Assays" *Journal of the American Chemical Society* 120:8565-8566 (1998).

Thomas, Nancy E. "*BRAF* somatic mutations in malignant melanoma and melanocytic naevi" *Melanoma Research* 16:97-103 (2006).

Triozzi et al. "Targeted therapy for uveal melanoma" *Cancer Treatment Reviews* 34:247-258 (2008).

Wender et al. "The design, synthesis, and evaluation of molecules that enable or enhance cellular uptake: Peptoid molecular transporters" *Proceedings of the National Academy of Sciences* 97(24):13003-13008 (2000).

Will et al. "Unmodified Cre recombinase crosses the membrane" *Nucleic Acids Research* 30(12):e59 (2002).

Singer et al. "A unique fold of phospholipase C-β mediates dimerization and interaction with G alpha q" *Nature Structural Biology* 9(1):32-36 (2002).

Sondek et al. "GTPase mechanism of G proteins from the 1.7-Å crystal structure of transducin alpha-GDP-AIF$_4$" *Nature* 372:276-279 (1994).

International Search Report Corresponding to International Application No. PCT/US2013/029920; Date of Mailing: Jun. 21, 2013 (3 pages).

\* cited by examiner

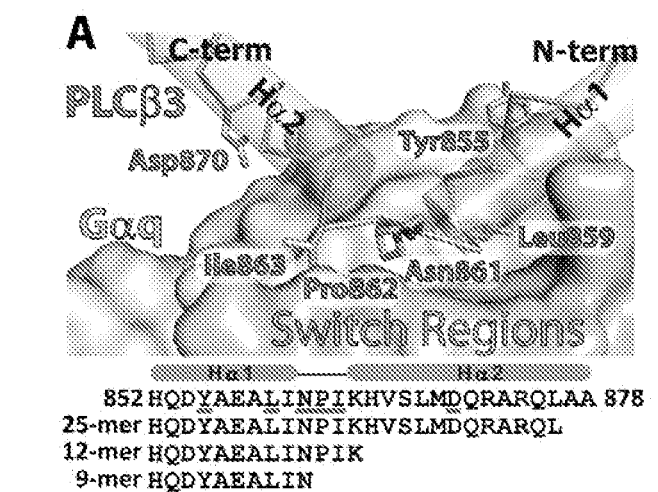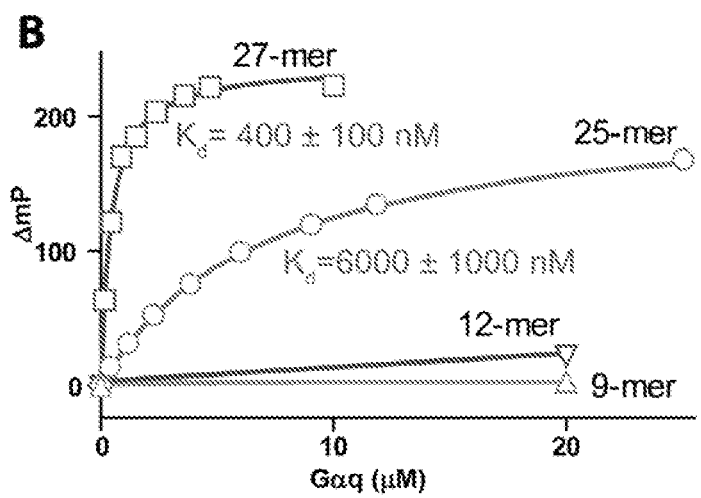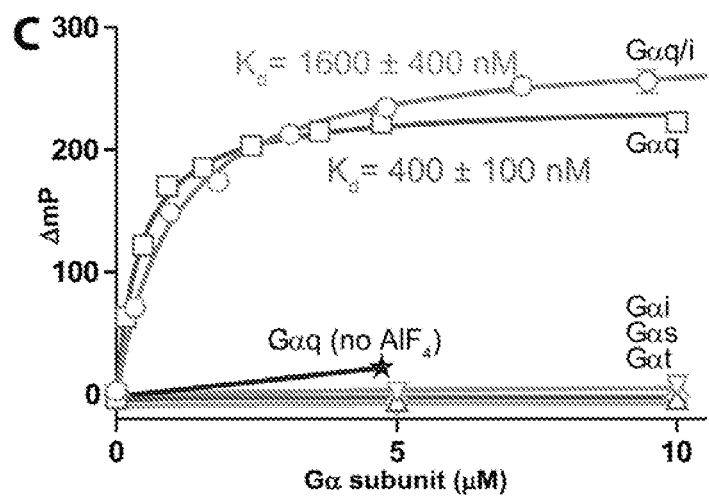
FIGS. 2A–C

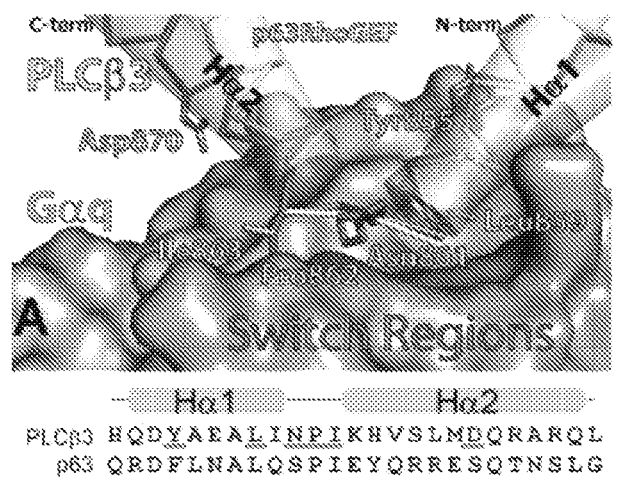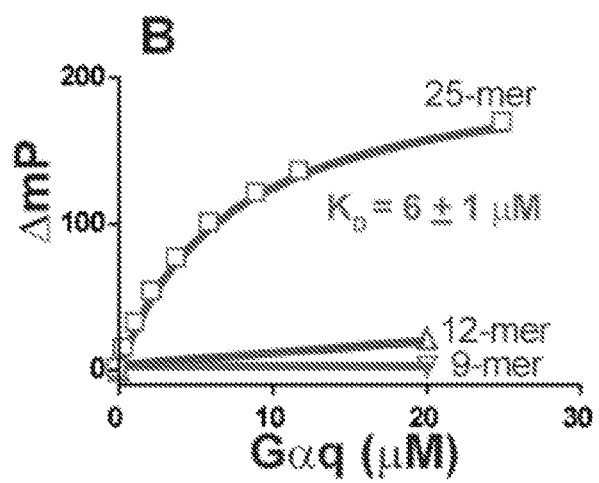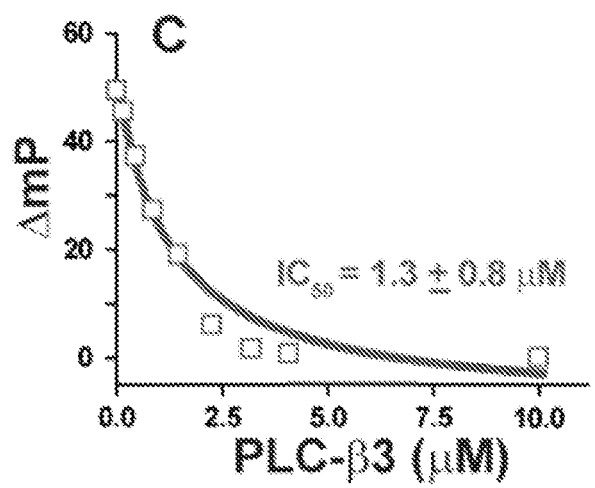
FIGS. 6A–C

Palmitoylated peptide inhibits endogenous PLCs downstream of Gαq

27mer without palmitoyl group produces no inhibition

HEK-293 cells; 10 min Pal-27mer; 30 min carbachol

METHODS AND COMPOSITIONS FOR MODULATING G-ALPHA-Q SIGNALING

STATEMENT OF PRIORITY

This application is a 35 USC § 371 national phase application of International Application Serial No. PCT/US2013/029920, filed Mar. 8, 2013, which claims the benefit under 35 U.S.C. § 119(e), of U.S. Provisional Application Ser. No. 61/642,368, filed May 3, 2012 and U.S. Provisional Application Ser. No. 61/643,670, filed May 7, 2012, the entire contents of each of which are incorporated by reference herein.

STATEMENT OF GOVERNMENT SUPPORT

This invention was made with government support under Grant Nos. GM057391, GM081881 and GM098894 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-630TS_ST25.txt, 18,503 bytes in size, generated on Mar. 16, 2015 and filed via EFS-Web, is provided in lieu of a paper copy. The Sequence Listing is incorporated herein by reference into the specification for its disclosures.

FIELD OF INVENTION

The present invention relates to compositions and methods for inhibiting G-alpha-q signaling, e.g., to treat disorders associated with G-alpha-q mutation, such as uveal melanoma.

BACKGROUND OF THE INVENTION

Uveal melanoma is the major intraocular cancer, with 1,500 new cases in North America per year and a 50% chance of metastasizing to the liver[1,2]. The majority of uveal melanomas contain mutated Gαq that is constitutively active leading to aberrant activation of the Mitogen-Activated Protein Kinase (MAPK) pathway and concomitant tumor progression[3,4]. Gαq directly activates the phospholipase C beta isoforms (PLC-β1-4) leading to the hydrolysis of phosphatidylinositol 4,5-bisphosphate ($PIP_2$) into the second messengers, inositol trisphosphate ($IP_3$) and diacylglycerol (DAG). These second messengers mobilize intracellular calcium stores and activate protein kinase C (PKC) to promote proliferation[5,6]. Gαq also directly activates p63RhoGEF and related guanine nucleotide exchange factors that subsequently activate the low-molecular weight GTPase, RhoA, and possibly other, related GTPases[7,8]. Excessive activation of RhoA and related GTPases has also been shown to contribute to cancer progression[9,10].

Melanomas are categorized into distinct subtypes—uveal, cutaneous, and acral—based on multiple criteria, including: cell morphology, gene expression patterns, metastatic potential, chemoresistance, and overall treatment regimens[7,8]. In contrast to uveal melanomas, cutaneous melanomas are most often driven by constitutively active N-Ras or B-Raf leading to the activation of the MAPK cascade[9,10]. Constitutively active Gαq is rare in cutaneous melanomas but is often found in benign blue nevi derived from cutaneous melanocytes, indicating that Gαq activates MAPK signaling in these melanocytes also[3,4].

The present invention overcomes previous shortcomings in the art by providing methods and compositions for modulating the signaling activity of G-alpha-q, e.g., to treat disorders associated with aberrant signaling of G-alpha-q.

SUMMARY OF THE INVENTION

In one aspect, the present invention provides a method of downregulating G-alpha-Q signaling in a cell, comprising introducing into the cell a peptide comprising the amino acid sequence of Formula I shown below.

In further aspects, the present invention provides a method of treating a disorder, e.g., a cancer associated with a Gαq mutation in a subject in need thereof, comprising introducing to the subject an effective amount of a peptide comprising the amino acid sequence of Formula I shown below.

Formula I:

$X_1 X_2 X_3 X_4 X_5 X_6 X_7 X_8 X_9 X_{10} X_{11} X_{12} X_{13} X_{14} X_{15} X_{16} X_{17} X_{18} X_{19} X_{20} X_{21}$ (SEQ ID NO:1), wherein $X_1$ is H;

$X_2$ is Q or any nonnatural amino acid (e.g., as listed in Table 1) or any amino acid listed in Table 2;

$X_3$ is D or any nonnatural amino acid (e.g., as listed in Table 1) or any amino acid listed in Table 2;

$X_4$ is Y;

$X_5$ is A;

$X_6$ is E or any nonnatural amino acid (e.g., as listed in Table 1) or any amino acid listed in Table 2;

$X_7$ is A;

X8 is L or any nonnatural amino acid (e.g., as listed in Table 1);

$X_9$ is I or A or Y or N; or any nonnatural amino acid (e.g., as listed in Table 1) or any amino acid listed in Table 2;

$X_{10}$ is N;

$X_{11}$ is P;

$X_{12}$ is I;

$X_{13}$ is K or any nonnatural amino acid (e.g., as listed in Table 1) or any amino acid listed in Table 2;

$X_{14}$ is H;

$X_{15}$ is V;

$X_{16}$ is S;

$X_{17}$ is L or any nonnatural amino acid (e.g., as listed in Table 1) or any amino acid listed in Table 2;

$X_{18}$ is M or norleucine or any other nonnatural amino acid (e.g., as listed in Table 1);

$X_{19}$ is D;

$X_{20}$ is Q; and $X_{21}$ is R.

In further embodiments, the peptide of Formula I can further comprise from one to six additional amino acids, $X_{22}$, $X_{23}$, $X_{24}$, $X_{25}$, $X_{26}$ and $X_{27}$, wherein $X_{22}$ is A or any nonnatural amino acid (e.g., as listed in Table 1) or any amino acid listed in Table 2;

$X_{23}$ is R or any nonnatural amino acid (e.g., as listed in Table 1) or any amino acid listed in Table 2;

$X_{24}$ is Q or any nonnatural amino acid (e.g., as listed in Table 1) or any amino acid listed in Table 2;

$X_{25}$ is L or any nonnatural amino acid (e.g., as listed in Table 1) or any amino acid listed in Table 2;

$X_{26}$ is A or any nonnatural amino acid (e.g., as listed in Table 1) or any amino acid listed in Table 2; and $X_{27}$ is A or any nonnatural amino acid (e.g., as listed in Table 1) or any amino acid listed in Table 2.

In further aspects, the present invention provides a method of identifying a test substance having the ability to inhibit G-alpha-q activity, comprising: a) contacting a TAMRA-27-mer peptide with G-alpha-q and GDP and aluminum fluoride and determining a baseline fluorescence polarization value; and b) contacting a TAMRA-27-mer peptide with G-alpha-q, GDP, aluminum fluoride and the test substance and determining a fluorescence polarization value, wherein a fluorescence polarization value of (b) that is lower than the fluorescence polarization value of (a) identifies the test substance as having the ability to inhibit G-alpha-q activity.

Additionally provided herein is a method of identifying a test substance having the ability to increase G-alpha-q activity, comprising: a) contacting a TAMRA-27-mer peptide with G-alpha-q, GDP and aluminum fluoride and determining a baseline fluorescence polarization value and; b) contacting a TAMRA-27-mer peptide with G-alpha-q, GDP, aluminum fluoride and the test substance and determining a fluorescence polarization value, wherein a fluorescence polarization value of (b) that is greater than the fluorescence polarization value of (a) identifies the test substance as having the ability to increase G-alpha-q activity.

BRIEF DESCRIPTION OF THE DRAWINGS

FIGS. 2A-C. Peptides derived from PLC-β3 bind with high affinity and selectivity to activated Gαq. (FIG. 2A) The effector binding pocket of Gαq (green; with switch regions in red) bound to a helix-turn-helix portion of PLC-β3 (blue; PDB: 3OHM). Sequence of the helix-turn-helix is shown; underlined residues are labeled in the structure and a subset of synthetic peptides tested for binding to Gαq are listed (SEQ ID NOS: 37-40). (FIG. 2B) Gαq activated with aluminum fluoride was titrated into solutions of peptides labeled with TAMRA (5-carboxytetramethylrhodamine) and complex formation was measured by fluorescence polarization (ΔmP; change in milliPolarization). (FIG. 2C) TAMRA-27-mer was tested for complex formation with the indicated forms of Gα subunits.

(FIG. 3A) Increasing concentrations of PLC-β3 were added to a solution of TAMRA-27-mer (400 nM) and Gαq (800 nM). The $IC_{50}$ value is derived from three independent experiments. (FIG. 3B) Phospholipase activity of PLC-β3 activated by Gαq using lipid vesicles and inhibited by increasing concentrations of TAMRA-27-mer.

FIGS. 6A-C. Quantification of Gαq binding to peptides corresponding to the HTH of PLβ3. (FIG. 6A) The effector binding surface of Gαq (green; with switch regions in red) highlights a common mode of engagement by PLCβ3 (blue) and p63RhoGEF (yellow). The structures of PLCβ3 (3 OHM) and p63RhoGEF (2RGN) bound to Gαq were superimposed and a single Gαq is shown. Immediately below is shown the sequence alignment of PLCβ3 (SEQ ID NO:37) and p63RhoGEF (SEQ ID NO:41) encompassing the helix-turn-helix. Underlined residues are labeled in the structure. (FIG. 6B) Gαq activated with aluminum fluoride was titrated into solutions of peptides (25-mer is equivalent to sequence in (FIG. 6A)) labeled with TAMRA (5-carboxytetramethylrhodamine), and complex formation was measured by fluorescence polarization (ΔmP; change in milliPolarization). (FIG. 6C) Increasing concentrations of unlabeled PLC-β3 were added to a solution of labeled 25-mer (400 nM) and Gαq (4 μM). $K_D$ and $IC_{50}$ values were derived from three independent experiments.

(FIG. 7A) Gαq (60 nM) and PLC-β3-dependent [$^3$H]inositol phosphate accumulation is inhibited by varying amounts of TAMRA-27-mer in vesicles. (FIG. 7B) Confocal image (left) and Z-stack (right) of live 1321N1 cells expressing P2Y6 receptor and loaded with TAMRA-TAT-27-mer. The TAT sequence is an HIV derived peptide that specifically facilitates cellular uptake. (C) P2Y6 receptor-dependent activation of PLC-β was determined by quantification of [$^3$H]inositol phosphate accumulation. Where indicated, 1321N1 cells were treated with TAMRA-TAT-27-mer peptide for an hour.

DETAILED DESCRIPTION OF THE INVENTION

Figure 1:
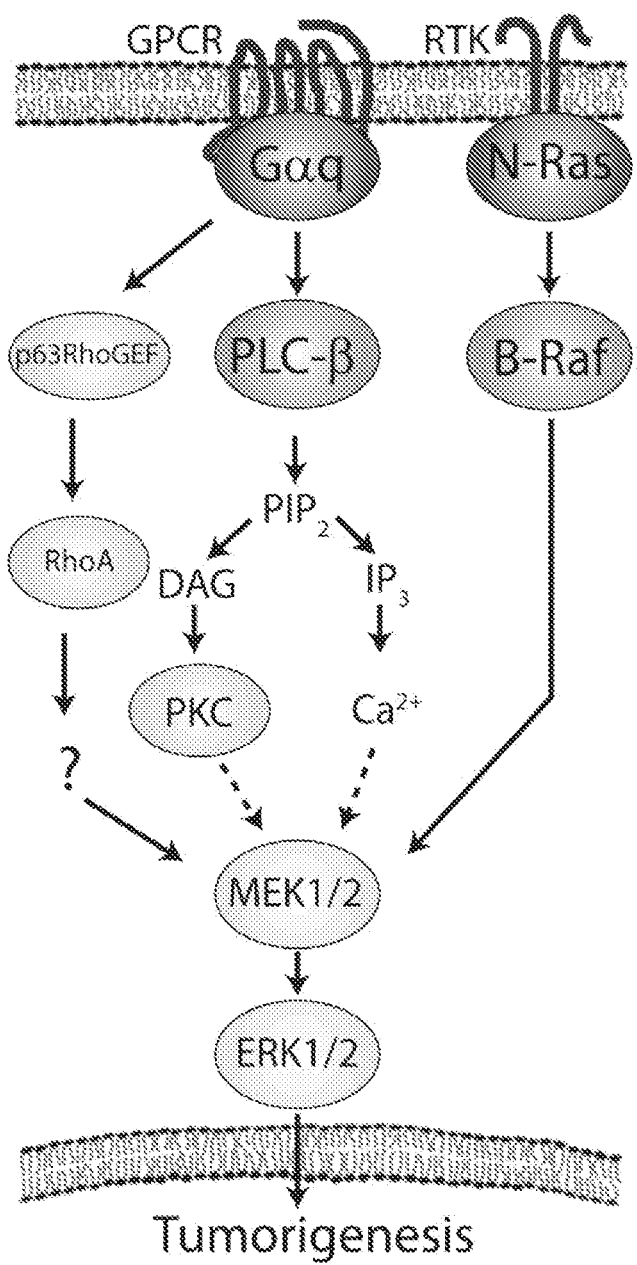
FIG. 1. Signaling cascades controlled by Gαq and N-Ras drive tumorigenesis through the MAPK pathway. PLC-β isoforms hydrolyze phosphatidylinositol 4,5-bisphosphate ($PIP_2$) to inositol trisphosphate ($IP_3$) and diacylglycerol (DAG) leading to elevated calcium and protein kinase C (PKC) activation. Both inputs indirectly activate (dash lines) the MAPK pathway (RAF/MEK/ERK).

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Also as used herein, "and/or" refers to and encompasses any and all possible combinations of one or more of the associated listed items, as well as the lack of combinations when interpreted in the alternative ("or").

As used herein, the transitional phrase "consisting essentially of" (and grammatical variants) is to be interpreted as encompassing the recited materials or steps "and those that do not materially affect the basic and novel characteristic(s)"

of the claimed invention. Thus, the term "consisting essentially of" as used herein should not be interpreted as equivalent to "comprising."

The present invention is described in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

In one embodiment, the present invention provides a method of downregulating G-alpha-Q signaling in a cell, comprising introducing into the cell a peptide comprising the amino acid sequence of Formula I:

$$X_1 X_2 X_3 X_4 X_5 X_6 X_7 X_8 X_9 X_{10} X_{11} X_{12} X_{13} X_{14} X_{15} X_{16} X_{17} X_{18} X_{19} X_{20} X_{21} \text{ (SEQ ID NO:1)},$$
wherein $X_1$ is H;
$X_2$ is Q or any nonnatural amino acid (e.g., as listed in Table 1) or any amino acid listed in Table 2;
$X_3$ is D or any nonnatural amino acid (e.g., as listed in Table 1) or any amino acid listed in Table 2;
$X_4$ is Y;
$X_5$ is A;
$X_6$ is E or any nonnatural amino acid (e.g., as listed in Table 1) or any amino acid listed in Table 2;
$X_7$ is A;
$X_8$ is L or any nonnatural amino acid (e.g., as listed in Table 1).
$X_9$ is I or A or Y or N, or any nonnatural amino acid (e.g., as listed in Table 1) or any amino acid listed in Table 2;
$X_{10}$ is N;
$X_{11}$ is P;
$X_{12}$ is I;
$X_{13}$ is K or any nonnatural amino acid (e.g., as listed in Table 1) or any amino acid listed in Table 2;
$X_{14}$ is H;
$X_{15}$ is V;
$X_{16}$ is S;
$X_{17}$ is L or any nonnatural amino acid (e.g., as listed in Table 1) or any amino acid listed in Table 2;
$X_{18}$ is M or norleucine or any other nonnatural amino acid (e.g., as listed in Table 1);
$X_{19}$ is D;
$X_{20}$ is Q; and
$X_{21}$ is R.

In further embodiments of the method described above, the peptide of Formula I can further comprise from one to six additional amino acids, $X_{22}$, $X_{23}$, $X_{24}$, $X_{25}$, $X_{26}$ and $X_{27}$, wherein $X_{22}$ is A or any nonnatural amino acid (e.g., as listed in Table 1) or any amino acid listed in Table 2;
$X_{23}$ is R or any nonnatural amino acid (e.g., as listed in Table 1) or any amino acid listed in Table 2;
$X_{24}$ is Q or any nonnatural amino acid (e.g., as listed in Table 1) or any amino acid listed in Table 2;
$X_{25}$ is L or any nonnatural amino acid (e.g., as listed in Table 1) or any amino acid listed in Table 2;
$X_{26}$ is A or any nonnatural amino acid (e.g., as listed in Table 1) or any amino acid listed in Table 2; and
$X_{27}$ is A or any nonnatural amino acid (e.g., as listed in Table 1) or any amino acid listed in Table 2.

Also provided herein is method of treating a disorder associated with a Gαq mutation (e.g. a cancer such as uveal melanoma) in a subject in need thereof, comprising introducing to the subject an effective amount of a peptide comprising the amino acid sequence of Formula I:

$$X_1 X_2 X_3 X_4 X_5 X_6 X_7 X_8 X_9 X_{10} X_{11} X_{12} X_{13} X_{14} X_{15} X_{16} X_{17} X_{18} X_{19} X_{20} X_{21} \text{ (SEQ ID NO:1)},$$
wherein $X_1$ is H;
$X_2$ is Q or any nonnatural amino acid (e.g., as listed in Table 1) or any amino acid listed in Table 2;
$X_3$ is D or any nonnatural amino acid (e.g., as listed in Table 1) or any amino acid listed in Table 2;
$X_4$ is Y;
$X_5$ is A;
$X_6$ is E or any nonnatural amino acid (e.g., as listed in Table 1) or any amino acid listed in Table 2;
$X_7$ is A;
$X_8$ is L or any nonnatural amino acid (e.g., as listed in Table 1);
$X_9$ is I or A or Y or N, or any nonnatural amino acid (e.g., as listed in Table 1) or any amino acid listed in Table 2;
$X_{10}$ is N;
$X_{11}$ is P;
$X_{12}$ is I;
$X_{13}$ is K or any nonnatural amino acid (e.g., as listed in Table 1) or any amino acid listed in Table 2;
$X_{14}$ is H;
$X_{15}$ is V;
$X_{16}$ is S;
$X_{17}$ is L or any nonnatural amino acid (e.g., as listed in Table 1) or any amino acid listed in Table 2;
$X_{18}$ is M or norleucine or any other nonnatural amino acid (e.g., as listed in Table 1);
$X_{19}$ is D;
$X_{20}$ is Q; and
$X_{21}$ is R.

In further embodiments of the method described above, the peptide of Formula I can further comprise from one to six additional amino acids, $X_{22}$, $X_{23}$, $X_{24}$, $X_{25}$, $X_{26}$ and $X_{27}$, wherein $X_{22}$ is A or any nonnatural amino acid (e.g., as listed in Table 1) or any amino acid listed in Table 2;
$X_{23}$ is R or any nonnatural amino acid (e.g., as listed in Table 1) or any amino acid listed in Table 2;
$X_{24}$ is Q or any nonnatural amino acid (e.g., as listed in Table 1) or any amino acid listed in Table 2;
$X_{25}$ is L or any nonnatural amino acid (e.g., as listed in Table 1) or any amino acid listed in Table 2;

$X_{26}$ is A or any nonnatural amino acid (e.g., as listed in Table 1) or any amino acid listed in Table 2; and $X_{27}$ is A or any nonnatural amino acid (e.g., as listed in Table 1) or any amino acid listed in Table 2.

A disorder associated with a Gαq mutation can be a cancer or neoplasm associated with a Gαq mutation or any other disorder in which Gαq is constitutively expressed. Nonlimiting examples of such disorders include uveal melanoma, melanocytic schwannoma, blue nevus, cutaneous melanoma and any cancer derived from neural crest progenitor cells that contain a mutation in Gαq rendering it constitutively active.

Thus, the present invention provides a peptide that can comprise, consist essentially of or consist of 21 amino acids defined as $X_1$ through $X_{21}$ (i.e., a 21-mer peptide), a peptide that can comprise consist essentially of or consist of 22 amino acids defined as $X_1$ through $X_{22}$ (i.e., a 22-mer peptide), a peptide that can comprise, consist essentially of or consist of 23 amino acids defined as $X_1$ through $X_{23}$ (i.e., a 23-mer peptide), a peptide that can comprise, consist essentially of or consist of 24 amino acids defined as $X_1$ through $X_{24}$ (i.e., a 24-mer peptide), a peptide that can comprise, consist essentially of or consist of 25 amino acids defined as $X_1$ through $X_{25}$ (i.e., a 25-mer peptide), a peptide that can comprise, consist essentially of or consist of 26 amino acids defined as $X_1$ through $X_{26}$ (i.e., a 26-mer peptide) and a peptide that can comprise, consist essentially of or consist of 27 amino acids defined as $X_1$ through $X_{27}$ (i.e., a 27-mer peptide).

Nonlimiting examples of a peptide that can be employed in the methods of this invention include HQDYAEALIN-PIKHVSLMDQR (SEQ ID NO:2); HQDYAEALIN-PIKHVSLMDQRARQLAA (SEQ ID NO:3); HQDYAE-ALANPIKHVSL-Nle-DQRARQLAA (SEQ ID NO:4); HX$_{28}$DYA X$_{28}$ALANPIKHVSL-Nle-DQRARQLAA (SEQ ID NO:5), wherein X$_{28}$ is a nonnatural amino acid listed in Table 1; HQDYAEALANPIKHVSL-Nle-DQ X$_{28}$ARQ X$_{28}$AA (SEQ ID NO:6), wherein X$_{28}$ is a nonnatural amino acid listed in Table 1; HQDYAEALANPI X$_{28}$HVS X$_{28}$-Nle-DQRARQLAA (SEQ ID NO:7), wherein X$_{28}$ is a nonnatural amino acid listed in Table 1; HQDYAEALANPIKHVS X$_{28}$-Nle-DQ X$_{28}$ARQLAA (SEQ ID NO:8), wherein X$_{28}$ is a nonnatural amino acid listed in Table 1; HQDYAE-ALANPI X$_{28}$HVSL-Nle-D X$_{28}$RARQLAA (SEQ ID NO:9), wherein X$_{28}$ is a nonnatural amino acid listed in Table 1; HQ X$_{28}$YAEALANPIKHVS X$_{28}$-Nle-DQRARQLAA (SEQ ID NO:10), wherein X$_{28}$ is a nonnatural amino acid listed in Table 1; HQDYA X$_{28}$ALANPI X$_{28}$HVSL-Nle-DQRAR-QLA (SEQ ID NO:11), wherein X$_{28}$ is a nonnatural amino acid listed in Table 1; HQ X$_{28}$YAEALANPIKHVSL-Nle-DQ X$_{28}$ARQLAA (SEQ ID NO:12), wherein X$_{28}$ is a nonnatural amino acid listed in Table 1; HQDYA X$_{28}$ALANPIKHVSL-Nle-DQ X$_{28}$ARQLAA (SEQ ID NO:13), wherein X$_{28}$ is a nonnatural amino acid listed in Table 1; HQ X$_{28}$YAEALANPI X$_{28}$HVSL-Nle-DQRARQ-LAA (SEQ ID NO:14), wherein X$_{28}$ is a nonnatural amino acid listed in Table 1; and HQDYA X$_{28}$ALANPIKHVS X$_{28}$-Nle-DQRARQLAA (SEQ ID NO:15), wherein X$_{28}$ is a nonnatural amino acid listed in Table 1. In some embodiments, Nle is identified as $X_{29}$.

In some embodiments, the peptide of this invention can comprise amino acids YIPX$_{28}$D (SEQ ID NO:16) at the amino terminus. A nonlimiting example of such a peptide is YIP X$_{28}$DHQDYA X$_{28}$ALANPIKHVSLMDQRARALAA (SEQ ID NO:17) and wherein X$_{28}$ is a nonnatural amino acid (e.g., as listed in Table 1).

In any of the peptides of this invention that recite X$_{28}$, X$_{28}$ can be the same nonnatural amino acid or a different nonnatural amino acid, in any combination.

In further embodiments, the peptide of this invention can comprise a protein transduction domain (PTD), also known as a cell penetrating peptide, at the amino and/or carboxy terminus. Nonlimiting examples of a protein transduction domain include GRKKRRQRRPPQ (SEQ ID NO:18), RQIKIWFQNRRMKWKK (SEQ ID NO:19), PFVYLI (SEQ ID NO:20), GWTLNSAGGYLLGKINLKA-LAALAKKI (SEQ ID NO:21), RRRRRRRRR (SEQ ID NO:22), RRRRRRR (SEQ ID NO:23), KETWWETW-WTWWSQPKKKRKV (SEQ ID NO:24), YGRK-KRRQRRR (SEQ ID NO:25), YARAAARQARA (SEQ ID NO:26), KETWWETWWTEWS (SEQ ID NO:27), GWTLNSAGYLLGKINLKALAALAKKIL (SEQ ID NO:28), Cre recombinase, DAATATRGRSAASRPTER-PRAPARSASRPRRPVE (SEQ ID NO:29), KMTRAQR-RAAARRNRRWTAR (SEQ ID NO:30), and any combination thereof.

In some embodiments, an alphahelical transmembrane domain can be added to the peptide with one or more (e.g., 1, 2, 3, 4, 5, 6, 7, 8, 9, 10, 11, 12, 13, 14, 15, 16, 17, 18, 19, 20, etc.) polyethylene glycol (PEG) linkers. An alphahelical transmembrane domain is a hydrophobic alpha helix that allows insertion of the peptide into the cell membrane. Nonlimiting examples include IISVYCVTSIIL-PVFFFVASF (SEQ ID NO:31) (transmembrane 5 of human PAR1), FVIYMFVVHFTIPMIIIFFCYGQLVFTV (SEQ ID NO:32) (transmembrane 5 of human rhodopsin) and QAYAIASSIVSFYVPLVIMVFVYS (SEQ ID NO:33) (transmembrane 5 of human Beta-2 adrenergic receptor), In some embodiments of this invention, the peptide of this invention can comprise a lipid added to the peptide with one or more (e.g., 1, 2, 3, 4, 5, 6, 7, 8, 9, 10, 11, 12, 13, 14, 15, 16, 17, 18, 19, 20, etc.) PEG linkers. Nonlimiting examples of a lipid and/or glycolipids of this invention include palmityl, myristyl, farnesyl, geranylgeranyl and glycophosphatidylinsitol. In some embodiments, a peptide of this invention with a lipid linked can be Palm-PEG-PEG-HQDYAE-ALANPIKHVSL-Nle-DQRARQLAA (SEQ ID NO:34).

It is understood that for any of the peptides of this invention, each amino acid can be a D isomer or an L isomer in any combination in the peptide.

A subject of this invention can be a mammal, a reptile, an avian or an amphibian (e.g., mouse, bird, dog, cat, cow, horse, fish). In certain embodiments of this invention, the subject is a mammalian subject and in particular embodiments, the subject is a human.

The cell of these methods can be in vitro and/or in vivo (e.g., in a cell in a subject) and/or ex vivo.

A further embodiment of the present invention provides a composition comprising a peptide of this invention and a pharmaceutically acceptable carrier. By "pharmaceutically acceptable carrier" is meant a carrier that is compatible with other ingredients in the pharmaceutical composition and that is not harmful or deleterious to the subject. The carrier can be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients.

The compositions of this invention can be used, for example, in the production of a medicament for the use in treatment of a disease and/or disorder as described herein.

The compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, intraocular (e.g., injection into the eye) or intravenous), topical (i.e., both skin and mucosal surfaces, including airway surfaces), via eye drops, and transdermal administration, although the most suitable route and dosage intervals in any given case will depend, as is well known in the art, on such factors as the species, age, gender and overall condition of the subject, the nature and severity of the condition being treated and/or on the nature of the particular composition (i.e., dosage, formulation, mode of administration) that is being administered. In some embodiments, the composition of this invention can be administered to a subject as an eye drop solution and/or via injection into the eye.

"Effective amount" as used herein refers to an amount of a vector, nucleic acid, epitope, polypeptide, cell, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature (e.g., *Remington's Pharmaceutical Sciences* (latest edition) and/or by using routine pharmacological procedures.

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder.

A "treatment effective" amount as used herein is an amount that is sufficient to treat (as defined herein) the subject. Those skilled in the art will appreciate that the therapeutic effects need not be complete or curative, as long as some benefit is provided to the subject.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent,", "preventing" or "prevention of" (and grammatical variations thereof) refer to prevention and/or delay of the onset and/or progression of viremia in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The therapeutically effective dosage of any specific peptide or composition of this invention will vary depending on the peptide, the composition and the subject, and will depend, among other things, upon the effect or result to be achieved, the condition of the subject and the route of delivery. In some embodiments, a dosage from about 0.001 (i.e., 1 ug/kg), 0.05, 0.1, 0.2, 0.3. 0.4, 0.5, 0.6, 0.7, 0.8, 0.9 or 1.0 mg/kg, up to about 30, 40 or 50 mg/kg (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg/kg), or more, may be used.

A further nonlimiting example of a dosage range for administration of a peptide of this invention to a subject is from about 25 µl to about 5 ml of a composition comprising about 0.5 nM to about 5 mM of the peptide of this invention. Intervals of administration of each dose can be daily, weekly, monthly, bimonthly, quarterly, annually, etc. Efficacy of treatment can be determined by evidence of a reduction in cancer cells, death of cancer cells and/or no progression of cancer cell proliferation.

In some embodiments, the peptides and compositions of this invention are useful in treating cancer or neoplasm associated with a Gαq mutation or any other disorder in which Gαq is constitutively expressed. Nonlimiting examples include uveal melanoma, melanocytic schwannoma, blue nevus, cutaneous melanoma and any cancer derived from neural crest progenitor cells that contain a mutation in Gαq rendering it constitutively active. In particular embodiments, the peptides and compositions of this invention are administered in an effective amount to a subject (e.g., a human subject in need thereof) to treat uveal melanoma.

In some embodiments, the peptides of this invention can be administered to a cell (e.g., a cell in a subject), via nucleic acid delivery. Thus, the peptide of this invention can be encoded by a nucleic acid molecule that is delivered to a cell according to methods well known in the art for delivery of nucleic acid molecules to cells and transcribed and translated into the peptide. As one nonlimiting example, a nucleotide sequence encoding a peptide of this invention can be incorporated into a nucleic acid vector (e.g., a viral vector, such as adeno-associated virus (AAV)) and delivered to a cell, which can be in a subject. The nucleotide sequence encoding the peptide of this invention can be flanked on one or both ends by nucleotide sequences encoding amino acid sequences that stabilize and/or increase the half life of the peptide of this invention in the subject (see, e.g., Example 4 and FIG. 10). Such stabilizing peptides are known in the art, as well as standard dosages for administration of a nucleic acid molecule (e.g., via a viral vector) to a subject. In some embodiments of this invention, a therapeutic peptide of this invention can be administered to a subject in need thereof (e.g., to the eye) to treat uveal melanoma, wherein the peptide is delivered in the form of a nucleic acid molecule (e.g., in a viral vector such as an AAV vector or retroviral vector as are well known in the art), which is administered to the subject and translated into the therapeutic peptide that treats the uveal melanoma.

Delivery of drugs and therapeutic compounds is primarily limited by their ability to penetrate the cell membrane. The bioavailability of compounds targeted to intracellular sites depends on the conflicting requirements of being sufficiently polar for administration and distribution, yet non-polar enough to diffuse through the non-polar lipid bilayer of the cell (Begley, *Journal of Pharmacy & Pharmacology* 48:136-146 (1996)). A strategy for delivery of synthetic compounds across cell membranes has been investigated by both industry and academic researchers (R. Service, *Science* 288:28-29 (2000)). Positively charged, cationic peptides are known to cross cell membranes independent of receptors or specific transport mechanisms (Schwarze et al., *Science* 285:1569-1572 (1999); Ho et al., *Cancer Research* 61:474-477 (2001); Morris et al., *Nature Biotechnology* 19:1173-1176 (2001); Pooga et al., *FASEB Journal* 12:67-77 (1998); Derossi et al., *Journal of Biological Chemistry* 271:18188-18193(1996); Pietersz et al., *Vaccine* 19:1397-1405 (2001); Elliott and O'Hare, *Cell* 88:223-233 (1997); Derer et al., *FASEB Journal* 16:132-133 (2002); Will et al., *Nucleic Acids Research* 30:e59 (2002); Rothbard et al., *Journal of Medicinal Chemistry* 45:3612-3618 (2002); Chen et al., *Chemistry & Biology* 8:1123-1129 (2001); Wender et al., *Proceedings of the National Academy of Sciences of the United States of America* 97:13003-13008 (2000)). The transport involves protein transduction domains (PTDs) that are highly charged, short peptides (~10 to 20 amino acids), containing basic amino acids (arginines and lysines), and that have the ability to form hydrogen bonds. The ability of PTDs to cross cell membranes is also concentration-dependent.

Attachment of nucleic acids, peptides, and even large proteins to these PTDs will allow their transduction across all cell membranes in a highly efficient manner (Schwarze and Dowdy, *Trends in Pharmacological Sciences* 21:45-48 (2000)). Three PTDs have been described which share the common characteristics of being potential DNA binding proteins: HIV-TAT, VP22, and Antennapedia (Schwarze et al., *Science* 285:1569-1572 (1999); Derossi et al., *Journal of Biological Chemistry* 271:18188-18193(1996); Elliott and O'Hare, *Cell* 88:223-233 (1997).

The PTD (e.g., cell penetrating peptide (CPP)) derived from the HIV genome, HIV-TAT (trans-activator of transcription, "TAT"), has the ability to move attached peptides, large proteins, and nucleic acids across virtually all cell membranes, including brain, in a non-receptor mediated fashion (Schwarze et al., *Science* 285:1569-1572 (1999); Cao et al., *Journal of Neuroscience* 22:5423-5431 (2002); Gustafsson, et al., *Circulation* 106:735-739 (2002); Nagahara et al., *Nature Medicine* 4:1449-1452 (1998)). The attached proteins are refolded into an active conformation once inside the cell and are biologically active. The full length TAT protein, originally described in 1988, by Green and Lowenstein, is an 86 amino acid protein encoded by the HIV virus (Fawell et al., *Proc. Natl. Acad. Sci. U.S.A.* 91:664-668 (1994); Frankel, and Pabo, *Cell* 55:1189-1193 (1988); Green and Loewenstein, *Cell* 55:1179-1188(1988)). More specifically, an 11 amino acid arginine-and lysine-rich portion of the TAT sequence, YGRKKRRQRRR (SEQ ID NO:24), conjugated to peptides that do not normally cross membranes, is able to transduce across cell membranes and deliver a biologically active fusion protein to tissues. Furthermore, when a TAT-fusion protein was injected into mice for two weeks, there were no gross signs of neurological problems or system distress. Previously, TAT-fusion proteins were shown to be capable of delivering an active fusion protein that affects mitochondrial function, though in both cases, the fusion protein was not processed by the mitochondria. (Cao et al., *Journal of Neuroscience* 22:5423-5431 (2002); Gustafsson, et al., *Circulation* 106:735-739 (2002)).

The present invention further provides screening methods, which can be, e.g., high throughput (HTP) screening assays. Thus, in further embodiments, the present invention provides a method of identifying a test substance having the ability to inhibit G-alpha-q activity, comprising: a) contacting a TAMRA-27-mer peptide with G-alpha-q and GDP and aluminum fluoride and determining a baseline fluorescence polarization value; and b) contacting a TAMRA-27-mer peptide with G-alpha-q, GDP, aluminum fluoride and the test substance and determining a fluorescence polarization value, wherein a fluorescence polarization value of (b) that is lower than the fluorescence polarization value of (a) identifies the test substance as having the ability to inhibit G-alpha-q activity.

Additionally provided herein is a method of identifying a test substance having the ability to increase G-alpha-q activity, comprising: a) contacting a TAMRA-27-mer peptide with G-alpha-q, GDP and aluminum fluoride and determining a baseline fluorescence polarization; and b) contacting a TAMRA-27-mer peptide with G-alpha-q, GDP, aluminum fluoride and the test substance and determining a fluorescence polarization value, wherein a fluorescence polarization value of (b) that is greater than the fluorescence polarization value of (a) identifies the test substance as having the ability to increase G-alpha-q activity. The TAMRA-27-mer peptide employed in the screening methods of this invention can be any 27-mer peptide of this invention. In some embodiments, the TAMRA peptide can be a TAMRA 25 mer peptide, which would be a 27 mer peptide with X26 and X27 at the carboxy terminus. One nonlimiting example of a 27 mer peptide that can be used in the screening methods of this invention is HQDYAEAL ANPIKHVSL-Nle-DQRARQLAA (SEQ ID NO:34).

Substances suitable for screening according to the above methods include small molecules, natural products, peptides, nucleic acids, etc. Sources for compounds include natural product extracts, collections of synthetic compounds, and compound libraries generated by combinatorial chemistry. Libraries of compounds are well known in the art. A small molecule of this invention can be a small molecule present in any number of small molecule libraries, some of which are available commercially, as described above. Small molecule libraries can be obtained from various commercial entities, for example, SPECS and BioSPEC B. V. (Rijswijk, the Netherlands), Chembridge Corporation (San Diego, Calif.), Comgenex U.S.A. Inc., (Princeton, N.J.), Maybridge Chemical Ltd. (Cornwall, UK), and Asinex (Moscow, Russia). One representative example is known as DIVERSet™, available from ChemBridge Corporation, 16981 Via Tazon, Suite G, San Diego, Calif. 92127. DIVERSet™ contains between 10,000 and 50,000 drug-like, hand-synthesized small molecules. Other sources of libraries include the Library of Pharmacologically Active Compounds (LOPAC), the 100K collection of compounds, the kinase targeted set and the epigenetic targeted compounds set, all of which are maintained by the Center for Integrative Chemical Biology and Drug Discovery at the University of North Carolina at Chapel Hill (UNC).

In some embodiments, the compounds are pre-selected to form a "universal" library that covers the maximum pharmacophore diversity with the minimum number of compounds and is suitable for either high throughput or lower throughput screening. For descriptions of additional libraries, see, for example, Tan et al. "Stereoselective Synthesis of Over Two Million Compounds Having Structural Features Both Reminiscent of Natural Products and Compatible with Miniaturized Cell-Based Assays" *Am. Chem Soc.* 120, 8565-

8566, 1998; Floyd et al. *Prog Med Chem* 36:91-168, 1999. Numerous libraries are commercially available, e.g., from AnalytiCon U.S.A. Inc., P.O. Box 5926, A small molecule of this invention can be a small molecule present in any number of small molecule libraries, some of which are available commercially, as described above. Kingwood, Tex. 77325; 3-Dimensional Pharmaceuticals, Inc., 665 Stockton Drive, Suite 104, Exton, Pa. 19341-1151; Tripos, Inc., 1699 Hanley Rd., St. Louis, Mo., 63144-2913, etc.

In certain embodiments of the invention the methods are performed in a high-throughput format using techniques that are well known in the art, e.g., in multiwell plates, using robotics for sample preparation and dispensing, etc. Representative examples of various screening methods may be found, for example, in U.S. Pat. Nos. 5,985,829, 5,726,025, 5,972,621, and 6,015,692. The skilled practitioner will readily be able to modify and adapt these methods as appropriate.

The test substance can be any chemical or biological compound. The test substance may be natural or synthetic. The test substance can vary in size from small organic molecules to peptides or large proteins. In some embodiments the test compound is a small molecule. Protocols for the production, selection and testing of small molecules for their inhibitory effects are routine and well known in the art and can be readily adapted to the methods of this invention by one of ordinary skill in the art.

In certain embodiments of the invention the screening methods are performed in a high-throughput format using techniques that are well known in the art, e.g., in multiwell plates, using robotics for sample preparation and dispensing, etc. Representative examples of various screening methods may be found, for example, in U.S. Pat. Nos. 5,985,829, 5,726,025, 5,972,621, and 6,015,692. The skilled practitioner will readily be able to modify and adapt these methods as appropriate. In some embodiments the small molecule has a molecular weight of more than about 10 Daltons and less than about 5,000 Daltons, of more than about 40 Daltons and less than about 3,000 Daltons, or of more than about 100 Daltons and less than about 2,500 Daltons. Exemplary small molecules include, but are not limited to, peptides, peptoids, proteins, nucleotides, oligonucleotides, oligosaccharides, pharmaceuticals, sugars, fatty acids, steroids, derivatives, structural analogs, or combinations thereof.

Modern analytical methodologies used by clinical and research laboratories include measuring light absorbance (optical density), light emitted from a chemical reaction (luminescence), light emitted due to an external excitation source (fluorescence), and many others. One emerging technology is fluorescence polarization (FP), which is typically used in receptor binding and in protein or DNA analysis assays.

Fluorescence polarization readers excite fluorescent samples with polarized light of a defined wavelength and measure the emitted light in both a parallel and a perpendicular polarization plane. Large fluorescent molecules, which move comparatively slowly, emit a greater percentage of light in a direction generally parallel to the excitation source. Smaller molecules, which move more rapidly, depolarize the light, which results in about the same amount of fluorescence emitted in both polarization planes. Accordingly, fluorescence polarization readers can provide qualitative information about the size of fluorescent compounds and can be used to differentiate bound and unbound fluorophore homogeneously. In contrast to other techniques, a separation step to remove any unbound fluorophore is typically not required.

The growth of biological research, the development of new pharmaceuticals, and the implementation of novel medical diagnostics have created a need for handling large numbers of test samples. A number of methods are now available for high throughput screening of these samples, for example, for binding events. Fluorescence polarization readers may be used as a screening technique, and association assays such as ligand binding, proteolysis, and DNA cleavage can therefore be measured homogeneously, i.e., generally without "washing" or separation steps. Typically, large numbers of binding assays are processed using fluorescence polarization or anisotropy by placing the assays in multiwell sample plates called microplates. These microplates are typically a rectangular array of open wells, usually 24, 96, or 384 wells in typical examples, but 1536 well and other format microplates may also be used. These microplate wells are filled with test samples and then placed in a fluorescence polarization microplate reader. Fluorescence polarization readers are typically configured to read a polarization value (e.g., measured in "milli-polarization units" or "mP") from each of the well positions. (See, e.g., Kimple et al. "A high-throughput fluorescence polarization assay for inhibitors of the GoLoco motif/G-alpha interaction" *Comb Chem High Throughput Screen* 11(5):396-409 (2008)).

The examples below are set forth to illustrate the present invention, and are not to be construed as limiting thereof.

EXAMPLES

The high-resolution crystal structure of Gαq-GDP activated with aluminum fluoride and bound to its effector, PLC-β3 has been determined[11]. The structure highlighted a short helix-turn-helix within PLC-β3 that bound within the effector site of Gαq and provided the majority of contacts for complex formation. Activated Gαq was shown to bind p63RhoGEF in an almost identical fashion. Guided by these structures, peptides have been designed that bind with high affinity to the effector site of Gαq and potently inhibit its capacity to activate either PLC-β3 or p63RhoGEF. The peptides are highly selective: they do not bind the inactive, GDP-bound form of Gαq and they do not bind other Ga subunits. Fluorescent versions of these peptides have dramatically increased polarization upon complex formation with activated Gαq and this property has been used to design a high-throughput assay to screen for small molecules that bind the effector site of Gαq and displace bound peptide. Such compounds would provide excellent leads for the development of potent and selective inhibitors of Gαq.

Convergent Signaling by N-Ras and Gαq Contribute to Cancers

It is well established that diverse receptor tyrosine kinases (RTKs) initially activate N-Ras leading to the subsequent activation of the MAPK cascade (B-Raf, MEK1/2 and ERK1/2) necessary for proliferation (FIG. 1). N-Ras is a GTPase and in its GTP-bound state directly activates B-Raf. Mutations (e.g., Q61L) in N-Ras that prevent its capacity to hydrolyze GTP lead to the constitutive activation of the MAPK cascade and concomitant cellular transformation. Similarly mutations in B-Raf (e.g., V600E) that lead to its constitutive activation also drive the MAPK cascade and cellular transformation[11]. The majority of cutaneous melanomas are driven by constitutively active N-Ras (20%) or B-Raf (50%)[12].

Less well appreciated is the activation of the MAPK cascade by G protein-coupled receptors (GPCRs) (FIG. 1). These receptors directly activate heterotrimeric G-proteins (Gαβγ). Like the Ras isozymes, Gα subunits are GTPases that when bound to GTP directly activate effectors. Analogous to N-Ras(Q61L), Gαq(Q209L) is GTPase deficient; constitutively activates the MAPK cascade; and promotes cellular transformation. Approximately 50% of uveal melanomas contain Gαq(Q209L) or similarly active Gα subunits related to Gαq[3,4]. The PLC-β isozymes are the best understood effectors of Gαq, and like B-Raf, several potentially activating mutations in PLC-β isozymes have recently been discovered in genome wide screens of cancers[13].

There are many inhibitors of the MAPK pathway, however there are no FDA-approved drugs that target this pathway and lead to complete tumor regression. While many of these drugs dramatically shrink tumor load, they do not consequently extend patient lifespan, presumably due to secondary mutations or contributions of ancillary pathways to tumor progression[14]. Indeed many current treatment regimens combine B-Raf inhibition with other therapies. One possibility is that signaling through Gαq and PLC-β isozymes supports transformation of melanocytes primarily driven by B-Raf and N-Ras. The studies described herein are for the purpose of identifying the potential synergies among Gαq, N-Ras and B-Raf in melanocytic transformations.

A Helix-Turn-Helix of PLC-β3 is the Major Determinant for Binding to Gαq

Structures of Gαq bound to either PLC-β3[15] or p63RhoGEF[16] highlight an essentially identical mechanism of effector engagement—the canonical effector-binding site of Gαq is occupied by a helix-turn-helix (HTH) of either PLC-β3 or p63RhoGEF (FIG. 6A). These helices are assumed to be relatively mobile prior to complex formation with transient secondary structure induced by the complex.

Initially, a nested set of TAMRA-labeled peptides spanning the HTH of PLC-β3 was synthesized and tested for binding to Gαq using fluorescence polarization (FIG. 6B). The shorter peptides showed no binding to Gαq, while the largest peptide of 25 residues (TAMRA-25-mer), and spanning the entire HTH, bound to Gαq with appreciable affinity ($K_d$~6 µM). The complex was dependent on the activation of Gαq with aluminum fluoride and specific since neither activated Gαs, GαI, nor Gαo bound the peptide. This result was expected, since sequence variation within the canonical effector binding site of Gα subunits is the predominant determinant of effector selectivity[17]. Moreover, full-length PLC-β3 inhibited TAMRA-25-mer binding to Gαq ($IC_{50}$~1 µM) (FIG. 6C), whereas a mutant PLC-β3(L859E) that does not bind Gαq had no effect at concentrations as high as 35 µM. Since full-length PLC-β3 binds activated Gαq with a dissociation constant ($K_D$) of approximately 10-100 nM[15,18], these results indicate that the 25-mer retains the majority of determinants for binding to Gαq. These results support the possibility of using optimized peptide analogues to interdict Gαq signaling.

Efficient Inhibition of Phospholipase Activity

A 25 residue peptide of PLC-β3 binds with high affinity to Gαq and effectively competes with full-length PLC-β3 for binding to Gαq (FIGS. 6A-C). These results strongly suggest that this peptide should also prevent the capacity of Gαq to activate PLC-β3 and this idea was tested directly using purified proteins (FIG. 7). In this case, purified Gαq and PLC-β3 were reconstituted with lipid vesicles; Gαq was activated with aluminum fluoride; and phospholipase activity was measured as a function of increasing concentrations of TAMRA-27-mer. The peptide inhibited phospholipase activity with low micromolar potency ($IC_{50}$~1 µM), consistent with its affinity for Gαq. A peptide corresponding to the HTH of PLC-β3 and containing an 1860 A substitution dramatically enhanced the inhibitory potential relative to the 27-mer peptide (FIG. 2B). The corresponding $IC_{50}$ was approximately 100 nM, suggesting that this peptide is an excellent scaffold for designing peptidomimetics to inhibit constitutively active Gαq in cells.

Figures 7A, 7B:
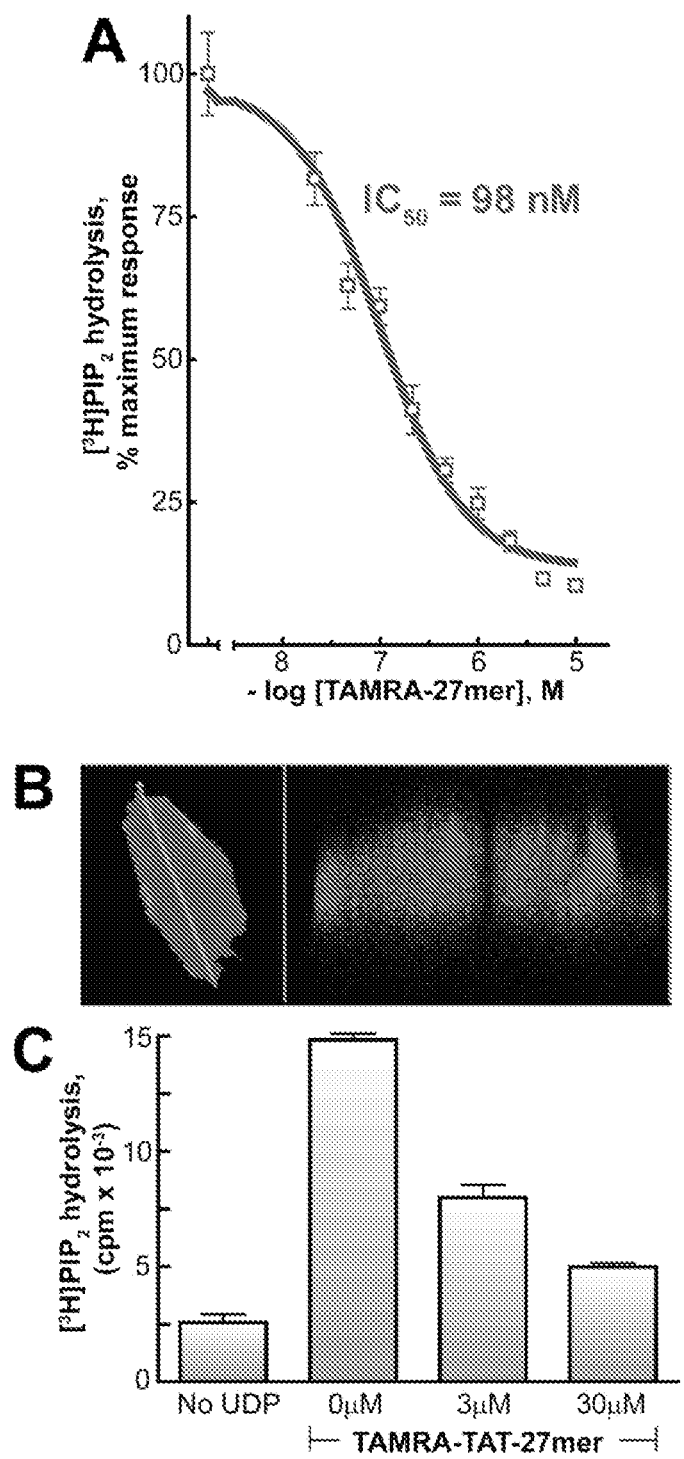
FIGS. 7A and 7B. HTH inhibits Gαq-mediated activation of PLC-β in vesicles and cells.
Figure 9:
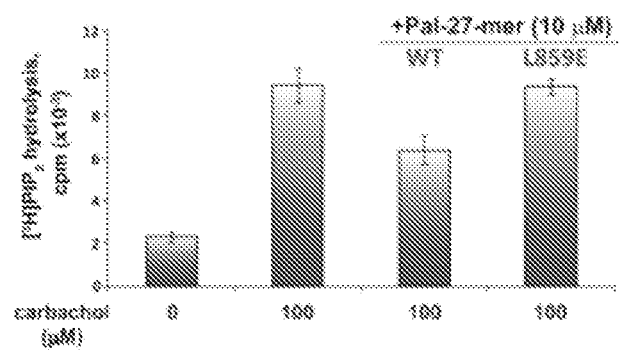
FIG. 9. Muscarinic receptor-dependent activation of PLC-β was determined by quantification of [$^3$H]inositol phosphate accumulation. Where indicated, HEK293 cells were treated with Palm-27-mer peptide for 30 minutes.

Since a major tenet of this invention is to interdict Gαq signaling in cells with peptidomimetics, it will be necessary to efficiently introduce peptides derived from this scaffold into cells. As a first step in this process, we show that a peptide corresponding to the HTH of PLC-β3 can efficiently and uniformly enter cells (FIG. 7B). Moreover, once introduced, this peptide prevented the stimulation of PLC activity by Gαq downstream of the P2Y6 receptor and/or muscarinic receptor, a G protein-coupled receptor selective for Gαq (FIG. 7C and FIG. 9).

Example 1

Design and Optimization of Peptidomimetics that Directly and Potently Compete with Effectors for Binding Gαq and Use of These Reagents to Inhibit the Transforming Potential of Constitutively Active Gαq in Uveal Melanomas.

A small peptide derived from PLC-β3 has been shown to effectively prevent the capacity of Gαq to bind full-length PLC-β3 and potently inhibit phospholipase activity. This peptide provides a framework for modifications to create peptidomimetics that are resistant to proteases and have high bioavailability. In general, peptidomimetics will consist of "stapled" peptides that serve to stabilize the helix-turn-helix observed in the crystal structure of PLC-β3 bound to Gαq. These peptidomimetics will be used to interdict and probe Gαq-mediated signaling in uveal melanoma cell lines.

Interdicting Gαq Signaling with Peptidomimetics

Stapling involves incorporation of non-natural amino acids, and first sites within the HTH of PLC-β3 will be identified that can accept alterations without affecting interaction with Gαq. A set of peptides corresponding to the HTH and containing individual sites mutated to alanine will be individually titrated into a solution containing activated Gαq and TAMRA-25-mer. Corresponding $IC_{50}$ values for this set of peptides will be determined from these competition curves as shown previously for full length PLC-β3 (FIG. 6C). The alanine scan will be done within the background of the 25-mer; residues that bury the majority of their side chain in the structure of PLC-β3 bound to Gαq[15] will not be included.

This scan will map sites that can accept non-natural amino acids, and these sites will be used to create staples in synthetic peptides corresponding to the HTH of PLC-β3. Individual staples will be created by introducing pairs of olefinic (2-(4'-pentenyl)alanine) derivatives followed by olefin metatheses to covalently link the non-natural amino acids[23,24]. Olefin metathesis will be monitored using mass spectroscopy (MS/MS). Staples will be introduced individually within the N- and C-terminal helices at residues i, i+4 of the HTH. Similar staples promote helicity in other peptides and often increase affinity (>10-fold) of helical peptides to their target proteins[25,26,27]. The affinities of these stapled forms of the HTH for Gαq will be determined using the competition assay described above (FIG. 6C). The peptidomimetics with the highest affinity for Gαq are expected to effectively inhibit the capacity of Gαq to modulate downstream effectors, and this idea will be tested directly using purified proteins reconstituted into lipid vesicles as described above (FIGS. 7A and 7B). Variable length staples also will be introduced between the two helices to stabilize the intervening turn and also tested. As an added advantage, staples in peptides often increase bioavailability and enhance protease resistance[28].

Interdicting Gαq Signaling with Peptidomimetics in Uveal Melanomas

The stapled peptides of the HTH of PLC-β3 with the highest potency to inhibit Gαq will be assessed for the capacity to inhibit constitutively active Gαq(Q209L) in uveal melanoma cell lines (OMM1.3 and Mel202). These cell lines were used previously to demonstrate that siRNA-mediated knockdown of Gαq decreased signaling through the MAPK cascade with a concomitant reduction of anchorage-independent growth[3]. Thus, these cell lines will be used in studies of the inhibition of Gαq with the peptidomimetics of this invention and the activation of the MAPK cascade as previously described[3].

The capacity of the peptidomimetics to enter these cell lines will be optimized using the techniques described previously (FIG. 7B), and ERK phosphorylation and cyclin D levels will be monitored using standard techniques as surrogates of the activation of the MAPK cascade[3,29]. The peptidomimetics are expected to penetrate uveal melanoma cells and cause efficient inhibition of constitutively active Gαq, leading to a decrease of ERK phosphorylation and cyclin D levels associated with tumorigenesis. These studies are designed to optimize the techniques and reagents needed to easily and efficiently interdict Gαq signaling in cells. Since constitutively active Gαq directly contributes to the progression of uveal melanoma, these studies will establish new avenues for the study and treatment of melanomas.

Defining the Contributions of Gαq-Mediated Activation of PLC-β Isozymes in Promoting the Malignant Transformation of Melanocytes.

Activated Gαq stimulates the MAPK pathway and promotes the transformation of melanocytes. Constitutively active Gαq is often found in benign blue nevi derived from cutaneous melanocytes but is rarely found in cutaneous melanomas driven by B-Raf and N-Ras. Given the observation that constitutively active Gαq promotes uveal melanomas and blue nevi, Gαq might also support transformation of cutaneous melanomas through cross talk with constitutively active B-Raf or N-Ras. The studies described herein will assess potential synergies between constitutively active forms of Gαq, B-Raf and N-Ras in promoting transformation of cutaneous melanocytes.

Contributions of Gαq and PLC-β Isozymes in Transforming Melanocytes

A model cell line of melanocytes will be used in these studies. Human primary melanocytes have been immortalized through the expression of human telomerase catalytic subunit and a dominant negative mutant of the tumor suppressor p53. This cell line has also been engineered to allow the inducible expression of genes under the control of a tetracycline inducible promoter. This cell line will be stably transformed with inducible forms of either wild-type or constitutively active Gαq using retroviral-mediated transformation for high efficiency. Inducible expression of Gαq will be assessed by Western blot and several clonal cell lines capable of expressing varying levels of Gαq will be maintained for subsequent studies.

To define the contributions of Gαq in the transformation of melanocytes, a battery of experiments will be used to assess aspects of cellular transformation as a function of Gαq expression. Gαq will be induced with doxycyclin in the clonal cell lines produced above. Constitutively active Gαq is expected to robustly activate the MAPK cascade relative to more modest activation by wild-type Gαq. Activation of the MAPK cascade will be monitored by ERK phosphorylation and cyclin D1 levels as described herein. The capacity of induced Gαq expression to overcome contact inhibition of growth will be determined using foci formation assays[30]. In this case, cells will be seeded at low density (100-200 cells) followed by induced expression of Gαq; cells will be grown for 15-18 days, and stained with crystal violet to highlight foci prior to counting. Overexpression of constitutively active Gαq is expected to promote the formation of colonies; conversely, overexpression of wild-type Gαq is not expected to form colonies. For cell lines that support colony growth, anchorage independence will be tested using conventional agar-based assays[3].

Figure 8:
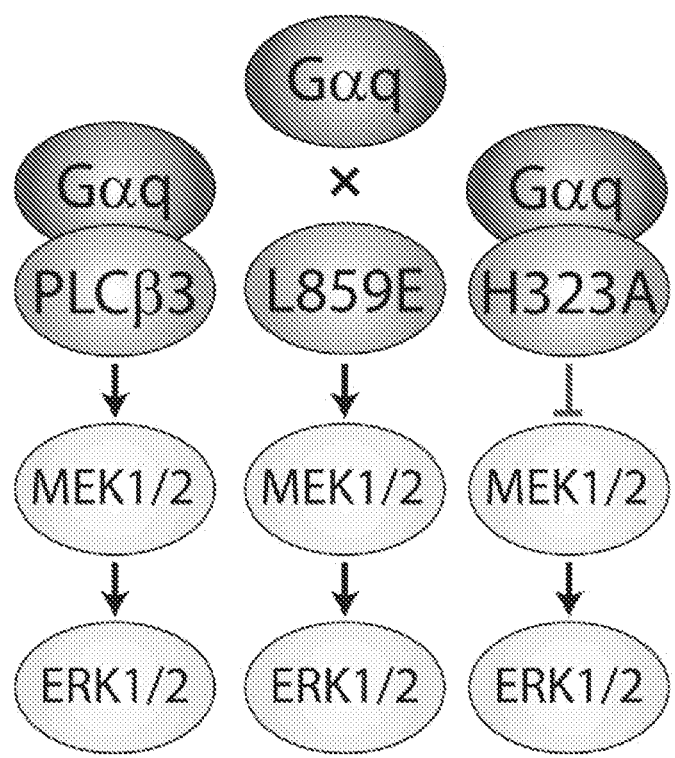
FIG. 8. Differential signaling by mutant PLCβ3 isozymes. PLC-β3 (L859E) cannot bind Gαq. PLC-β3(H323A) is lipase deficient.

Once these initial studies are completed, forms of PLC-β3 will be introduced into these cell lines to dissect specific events mediated by Gαq (FIG. 8). Like heterotrimeric G proteins, PLC-β isozymes are basally and tightly auto-inhibited. They require activation by Gαq or other modulators to enhance lipase activity[31]. Hence, no substantial increase in PIP$_2$ hydrolysis or associated downstream signaling (e.g., MAPK activation) is expected upon inducible expression of PLC-β3 alone. In contrast, co-expression of wild-type Gαq may modestly increase PIP$_2$ hydrolysis, MAPK activation, and promote transformation; co-expression of constitutively active Gαq should drive robust PIP$_2$ hydrolysis and associated events. In these cases MAPK activation and transformation will be monitored as above; PIP$_2$ hydrolysis will be measured as described[15] and shown in FIG. 7C.

Additionally, PLC-β3 harboring a single substitution (L859E) specifically destroys the capacity of Gαq to bind, but is otherwise catalytically competent. Co-expression of PLC-β3(L859E)[15] either alone or in conjunction with Gαq forms should not elevate PIP$_2$ hydrolysis or modulate associated events. In this case, if Gαq continues to stimulate the MAPK cascade and drive transformation, these results will be interpreted as indicating that Gαq signals through other effectors (i.e., RhoGEFs) to modulate these processes.

Complementary studies will use PLC-β3(H323A)[32]. This mutant is catalytically dead, but is completely functional to bind Gαq. PLC-β3(H323A) will be coexpressed with both forms of Gαq. Under no circumstances should PIP$_2$ hydrolysis be elevated. Indeed, it might be the case that PLC-β3 (H323A) behaves as a dominant negative to sequester activated Gαq. If so, PIP$_2$ hydrolysis and associated events would be reduced. Scenarios using mutant PLC-β3 isozymes will be tested using the techniques described for the study of wild-type PLC-β3.

Contributions of Gαq in Melanomas Driven by N-Ras and B-Raf

Constitutively active Gαq clearly increases the proliferation of cutaneous melanocytes to produce blue nevi. However constitutively active Gαq is rarely found in cutaneous melanomas. Signaling by Gαq may synergize with constitutively active B-Raf or N-Ras to transform cutaneous melanomas. These studies will assess the potential contributions of Gαq in supporting the transformation of cutaneous melanocytes.

More specifically, siRNA will be used to knockdown Gαq in two well studied cell lines of cutaneous melanomas: SK-MEL-28 harboring constitutively active B-Raf and SK-MEL-2 harboring constitutively active N-Ras. In these cases, MAPK activation and cellular proliferation will be measured as a function of titrating sorafenib to inhibit B-Raf. Sorafenib will be used at several concentrations below its LD$_{50}$. If Gαq supports transformation in these cell lines it is expected that its knockdown will synergize with B-Raf inhibition to reduce MAPK activation and colony formation, as well as, possibly increase cell death. MAPK activation and colony formation will be measured as described above. Cell death will be measured using a conventional caspase cleavage assay[33].

Similar studies will be carried out to titrate the inhibition of B-Raf while using peptidomimetics of this invention to inhibit Gαq.

REFERENCES

1. Singh, A. D., Bergman, L. & Seregard, S. (2005). Uveal melanoma: epidemiologic aspects. *Ophthalmol Clin North Am* 18, 75-84, viii.
2. Singh, A. D. & Topham, A. (2003). Survival rates with uveal melanoma in the United States: 1973-1997. *Ophthalmology* 110, 962-5.
3. Van Raamsdonk, C. D., Bezrookove, V., Green, G., Bauer, J., Gaugler, L., O'Brien, J. M., Simpson, E. M., Barsh, G. S. & Bastian, B. C. (2009). Frequent somatic mutations of GNAQ in uveal melanoma and blue naevi. *Nature* 457, 599-602.
4. Van Raamsdonk, C. D., Griewank, K. G., Crosby, M. B., Garrido, M. C., Vemula, S., Wiesner, T., Obenauf, A. C., Wackernagel, W., Green, G., Bouvier, N., Sozen, M. M., Baimukanova, G., Roy, R., Heguy, A., Dolgalev, I., Khanin, R., Busam, K., Speicher, M. R., O'Brien, J. & Bastian, B. C. (2010). Mutations in GNA11 in uveal melanoma. *N Engl J Med* 363, 2191-9.
5. Seo, B., Choy, E. W., Maudsley, S., Miller, W. E., Wilson, B. A. & Luttrell, L. M. (2000). Pasteurella multocida toxin stimulates mitogen-activated protein kinase via G(q/11)-dependent transactivation of the epidermal growth factor receptor. *J Biol Chem* 275, 2239-45.
6. Hawes, B. E., van Biesen, T., Koch, W. J., Luttrell, L. M. & Lefkowitz, R. J. (1995). Distinct pathways of Gi- and Gq-mediated mitogen-activated protein kinase activation. *J Biol Chem* 270, 17148-53.
7. Singh, A. D., Wang, M. X., Donoso, L. A., Shields, C. L., De Potter, P. & Shields, J. A. (1996). Genetic aspects of uveal melanoma: a brief review. *Semin Oncol* 23, 768-72.
8. Triozzi, P. L., Eng, C. & Singh, A. D. (2008). Targeted therapy for uveal melanoma. *Cancer Treat Rev* 34, 247-58.
9. Saldanha, G., Purnell, D., Fletcher, A., Potter, L., Gillies, A. & Pringle, J. H. (2004). High BRAF mutation frequency does not characterize all melanocytic tumor types. *Int J Cancer* 111, 705-10.
10. Zuidervaart, W., van Nieuwpoort, F., Stark, M., Dijkman, R., Packer, L., Borgstein, A. M., Pavey, S., van der Velden, P., Out, C., Jager, M. J., Hayward, N. K. & Gruis, N. A. (2005). Activation of the MAPK pathway is a common event in uveal melanomas although it rarely occurs through mutation of BRAF or RAS. *Br J Cancer* 92, 2032-8.
11. Inamdar, G. S., Madhunapantula, S. V. & Robertson, G. P. (2010). Targeting the MAPK pathway in melanoma: why some approaches succeed and other fail. *Biochem Pharmacol* 80, 624-37.
12. Romano, E., Schwartz, G. K., Chapman, P. B., Wolchock, J. D. & Carvajal, R. D. (2011). Treatment implications of the emerging molecular classification system for melanoma. *Lancet Oncol* 12, 913-22.
13. Wei, X., Walia, V., Lin, J. C., Teer, J. K., Prickett, T. D., Gartner, J., Davis, S., Stemke-Hale, K., Davies, M. A., Gershenwald, J. E., Robinson, W., Robinson, S., Rosenberg, S. A. & Samuels, Y. (2011). Exome sequencing identifies GRIN2A as frequently mutated in melanoma. *Nat Genet* 43, 442-6.
14. Augustine, C. K., Toshimitsu, H., Jung, S. H., Zipfel, P. A., Yoo, J. S., Yoshimoto, Y., Selim, M. A., Burchette, J., Beasley, G. M., McMahon, N., Padussis, J., Pruitt, S. K., Ali-Osman, F. & Tyler, D. S. (2010). Sorafenib, a multikinase inhibitor, enhances the response of melanoma to regional chemotherapy. *Mol Cancer Ther* 9, 2090-101.
15. Waldo, G. L., Ricks, T. K., Hicks, S. N., Cheever, M. L., Kawano, T., Tsuboi, K., Wang, X., Montell, C., Kozasa, T., Sondek, J. & Harden, T. K. (2010). Kinetic scaffolding mediated by a phospholipase C-b and Gq signaling complex. *Science* 330, 974-80.
16. Lutz, S., Shankaranarayanan, A., Coco, C., Ridilla, M., Nance, M. R., Vettel, C., Baltus, D., Evelyn, C. R., Neubig, R. R., Wieland, T. & Tesmer, J. J. (2007). Structure of Ga$_q$-p63RhoGEF-RhoA complex reveals a pathway for the activation of RhoA by GPCRs. *Science* 318, 1923-7.
17. Lambright, D. G., Sondek, J., Bohm, A., Skiba, N. P., Hamm, H. E. & Sigler, P. B. (1996). The 2.0 A crystal structure of a heterotrimeric G protein. *Nature* 379, 311-9.
18. Lyon, A. M., Tesmer, V. M., Dhamsania, V. D., Thal, D. M., Gutierrez, J., Chowdhury, S., Suddala, K. C., Northup, J. K. & Tesmer, J. J. (2011). An autoinhibitory helix in the C-terminal region of phospholipase C-b mediates Gαq activation. *Nat Struct Mol Biol* 18, 999-1005.
19. Tesmer, J. J., Sunahara, R. K., Johnson, R. A., Gosselin, G., Gilman, A. G. & Sprang, S. R. (1999). Two-metal-Ion catalysis in adenylyl cyclase. *Science* 285, 756-60.
20. Slep, K. C., Kercher, M. A., He, W., Cowan, C. W., Wensel, T. G. & Sigler, P. B. (2001). Structural determinants for regulation of phosphodiesterase by a G protein at 2.0 A. *Nature* 409, 1071-7.
21. Lutz, S., Freichel-Blomquist, A., Yang, Y., Rumenapp, U., Jakobs, K. H., Schmidt, M. & Wieland, T. (2005). The guanine nucleotide exchange factor p63RhoGEF, a specific link between Gq/11-coupled receptor signaling and RhoA. *J Biol Chem* 280, 11134-9.
22. Tesmer, V. M., Kawano, T., Shankaranarayanan, A., Kozasa, T. & Tesmer, J. J. (2005). Snapshot of activated G proteins at the membrane: the Gαq-GRK2-Gbg complex. *Science* 310, 1686-90.
23. Miller, S. J. & Grubbs, R. H. (1995). Synthesis of Conformationally Restricted Amino-Acids and Peptides Employing Olefin Metathesis. *J Am Chem Soc* 117, 5855-5856.
24. Blackwell, H. E., Sadowsky, J. D., Howard, R. J., Sampson, J. N., Chao, J. A., Steinmetz, W. E., O'Leary, D. J. & Grubbs, R. H. (2001). Ring-closing metathesis of olefinic peptides: design, synthesis, and structural characterization of macrocyclic helical peptides. *J Org Chem* 66, 5291-302.
25. Jacobsen, O., Klaveness, J. & Rongved, P. (2010). Structural and pharmacological effects of ring-closing metathesis in peptides. *Molecules* 15, 6638-77.
26. Moellering, R. E., Cornejo, M., Davis, T. N., Del Bianco, C., Aster, J. C., Blacklow, S. C., Kung, A. L., Gilliland, D. G., Verdine, G. L. & Bradner, J. E. (2009). Direct inhibition of the NOTCH transcription factor complex. *Nature* 462, 182-8.
27. Bernal, F., Tyler, A. F., Korsmeyer, S. J., Walensky, L. D. & Verdine, G. L. (2007). Reactivation of the p53 tumor suppressor pathway by a stapled p53 peptide. *J Am Chem Soc* 129, 2456-7.

28. Bird, G. H., Madani, N., Perry, A. F., Princiotto, A. M., Supko, J. G., He, X., Gavathiotis, E., Sodroski, J. G. & Walensky, L. D. Hydrocarbon double-stapling remedies the proteolytic instability of a lengthy peptide therapeutic. *Proc Natl Acad Sci U.S.A.* 107, 14093-8.
29. Shields, J. M., Thomas, N. E., Cregger, M., Berger, A. J., Leslie, M., Torrice, C., Hao, H., Penland, S., Arbiser, J., Scott, G., Zhou, T., Bar-Eli, M., Bear, J. E., Der, C. J., Kaufmann, W. K., Rimm, D. L. & Sharpless, N. E. (2007). Lack of extracellular signal-regulated kinase mitogen-activated protein kinase signaling shows a new type of melanoma. *Cancer Res* 67, 1502-12.
30. Bower, J. J., Karaca, G. F., Zhou, Y., Simpson, D. A., Cordeiro-Stone, M. & Kaufmann, W. K. (2010). Topoisomerase IIalpha maintains genomic stability through decatenation G(2) checkpoint signaling. *Oncogene* 29, 4787-99.
31. Hicks, S. N., Jezyk, M. R., Gershburg, S., Seifert, J. P., Harden, T. K. & Sondek, J. (2008). General and versatile autoinhibition of PLC isozymes. *Mol Cell* 31, 383-94.
32. Ellis, M. V., James, S. R., Perisic, O., Downes, C. P., Williams, R. L. & Katan, M. (1998). Catalytic domain of phosphoinositide-specific phospholipase C (PLC). Mutational analysis of residues within the active site and hydrophobic ridge of plcd1. *J Biol Chem* 273, 11650-9.
33. Stennicke, H. R. & Salvesen, G. S. (1999). Catalytic properties of the caspases. *Cell Death Differ* 6, 1054-9.
34. Whitehurst, A. W., Bodemann, 13. 0., Cardenas, A., Ferguson, D., Girard, L., Peyton, M., Minna, J. D., Michnoff, C., Hao, W., Roth, M. G., Xie, X. J. & White, M. A. (2007). Synthetic lethal screen identification of chemosensitizer loci in cancer cells. *Nature* 446, 815-9.
35. Bedikian, A. Y. (2006). Metastatic uveal melanoma therapy: current options. *Int Ophthalmol Clin* 46, 151-66.
36. Egan, K. M., Seddon, J. M., Glynn, R. J., Gragoudas, E. S. & Albert, D. M. (1988). Epidemiologic aspects of uveal melanoma. *Surv Ophthalmol* 32, 239-51.
37. Shields, C. L. & Shields, J. A. (2009). Ocular melanoma: relatively rare but requiring respect. *Clin Dermatol* 27, 122-33.
38. Kusters-Vandevelde, H. V., Klaasen, A., Kusters, B., Groenen, P. J., van Engen-van Grunsven, I. A., van Dijk, M. R., Reifenberger, G., Wesseling, P. & Blokx, W. A. (2009). Activating mutations of the GNAQ gene: a frequent event in primary melanocytic neoplasms of the central nervous system. *Acta Neuropathol.*
39. Sjoblom, T., Jones, S., Wood, L. D., Parsons, D. W., Lin, J., Barber, T. D., Mandelker, D., Leary, R. J., Ptak, J., Silliman, N., Szabo, S., Buckhaults, P., Farrell, C., Meeh, P., Markowitz, S. D., Willis, J., Dawson, D., Willson, J. K., Gazdar, A. F., Hartigan, J., Wu, L., Liu, C., Parmigiani, G., Park, B. H., Bachman, K. E., Papadopoulos, N., Vogelstein, B., Kinzler, K. W. & Velculescu, V. E. (2006). The consensus coding sequences of human breast and colorectal cancers. *Science* 314, 268-74.

Example 2

Optimization, Validation, and Implementation of High-Throughput Screens Based on a Fluorescence Polarization Assay to Identify Small-Molecule Inhibitors of Activated Gαq and Validate the Inhibitory Potentials, Selectivity Profiles, and Cellular Activities of Small Molecules Identified as Inhibitors of Activated Gαq.
Convergent Signaling by N-Ras and Gαq Contribute to Cancers These studies are focused on identifying inhibitors of Gαq that can be used as: i) probes to better understand signal transduction cascades controlled by Gαq and, ii) lead compounds for drug development to treat ocular melanoma.

Canonical Effector Interactions with Gαq Drive Complex Formation

A nested set of TAMRA-labeled peptides spanning the HTH of PLC-β3 were synthesized and tested using fluorescence polarization for binding to Gαq activated with aluminum fluoride—an ionic complex that mimics the terminal phosphate of GTP within the active site of Gα subunits. Peptides encompassing only a portion of the HTH showed no appreciable binding to activated Gαq (FIG. 2B). In contrast, a 25-mer peptide of PLC-β3 spanning all residues within the HTH that contact Gαq bound to active Gαq with a $K_d$ of approximately 6 µM. Several other derivatives of the HTH were also tested and a TAMRA-labeled 27-mer (residues 852-878 of PLC-β3 with two mutations (Ile860A+ M869Nle)) showed the highest affinity ($K_d$~400 nM) for active Gαq. The 27-mer was highly selective for Gαq since it did not bind other Gα subunits (FIG. 2C) and complex formation required activation of Gαq since Gαq-GDP without added aluminum fluoride also did not bind the 27-mer (FIG. 2C). Finally, a chimeric form of Gαq (Gαq/i) that allows high-yield expression in *E. coli* bound the 27-mer with reasonable affinity (FIG. 2C; $K_d$=1.6 µM) that was dependent on aluminum fluoride.

Figures 3A, 3B:
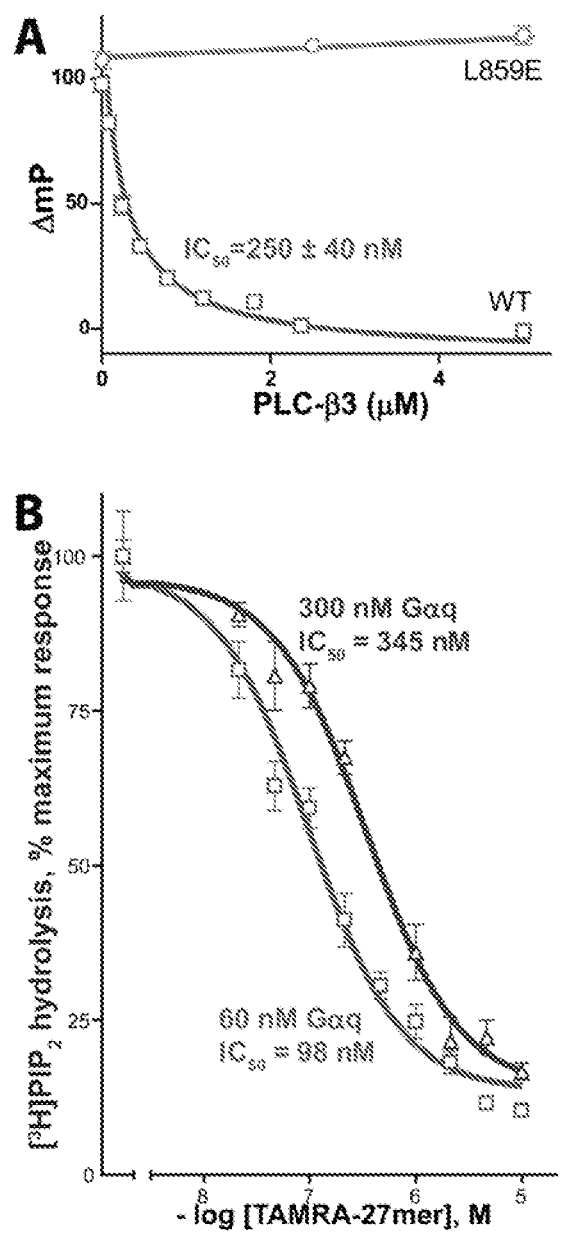
FIGS. 3A and 3B. TAMRA-27-mer and PLC-β3 directly compete for Gαq.

Fluorescence polarization will be used to monitor disruption of complex formation between the 27-mer and active Gαq to identify compounds that directly compete with the complex. It is expected that the majority of these compounds will sit within the canonical effector-binding site of Gαq to prevent the binding of peptide—and by extension, prevent the binding of effectors. However, before using this assay format to identify inhibitors of complex formation it was necessary to insure that peptides corresponding to the HTH of PLC-β3 bound to Gαq. First, it was shown that full-length PLC-β3 could effectively compete with the 27-mer for binding to Gαq (FIG. 3A). In contrast, a form of full-length PLC-β3 harboring a single substitution, (L859E) within its HTH and that does not bind Gαq could not compete with the 27-mer for binding active Gαq. These results suggest direct competition between the 27-mer and wild-type PLC-P3 for binding to the effector site on Gαq. Indeed, this suggestion is supported by the essentially identical, but off-set curves plotting the phospholipase activity of purified PLC-β3 as a function of purified Gαq and its inhibition by TAMRA-27-mer (FIG. 3B). TAMRA-27-mer also inhibits the capacity of Gαq to activate p63RhoGEF. These experiments strongly support that peptides corresponding to the HTH of PLC-β3 directly bind to the effector pocket of Gαq and can be used as surrogates of effectors in assays of complex formation with active Gαq.

Up to this point, these studies have focused on defining probes derived from the HTH of PLC-β3 that can be used to interrogate selectively the effector-binding site of active Gαq. The TAMRA-27-mer described above fits these criteria: it binds with high affinity and selectivity to active Gαq and it directly competes with PLC-β3 for the effector site on Gαq. With this probe in hand, a high-throughput assay will be developed to identify small molecules that directly compete with TAMRA-27-mer for binding to the effector site of active Gαq. These small molecules will serve as initial leads to develop potent inhibitors of active Gαq to both probe signaling by Gαq, as well as to treat diseases promoted by constitutively active Gαq.

High-Throughput Assay Using Fluorescence Polarization

Figure 4:
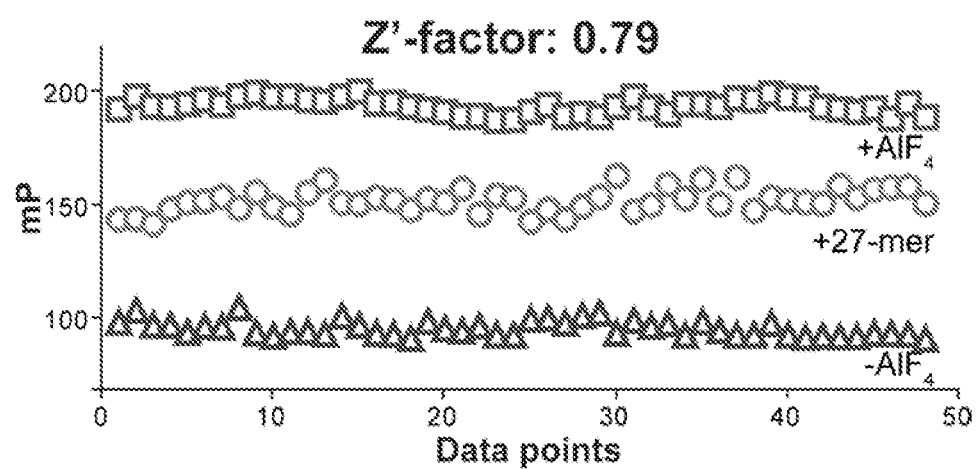
FIG. 4. Fluorescence polarization assay in 384 well plates. Each well contains 200 nM TAMRA-27-mer and 1.5 μM Gαq/i. Z'-factor determined using 48 wells+/–aluminum fluoride (AlF4). Unlabeled 27-mer (30 μM) added to an additional 48 wells. Coefficient of variance range between 1 and 4 percent.

To begin to develop a high-throughput format suitable for screening large libraries of compounds, the original fluorescence polarization assay was formatted to use microtiter plates (FIG. 4). The initial reconfiguration to use 384-well plates is highly promising, providing a high dynamic range as defined by the difference in fluorescence polarization of the TAMRA-27-mer in the presence of Gαq-GDP either alone or activated with aluminum fluoride. The high dynamic range combined with low variance produced a Z'-factor of approximately 0.8. An assay with a Z'-factor above 0.5 is generally required for useful high-throughput screening[19]; a Z'-factor above 0.8 is generally considered excellent. Moreover, the addition of 30 µM of unlabeled 27-mer competed with the TAMRA-27-mer for binding to Gαq leading to an approximately 50 percent decrease in fluorescence polarization. This result indicates that experimentally reasonable concentrations of a small molecule inhibitor should be readily identifiable in this assay format.

Finally, the miniaturized assay consumes relatively little protein per well, enabling the screening of large libraries of compounds. For example, each 25 µL well contains 1.5 µM of Gαq/i purified after overexpression in E. coli with a yield of approximately 2 milligrams of pure protein per liter of culture. Using this concentration of Gαq/i, it would take approximately 150 milligrams of Gαq/i to undertake a screen of 100,000 compounds. The growth of 75 liters of E. coli is not impractical with current resources. With optimization of the heterologous overexpression of Gαq/i, at least a 2-fold increase in protein yield is expected upon optimization of growth and induction conditions including the use of a batch-driven, 14-liter fermenter available through the Center of Structural Biology at UNC. Amounts of TAMRA-27-mer are not an issue, it is calculated that a full screen of 100,000 compounds would consume less than two milligrams of TAMRA-27-mer in the current assay format (200 nM TAMRA-27-mer). A typical synthesis of purified TAMRA-27-mer yields approximately five milligrams.

Optimizing Assay Conditions

The current microtiter-based assay is robust. Nevertheless, several experimental variables will be optimized to facilitate high-throughput screening of compound libraries. For example, a collection of 100,000 compounds housed within the Center for Integrative Chemical Biology and Drug Discovery (CICBDD) will be screened. These compounds are stored at 10 mM in 100 percent DMSO and initially will be screened at a final concentration of 10 µM in one percent DMSO to promote compound solubility. While it is known that Gαq-GDP is stable in one percent DMSO for at least an hour and that these conditions do not affect the Z'-factor of the assay, it will be useful to define the tolerances of the assay with respect to increased incubation times and higher concentrations of DMSO. Longer incubation times and higher tolerable concentrations of DMSO will allow more flexibility in designing workflows and screening protocols during high-throughput screens that require additional handling times or higher concentrations of compounds, e.g., dose-response curves of putative inhibitors. Consequently, the performance of the assay will be assessed for up to 4 hours with concentrations of DMSO ranging from one to five percent. Similarly, a low concentration of bovine serum albumin is typically added to prevent non-specific adsorption of tested proteins to plastic ware and a low concentration of detergent is typically added to prevent the non-specific clustering of compounds into microscopic aggregates that can subsequently act to denature tested proteins and lead to the identification of false inhibitors[20]. The assay format will also be optimized to include both 0.01-0.05% (w/v) BSA and 0.01-0.1% (w/v) Triton-X-100 or CHAPS. Studies will also be carried out to investigate the use of constitutively active Gαq(Q209L) as a replacement for Gαq-GDP with aluminum fluoride.

Validate Assay Reproducibility and Workflow

After assay optimization, the assay will be validated for reproducibility and preliminary hit rate. Initial validation will entail measuring the Z'-factor derived from the fluorescence polarization of TAMRA-27-mer in the presence and absence of active Gαq under final assay conditions for sets of three plates for three days. The Z'-factor is expected to remain constant during this period and the coefficient of variance per plate should be less than 10 percent. Also, there should be no visible trends or patterns including drift or effects dependent on position within the plate, e.g., edge effects. Once these requirements are met, the assay will be used to screen in duplicate the 1280 compounds within, for example, the Library of Pharmacologically Active Compounds (LOPAC) (Sigma-Aldrich). The correlation coefficient between the two sets of data will need to be above 0.9 before continuing with further screens. These screens will also produce an initial estimate of the hit rate.

Implementation of High-Throughput Screens

Figure 5:
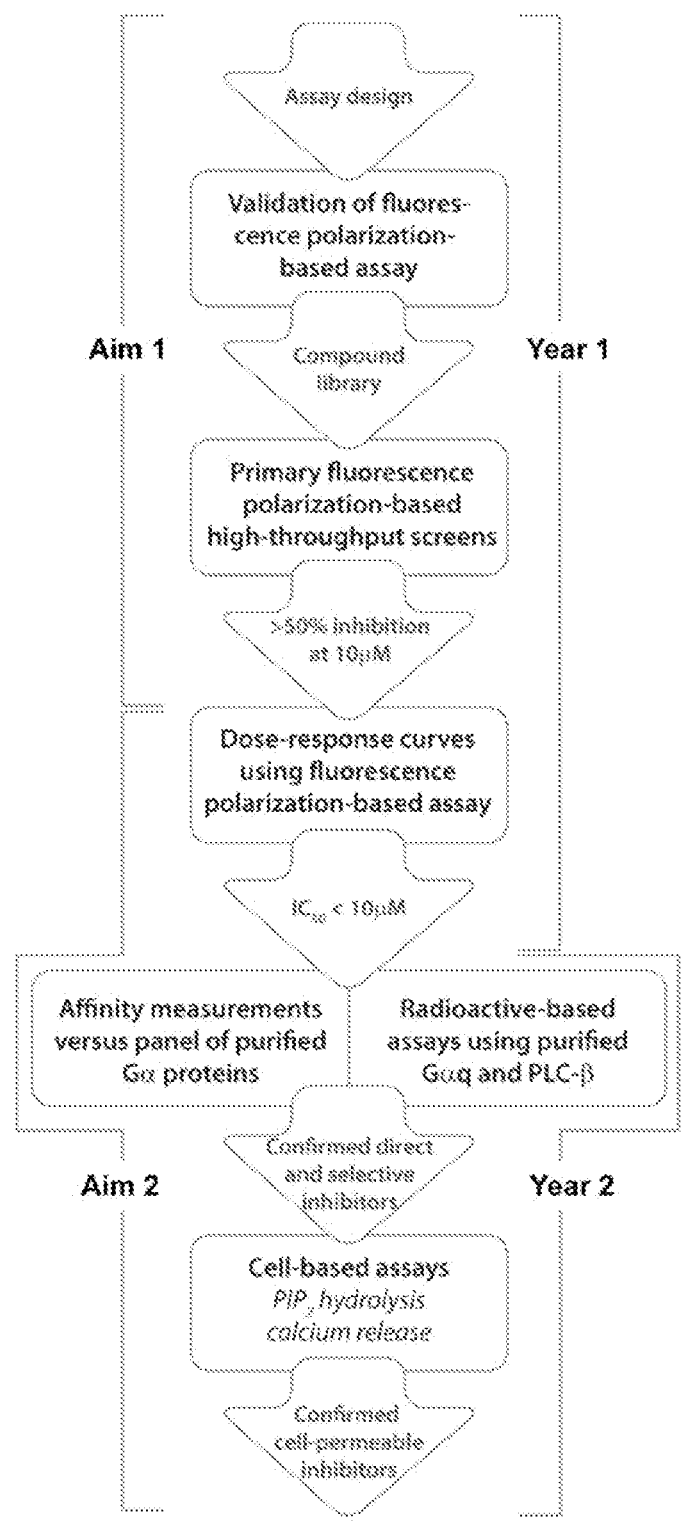
FIG. 5. Proposed workflow for high-throughput screening for inhibitors of activated Gαq.

Following validation, the final high-throughput assay and workflow will be used to screen the 100K collection of compounds maintained by the Center for Integrative Chemical Biology and Drug Discovery at UNC for inhibitors of active Gαq (FIG. 5). This collection is designed to include a maximum diversity of Murko scaffolds[21] and to eliminate toxic and reactive functional groups. Compounds (10 µM) will be tested in a single replicate and those that reduce the fluorescence polarization by at least three standard deviations relative to the uninhibited controls will be flagged as putative inhibitors of Gαq and carried forward for hit confirmation.

Validation of the Inhibitory Potentials, Selectivity Profiles, and Cellular Activities of Small Molecules Identified as Inhibitors of Activated Gαq.

It will be sought to identify 100 putative inhibitors of activated Gαq from the initial screen of 100K compounds for a hit rate of 0.1 percent. If the original conditions produce more than 100 putative inhibitors the stringency of the cutoff will be increased to include only the top 100 candidates for subsequent analysis. Conversely, if the original conditions produce fewer than 20 hits, the stringency of the cutoff will be decreased to two standard deviations relative to the uninhibited controls. In the event that fewer than 5 hits are obtained, the compounds within the 100K library will be rescreened at 50 µM.

The set of putative inhibitors will be extracted from the mother plates and used to measure dose-response curves of Gαq inhibition to yield inhibitor concentrations that produce 50% of the maximal inhibition ($IC_{50}$ values).

Verification of Initial Hits Using Established Secondary Assays

Inhibitors with $IC_{50}$ values less than 10 µM will be tested in a secondary assay to: i) verify capacity to inhibit Gαq and ii) confirm the selectivity of inhibition.

Screens based on fluorescence polarization typically have less artifacts than assays based on other types of fluorescence measurements[22], nevertheless, some compounds in the initial high-throughput screen are likely to affect fluorescence, leading to their inappropriate identification as inhibitors of Gαq. Consequently, a conventional radioactive-based assay will be used to eliminate hits that are false positives and confirm the inhibitory potentials of the remaining active compounds. In this case, purified Gαq and PLC-β3 will be reconstituted in lipid vesicles containing radioactive $PIP_2$ and amounts of $PIP_2$ hydrolyzed upon Gαq activation with aluminum fluoride will be measured. This format is routinely used to understand the regulation of PLCs[11] and is shown in FIG. 3B. Additions of bona fide inhibitors of Gαq prior to its activation are expected to reduce the hydrolysis of $PIP_2$ relative to equivalent reactions without compound addition. Alternatively, false positives from the original screen are unlikely to prevent PIP$_2$ hydrolysis and will be eliminated from further analyses. It is also possible that some compounds might affect the integrity of the lipid vesicles needed for efficient activation of PLC-β3 by Gαq. These compounds would erroneously appear as inhibitors of Gαq. They will be eliminated by testing the activation of PLC-β3 by Gβγ in lipid vesicles under identical conditions. Like Gαq, Gβγ also requires intact vesicles for efficient activation of PLC-β isozymes and compounds that inhibited the activation of PLC-β3 by both Gαq and Gβγ would not be considered further. Compounds will be tested in triplicate at 10 and 100 μM and IC$_{50}$ values of confirmed inhibitors will be measured using the radioactive-based assay to measure dose-response curves; these IC$_{50}$ values should correspond closely to the equivalent IC$_{50}$ values measured using fluorescence polarization.

Quantifying Inhibitory Potentials in Cell-Based Assays

The previous assays are designed to identify compounds that directly, selectively, and potently inhibit the capacity of active Gαq to engage downstream effectors using purified proteins and reconstituted systems. Here, two sets of complementary experiments will be used to test the identified compounds for capacity to enter cells and inhibit active Gαq as monitored by phospholipase activity.

In the first case, compounds will be tested for capacity to prevent the enhanced phospholipase activity of PLC-β3 in response to active Gαq using a scintillation proximity assay previously described[23,24]. As an example, HEK-293 cells will be grown in 48-well microtiter plates prior to transfection with expressions plasmids encoding Gαq and PLC-β3. Cells will subsequently be metabolically labeled with myo-[2-$^3$H(N)]inositol and treated with individual compounds (100 μM in triplicate) shown to directly and potently inhibit Gαq using the previous assays. Length of treatment will be held short (~15 minutes) to allow compound entry into cells and potential inhibition of Gαq while simultaneously avoiding secondary cellular responses, e.g., detachment of cells from the plate or apoptosis that would complicate the assay. After treatment, carbachol will be added for 15 minutes to activate endogenous muscarinic receptors coupled to Gαq followed by cell lysis and quantification of [$^3$H]-inositol phosphates by scintillation counting after capture using a commercial resin composed of yttrium silicate. Cell-permeable and metabolically stable inhibitors of active Gαq are expected to decrease levels of [$^3$H]-inositol phosphates.

A common assay to monitor the activation of PLCs downstream of Gαq is to monitor calcium release from intracellular stores using calcium-sensitive, fluorescence-based dyes[25]. Accordingly, compounds identified previously as direct and specific inhibitors of Gαq will be tested for modulation of calcium release upon activation of the Gαq-coupled P2Y6 receptor stably expressed in 1321N1 astrocytoma cells using standard methodology[26]; increasing concentrations of efficacious inhibitors will reduce calcium flux from intracellular stores.

Compounds that bind and inhibit purified Gαq but cannot inhibit Gαq in cells will be assumed to have poor potential to enter cells or otherwise fail to target cellular Gαq due to unknown reasons, e.g., metabolism. These compounds are useful as leads, but derivatives will be needed to increase bioavailability. The most promising leads are those compounds that produce similar effects in both in vitro and cellular formats.

Interdicting Gαq Signaling in Uveal Melanomas

The lead compounds with the highest potency to inhibit Gαq in the previous cellular assays will be assessed for the capacity to inhibit constitutively active Gαq(Q209L) in uveal melanoma cell lines (OMM1.3 and Mel202). These cell lines were used previously to demonstrate that siRNA-mediated knock-down of Gαq decreased signaling through the MAPK cascade with a concomitant reduction of anchorage-independent growth[3]. These cell lines will be used to test high potency leads for capacity to prevent the activation of the MAPK cascade downstream of active Gαq as assessed by levels of ERK phosphorylation and amounts of cyclin D[3,27]. Compounds that efficiently enter cells and inhibit Gαq should decrease both ERK phosphorylation and cyclin D.

Perspectives for Treating Ocular Melanoma

Constitutively active Gαq is found in ~50% of uveal melanomas where it drives MAPK activation and supports tumorigenesis. Uveal melanoma is the most prevalent intraocular cancer, representing 5-6% of all melanoma diagnoses and affecting ~1,500 people each year in North America[28,29,30]. A patient diagnosed with uveal melanoma has few treatment options, mainly limited to radiography or removal of the eye. Once metastasis has occurred, affected patients have short life expectancies of usually six to eight months[29,31]. Small molecule inhibitors of active Gαq that could potentially be used to treat ocular melanoma are lacking. The studies described herein will identify selective and potent inhibitors of Gαq useful to treat ocular melanomas.

REFERENCES

1. Singh, A. D., Bergman, L. & Seregard, S. (2005). Uveal melanoma: epidemiologic aspects. *Ophthalmol Clin North Am* 18, 75-84, viii.
2. Singh, A. D. & Topham, A. (2003). Survival rates with uveal melanoma in the United States: 1973-1997. *Ophthalmology* 110, 962-5.
3. Van Raamsdonk, C. D., Bezrookove, V., Green, G., Bauer, J., Gaugler, L., O'Brien, J. M., et al. (2009). Frequent somatic mutations of GNAQ in uveal melanoma and blue naevi. *Nature* 457, 599-602.
4. Populo, H., Vinagre, J., Lopes, J. M. & Soares, P. (2011). Analysis of GNAQ mutations, proliferation and MAPK pathway activation in uveal melanomas. *Br J Ophthalmol* 95, 715-9.
5. Seo, B., Choy, E. W., Maudsley, S., Miller, W. E., Wilson, B. A. & Luttrell, L. M. (2000). Pasteurella multocida toxin stimulates mitogen-activated protein kinase via G(q/11)-dependent transactivation of the epidermal growth factor receptor. *J Biol Chem* 275, 2239-45.
6. Hawes, B. E., van Biesen, T., Koch, W. J., Luttrell, L. M. & Lefkowitz, R. J. (1995). Distinct pathways of Gi- and Gq-mediated mitogen-activated protein kinase activation. *J Biol Chem* 270, 17148-53.
7. Rojas, R. J., Yohe, M. E., Gershburg, S., Kawano, T., Kozasa, T. & Sondek, J. (2007). Gαq directly activates p63RhoGEF and Trio via a conserved extension of the Dbl homology-associated pleckstrin homology domain. *J Biol Chem* 282, 29201-10.
8. Sah, V. P., Hoshijima, M., Chien, K. R. & Brown, J. H. (1996). Rho is required for Galphaq and alpha1-adrenergic receptor signaling in cardiomyocytes. Dissociation of Ras and Rho pathways. *J Biol Chem* 271, 31185-90.
9. Fritz, G., Just, I. & Kaina, B. (1999). Rho GTPases are over-expressed in human tumors. *Int J Cancer* 81, 682-7.
10. Rathinam, R., Berrier, A. & Alahari, S. K. Role of Rho GTPases and their regulators in cancer progression. *Front Biosci* 17, 2561-71.

11. Waldo, G. L., Ricks, T. K., Hicks, S. N., Cheever, M. L., Kawano, T., Tsuboi, K., et al. (2010). Kinetic scaffolding mediated by a phospholipase C-b and Gq signaling complex. *Science* 330, 974-80.
12. Fecher, L. A., Amaravadi, R. K. & Flaherty, K. T. (2008). The MAPK pathway in melanoma. *Curr Opin Oncol* 20, 183-9.
13. Haluska, F. G. & Ibrahim, N. (2006). Therapeutic targets in melanoma: map kinase pathway. *Curr Oncol Rep* 8, 400-5.
14. Thomas, N. E. (2006). BRAF somatic mutations in malignant melanoma and melanocytic naevi. *Melanoma Res* 16, 97-103.
15. Inamdar, Q. S., Madhunapantula, S. V. & Robertson, G. P. (2010). Targeting the MAPK pathway in melanoma: why some approaches succeed and other fail. *Biochem Pharmacol* 80, 624-37.
16. Romano, E., Schwartz, G. K., Chapman, P. B., Wolchock, J. D. & Carvajal, R. D. (2011). Treatment implications of the emerging molecular classification system for melanoma. *Lancet Oncol* 12, 913-22.
17. Van Raamsdonk, C. D., Griewank, K. G., Crosby, M. B., Garrido, M. C., Vemula, S., Wiesner, T., et al. (2010). Mutations in GNA11 in uveal melanoma. *N Engl J Med* 363, 2191-9.
18. Lutz, S., Shankaranarayanan, A., Coco, C., Ridilla, M., Nance, M. R., Vettel, C., et al. (2007). Structure of $Ga_q$-p63RhoGEF-RhoA complex reveals a pathway for the activation of RhoA by GPCRs. *Science* 318, 1923-7.
19. Zhang, J. H., Chung, T. D. & Oldenburg, K. R. (1999). A Simple Statistical Parameter for Use in Evaluation and Validation of High Throughput Screening Assays. *J Biomol Screen* 4, 67-73.
20. Janzen, W. P. & Bernasconi, P. (2009). High throughput screening. Methods and protocols, second edition. Preface. *Methods Mol Biol* 565, v-vii.
21. Bemis, G. W. & Murcko, M. A. (1996). The properties of known drugs. 1. Molecular frameworks. *J Med Chem* 39, 2887-93.
22. Owicki, J. C. (2000). Fluorescence polarization and anisotropy in high throughput screening: perspectives and primer. *J Biomol Screen* 5, 297-306.
23. Bourdon, D. M., Wing, M. R., Edwards, E. B., Sondek, J. & Harden, T. K. (2006). Quantification of isozyme-specific activation of phospholipase C-beta2 by Rac GTPases and phospholipase C-epsilon by Rho GTPases in an intact cell assay system. *Methods Enzymol* 406, 489-99.
24. Bembenek, M. E., Jain, S., Prack, A., Li, P., Chee, L., Cao, W., et al. (2003). Development of a high-throughput assay for two inositol-specific phospholipase Cs using a scintillation proximity format. *Assay Drug Dev Technol* 1, 435-43.
25. Gee, K. R., Brown, K. A., Chen, W. N., Bishop-Stewart, J., Gray, D. & Johnson, I. (2000). Chemical and physiological characterization of fluo-4 Ca(2+)-indicator dyes. *Cell Calcium* 27, 97-106.
26. Nicholas, R. A., Lazarowski, E. R., Watt, W. C., Li, Q., Boyer, J. & Harden, T. K. (1996). Pharmacological and second messenger signalling selectivities of cloned P2Y receptors. *J Auton Pharmacol* 16, 319-23.
27. Shields, J. M., Thomas, N. E., Cregger, M., Berger, A. J., Leslie, M., Torrice, C., et al. (2007). Lack of extracellular signal-regulated kinase mitogen-activated protein kinase signaling shows a new type of melanoma. *Cancer Res* 67, 1502-12.
28. Singh, A. D., Wang, M. X., Donoso, L. A., Shields, C. L., De Potter, P. & Shields, J. A. (1996). Genetic aspects of uveal melanoma: a brief review. *Semin Oncol* 23, 768-72.
29. Bedikian, A. Y. (2006). Metastatic uveal melanoma therapy: current options. *Int Ophthalmol Clin* 46, 151-66.
30. Egan, K. M., Seddon, J. M., Glynn, R. J., Gragoudas, E. S. & Albert, D. M. (1988). Epidemiologic aspects of uveal melanoma. *Surv Ophthalmol* 32, 239-51.
31. Shields, C. L. & Shields, J. A. (2009). Ocular melanoma: relatively rare but requiring respect. *Clin Dermatol* 27, 122-33.

Example 3

The majority of uveal melanomas have mutated G-alpha-q that is constitutively active. G-alpha-q directly activates the phospholipase C beta isoforms (PLC-beta1-4) to catalyze the hydrolysis of phosphatidylinositol 4,5-bisphosphate ($PIP_2$) into the second messengers, inositol trisphosphate ($IP_3$) and diacylglycerol (DAG). These second messengers mobilize intracellular calcium stores and activate protein kinase C (PKC) to promote cell proliferation. Peptidomimetics are designed and optimized that directly and potently compete with endogenous effectors for binding to G-alpha-q with the ultimate goal of using these reagents to inhibit the transforming potential of constitutively active G-alpha-q in uveal melanomas. A high-throughput assay has also been developed to identify small molecule inhibitors of signaling by G-alpha-q as an additional approach to identify lead compounds for the eventual treatment of uveal melanomas, and possibly other cancers.

Recent structures of G-alpha-q bound to either PLC-beta or p63RhoGEF highlight an essentially identical mechanism of effector engagement; the canonical effector-binding site of G-alpha-q is occupied by a helix-turn-helix (HTH) of either PLC-beta3 or p63RhoGEF. These helices are assumed to be relatively mobile prior to complex formation with transient secondary structure induced by the complex. It has been shown that peptides corresponding to the HTH of these effectors inhibit the capacity of G-alpha-q to engage effectors and that related peptides with increased helical propensity will be useful as high-affinity probes and pre-therapeutic leads to examine G-alpha-q-mediated signaling in cells.

Initially, TAMRA-labeled peptides spanning the HTH of PLC-beta3 were synthesized and tested for binding to G-alpha-q using fluorescence polarization. The most promising peptide consisted of 25 residues (TAMRA-25-mer) spanning the entire HTH and bound to G-alpha-q with appreciable affinity (Kd~6 microMolar). The complex was dependent on the activation of G-alpha-q with aluminum fluoride and was specific since additional, active G-alpha proteins (G-alpha-s, G-alpha-i and G-alpha-o) failed to bind the peptide. Moreover, full-length PLC-beta3 inhibited TAMRA-25-mer binding to G-alpha-q (IC50~1 microMolar), whereas a mutant PLC-beta3(L859E) that does not bind G-alpha-q had no effect at concentrations as high as 35 microMolar. Since full-length PLC-beta3 binds activated G-alpha-q with a dissociation constant (Kd) of approximately 10-100 nM, these results indicate that the 25-mer retains the majority of determinants for binding to G-alpha-q.

These results indicate that this peptide should also prevent the capacity of G-alpha-q to activate PLC-beta3. To address this, purified G-alpha-q and PLC-beta3 proteins were reconstituted with lipid vesicles and phospholipase activity was measured as a function of increasing concentrations of TAMRA-25-mer before and after activation of G-alpha-q with aluminum fluoride. The peptide inhibited phospholipase activity with low micromolar potency ($IC_{50} \sim 1$ microMolar) consistent with its affinity for G-alpha-q. Full-length PLC-beta3 harboring a substitution of alanine for isoleucine at position 860 (I860A) within its HTH was more responsive to G-alpha-q than its wild-type counterpart, suggesting that this mutation increased affinity of PLC-beta3 for G-alpha-q. Indeed, a peptide corresponding to the HTH of PLC-beta3 and containing this substitution dramatically enhanced the inhibitory potential relative to the 25-mer peptide. The corresponding $IC_{50}$ was approximately 100 nM suggesting that this peptide is an excellent scaffold for designing peptidomimetics to inhibit constitutively active G-alpha-q in cells.

Since a major tenet of this work is to downregulate G-alpha-q signaling in cells with peptidomimetics, peptides derived from this scaffold have been efficiently delivered into cells. As a first step in this process, a lipid-peptide corresponding to the HTH of PLC-beta3 is shown to prevent the stimulation of PLC activity by G-alpha-q downstream of the muscarinic receptors, a G protein-coupled receptor selective for G-alpha-q.

Furthermore, a fluorescently labeled 25-mer peptide containing the I860A mutation is used to screen for small molecules that inhibit the interaction between G-alpha-q and its effectors. A high-throughput assay was created that monitors effector binding to G-alpha-q and plan to screen large libraries (>100,000 compounds) of low molecular weight compounds to identify inhibitors of signaling by G-alpha-q. Initial hits will be verified with purified proteins in the lipid assay described herein. Cellular assays will be tested as described above to demonstrate effective dampening of PLC activity by lead hits.

Example 4

Figure 10:
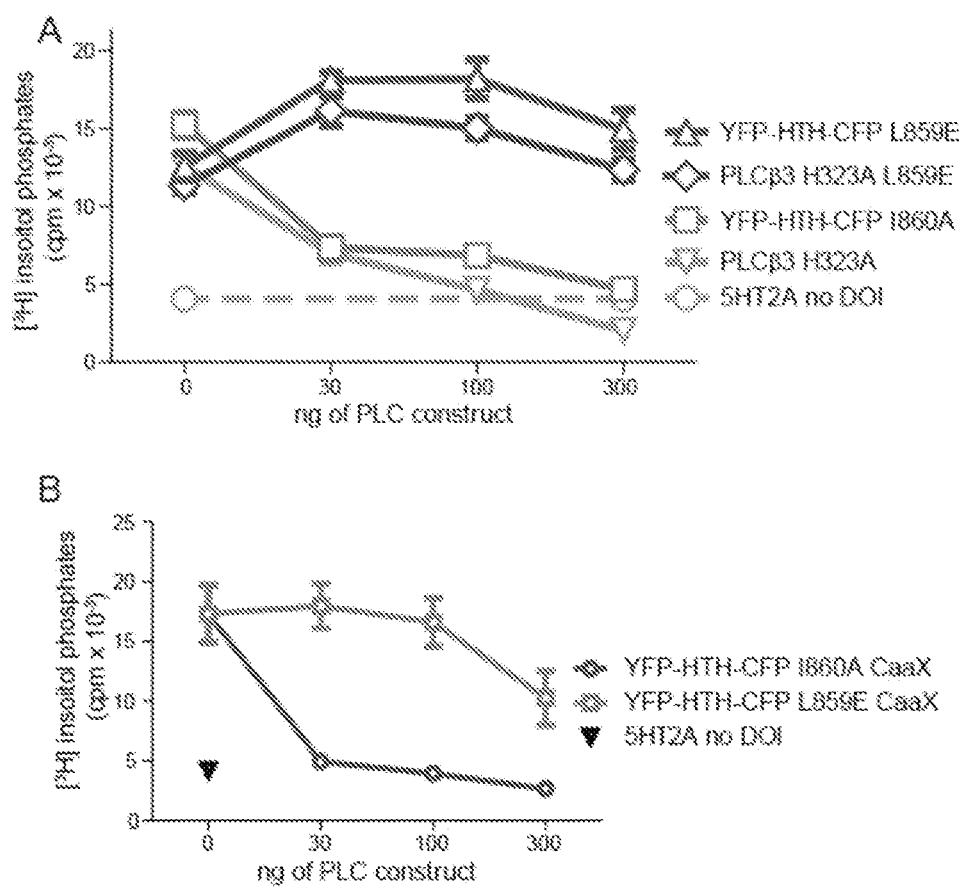
FIG. 10. Transient transfection of CFP-27mer(I860A)-YFP inhibits G-alpha-q mediated activation of PLC-beta in HEK293 cells. HEK293 cells transfected with 100 ng of 5HT2A and stimulated with 1-2 microMolar of DOI (Synonym: (±)-DOI, (±)-1-(2,5-Dimethoxy-4-iodophenyl)-2-aminopropane hydrochloride, (±)-2,5-Dimethoxy-4-iodo-amphetamine hydrochloride) were assayed for [$^3$H]inositol phosphate accumulation. The control for no DOI stimulation for the CFP-HTH-YFP sample is shown as dashed line (A) and triangle (B). Where indicated HEK293 cells were transfected with varying amounts of PLC constructs.

The 27 residue helix-turn-helix peptide was transiently transfected into HEK293 cells and inhibited G-alpha-q signaling (FIG. 10). This experiment is a proof of principle to inhibit G-alpha-q with adeno-associated virus (AAV) to treat uveal melanoma patients. Future experiments will use a retrovirus containing the 27 residue helix-turn-helix in primary uveal melanoma cells to induce apoptosis and inhibit the progression of the uveal melanoma.

The 27mer construct used is between two fluorescent proteins YFP and CFP yielding: YFP-HTH(27mer)-CFP. The 27mer sequence is

```
                                          (SEQ ID NO: 35)
HQDYAEALANPIKHVSLMDQRARQLAA
```

A CaaX box was attached to the YFP-HTH(27mer)-CFP to keep this molecule at the membrane. The CaaX box sequence is at the very C-terminal end and are the residues CAIL (SEQ ID NO:36).

All publications, patent applications, patents, patent publications and other references cited herein are incorporated by reference in their entireties for the teachings relevant to the sentence and/or paragraph in which the reference is presented.

The foregoing examples are illustrative of the present invention, and are not to be construed as limiting thereof. The invention is described by the following claims, with equivalents of the claims to be included therein.

TABLE 1

| Modified Amino Acid Residue | Abbreviation |
| --- | --- |
| Amino Acid Residue Derivatives | |
| (R)-(+)-α-Allylalanine | C6H11NO2 |
| (S)-(−)-α-Allylalanine | C6H11NO2 |
| D-2-Aminobutyric acid | C4H9NO2 |
| L-2-Aminobutyric acid | C4H9NO2 |
| DL-2-Aminobutyric acid | C4H9NO2 |
| DL-2-Aminobutyric acid | C4H9NO2 |
| 2-Aminoisobutyric acid | C4H9NO2 |
| α-Aminoisobutyric acid | C4H9NO2 |
| (S)-(+)-2-Amino-4-phenylbutyric acid | |
| Benzyl α-aminoisobutyrate | |
| Abu-OH | |
| D-Abu-OH | |
| Aib-OH | |
| β-(9-anthryl)-Ala-OH | |
| β-(3-benzothienyl)-Ala-OH | |
| β-(3-benzothienyl)-D-Ala-OH | |
| Cha-OH | |
| D-Cha-OH | |
| β-(2-furyl)-Ala-OH | |
| β-(2-furyl)-D-Ala-OH | |
| β-iodo-Ala-OH | |
| β-iodo-D-Ala-OH | |
| 3-iodo-D-Ala-OH | |
| β-iodo-Ala-OH | |
| 1-Nal-OH | |
| D-1-Nal-OH | |
| 2-Nal-OH | |
| D-2-Nal-OH | |
| (R)-3-(2-naphthyl)-β-Ala-OH | |
| (S)-3-(2-naphthyl)-β-Ala-OH | |
| β-phenyl-Phe-OH | |
| 3-(2-pyridyl)-Ala-OH | |
| 3-(3-pyridyl)-Ala-OH | |
| 3-(3-pyridyl)-D-Ala-OH | |
| (S)-3-(3-pyridyl)-β-Ala-OH | |
| 3-(4-pyridyl)-Ala-OH | |
| 3-(4-pyridyl)-D-Ala-OH | |
| β-(2-quinolyl)-Ala-OH | |
| 3-(2-quinolyl)-DL-Ala-OH | |
| 3-(3-quinolyl)-DL-Ala-OH | |
| 3-(2-quinoxalyl)-DL-Ala-OH | |
| β-(4-thiazolyl)-Ala-OH | |
| β-(2-thienyl)-Ala-OH | |
| β-(2-thienyl)-D-Ala-OH | |
| β-(3-thienyl)-Ala-OH | |
| β-(3-thienyl)-D-Ala-OH | |
| 3-(2-naphthyl)-L-alanine | |
| 3-Cyclohexyl-D-alanine | |
| 3-Cyclopentyl-DL-alanine | C8H15NO2 |
| (−)-3-(3,4-Dihydroxyphenyl)-2-methyl-L-alanine | |
| 3,3-Diphenyl-D-alanine | C15H15NO2 |
| 3,3-Diphenyl-L-alanine | C15H15NO2 |
| N-[(S)-(+)-1-(Ethoxycarbonyl)-3-phenylpropyl]-L-alanine | C15H21NO4 |
| N-[1-(S)-(+)-Ethoxycarbonyl-3-phenylpropyl]-L-alanyl carboxyanhydride | C16H19NO5 |
| Abu-OH | |
| 3-(9-anthryl)-Ala-OH | |
| β-azido-Ala-OH | |
| Cha-OH | |
| D-Cha-OH | |
| 3-cyclopentyl-DL-Ala-OH | |
| β-(2-furyl)-Ala-OH | |
| β-(2-furyl)-D-Ala-OH | |
| α-Me-Ala-OH | |
| 1-Nal-OH | |
| D-1-Nal-OH | |
| 2-Nal-OH | |
| D-2-Nal-OH | |
| β-phenyl-Phe-OH | |
| 3-(1-pyrazolyl)-Ala-OH | |
| β-(2-pyridyl)-Ala-OH | |
| β-(2-pyridyl)-D-Ala-OH | |
| β-(3-pyridyl)-Ala-OH | |
| β-(3-pyridyl)-D-Ala-OH | |
| β-(4-pyridyl)-Ala-OH | |

TABLE 1-continued

| Modified Amino Acid Residue | Abbreviation |
|---|---|
| β-(4-pyridyl)-D-Ala-OH | |
| 3-(2-quinolyl)-DL-Ala-OH | |
| β-styryl-D-Ala-OH | |
| β-(4-thiazolyl)-Ala-OH | |
| β-(2-thienyl)-Ala-OH | |
| β-(3-thienyl)-Ala-OH | |
| β-(3-thienyl)-D-Ala-OH | |
| 3-(1,2,4-triazol-1-yl)-Ala-OH | |
| N-(3-Indolylacetyl)-L-alanine | C13H14N2O3 |
| Methyl (RS)-2-(aminomethyl)-3-phenylpropionate | |
| 3-(2-Oxo-1,2-dihydro-4-quinolinyl)alanine | |
| 3-(1-Pyrazolyl)-L-alanine | C6H9N3O2 |
| 3-(2-Pyridyl)-D-alanine | C8H10N2O2 |
| 3-(2-Pyridyl)-L-alanine | C8H10N2O2 |
| 3-(3-Pyridyl)-L-alanine | C8H10N2O2 |
| 3-(4-Pyridyl)-D-alanine | C8H10N2O2 |
| 3-(4-Pyridyl)-L-alanine | C8H10N2O2 |
| 3-(2-Quinolyl)-DL-alanine | C12H12N2O2 |
| 3-(4-Quinolyl)-DL-alanine | |
| 3-(2-Tetrazolyl)-L-alanine | C4H7N5O2 |
| 3-(2-Thienyl)-L-alanine | C7H9NO2S |
| 3-(2-Thienyl)-DL-alanine | C7H9NO2S |
| 3-(2-Thienyl)-DL-alanine | C7H9NO2S |
| 3-(1,2,4-Triazol-1-yl)-L-alanine | C5H8N4O2 |
| 3,3,3-Trifluoro-DL-alanine | C3H4F3NO2 |
| 3-Ureidopropionic acid | C4H8N2O3 |
| Aib-OH | |
| Cha-OH | |
| Dehydro-Ala-OH | |
| D-2-Nal-OH | |
| (cis)-3-Aminobicyclo[2.2.1]heptane-2-carboxylic acid | |
| exo-cis-3-Aminobicyclo[2.2.1]hept-5-ene-2-carboxylic acid | |
| 1-Amino-1-cyclobutanecarboxylic acid | C5H9NO2 |
| cis-2-Aminocycloheptanecarboxylic acid | C8H15NO2 |
| 1-Aminocyclohexanecarboxylic acid | C7H13NO2 |
| cis-2-Aminocyclohexanecarboxylic acid | C7H13NO2 |
| trans-2-Aminocyclohexanecarboxylic acid | C7H13NO2 |
| cis-2-Amino-3-cyclohexene-1-carboxylic acid | C7H11NO2 |
| cis-6-Amino-3-cyclohexene-1-carboxylic acid | C7H11NO2 |
| 2-(1-Aminocyclohexyl)acetic acid | C8H15NO2 |
| cis-2-Amino-1-cyclooctanecarboxylic acid | C9H17NO2 |
| cis-2-Amino-3-cyclooctene-1-carboxylic acid | C9H15NO2 |
| cis-2-Amino-1-cyclopentanecarboxylic acid | C6H11NO2 |
| 2-(1-Aminocyclopentyl)acetic acid | C7H13NO2 |
| cis-2-Amino-2-methylcyclohexanecarboxylic acid | C8H15NO2 |
| cis-2-Amino-2-methylcyclopentanecarboxylic acid | C7H13NO2 |
| 3-Amino-3-(4-nitrophenyl)propionic acid | C9H10N2O4 |
| 3-Azetidinecarboxylic acid | C4H7NO2 |
| 1-aminocyclobutane carboxylic acid | |
| 1-aminocyclohexanecarboxylic acid | |
| cis-2-aminocyclohexanecarboxylic acid | |
| trans-2-aminocyclohexanecarboxylic acid | |
| cis-4-aminocyclohexanecarboxylic acid | |
| trans-4-aminocyclohexanecarboxylic acid | |
| (±)-cis-2-amino-3-cyclohexene-1-carboxylic acid | |
| (±)-cis-6-amino-3-cyclohexene-1-carboxylic acid | |
| 2-(1-aminocyclohexyl)acetic acid | |
| cis-[4-aminocyclohexyl]acetic acid | |
| 1-aminocyclopentanecarboxylic acid | |
| (±)-cis-2-aminocyclopentanecarboxylic acid | |
| (1R,4S)-(+)-4-amino-2-cyclopentene-1-carboxylic acid | |
| (1S,4R)-(−)-4-amino-2-cyclopentene-1-carboxylic acid | |
| (±)-cis-2-amino-3-cyclopentene-1-carboxylic acid | |
| 2-(1-aminocyclopentyl)acetic acid | |
| 1-aminocyclopropanecarboxylic acid | |
| 1-aminocyclobutanecarboxylic acid | |
| 1-aminocyclohexanecarboxylic acid | |
| cis-2-amino-cyclohexanecarboxylic acid | |
| trans-2-aminocyclohexanecarboxylic acid | |
| cis-4-aminocyclohexanecarboxylic acid | |
| trans-4-aminocyclohexanecarboxylic acid | |
| cis-[4-aminocyclohexyl]acetic acid | |
| 1-aminocyclopentanecarboxylic acid | |
| (1R,4S)-(+)-4-amino-2-cyclopentene-1-carboxylic acid | |
| (1S,4R)-(−)-4-amino-2-cyclopentene-1-carboxylic acid | |
| 1-aminocyclopropanecarboxylic acid | |
| trans-4-aminomethylcyclohexanecarboxylic acid | |
| 1-(Z-amino)cyclobutanecarboxylic acid | C13H15NO4 |
| L-2-Amino-3-guanidinopropionic acid | C4H10N4O2 |
| L-2-Amino-3-guanidinopropionic acid | C4H10N4O2 |
| 4-Guanidinobutyric acid | C5H11N3O |
| 3-Guanidinopropionic acid | C4H9N3O2 |
| NωNitro-L-arginine | |
| Asn(Xan)-OH | |
| Nβ-xanthenyl-L-asparagine | |
| (S)-(−)-4-tert-Butyl hydrogen 2-azidosuccinate | |
| L-aspartic anhydride | |
| L-Cysteic acid | C3H7NO5S |
| L-Cysteinesulfinic acid | C3H7NO4S |
| D-Ethionine | C6H13NO2S |
| Cys(methyl)-OH | |
| Seleno-L-cystine | C6H12N2O4Se2 |
| S-(2-Thiazolyl)-L-cysteine | C6H8N2O2S2 |
| S-(2-Thienyl)-L-cysteine | C7H9NO2S2 |
| S-(4-Tolyl)-L-cysteine | C10H13NO2S |
| Dab-OH | |
| L-2,4-Diaminobutyric acid | C4H10N2O2 |
| Dab-OH | |
| D-2,3-Diaminopropionic acid | C3H8N2O2 |
| L-2,3-Diaminopropionic acid | C3H8N2O2 |
| DL-2,3-Diaminopropionic acid | C3H8N2O2 |
| Dap-OH | |
| D-Dap-OH | C11H14N2O4 |
| D-2-Aminoadipic acid | C6H11NO4 |
| (S)-5-tert-Butyl hydrogen 2-azidoglutarate | |
| γ-Crboxy-DL-glutamic acid | C6H9NO6 |
| 4-Fluoro-DL-glutamic acid | C5H8FNO4 |
| Cit-OH | |
| D-Citrulline | C6H13N3O3 |
| 3-(3-methyl-4-nitrobenzyl)-L-histidine | |
| (R)-2-amino-5-hexynoic acid | |
| Homophe-OH | |
| D-Homophe-OH | |
| β-Homopyr-OH | |
| Homophe-OH | |
| D-Homophe-OH | |
| Homoser-OH | |
| D-Homoser-OH | |
| piperidine-2-carboxylic acid | |
| L-Homoarginine | C7H16N4O2 |
| DL-Homocysteine | C4H9NO2S |
| L-Homocysteine thiolactone | C4H7NOS |
| L-Homocysteine thiolactone | C4H7NOS |
| L-Homocystine | C8H16N2O4S2 |
| D-Homophenylalanine | C10H13NO2 |
| L-Homophenylalanine | C10H13NO2 |
| DL-Homophenylalanine | C10H13NO2 |
| D-Homophenylalanine | |
| D-Homoserine | C4H9NO3 |
| L-Homoserine | C4H9NO3 |
| L-homoserine | |
| Z-Homophe-OH | C18H19NO4 |
| L-Homoserine lactone | |
| allo-Ile-OH | |
| D-allo-Isoleucine | C6H13NO2 |
| D-allo-Isoleucine | C6H13NO2 |
| DL-allo-Isoleucine | C6H13NO2 |
| N-[(2S,3R)-3-Amino-2-hydroxy-4-phenylbutyryl]-L-leucine | C16H24N2O4 |
| 4,5-dehydro-Leu-OH | |
| Ile-OH | |
| Cycloleucine | C6H11NO2 |
| N-(3,5-Dinitrobenzoyl)-DL-leucine | C13H15N3O7 |
| Gly-OH | |
| N-(3-Indolylacetyl)-L-isoleucine | C16H20N2O3 |
| D-tert-Leucine | C6H13NO2 |
| L-tert-Leucine | C6H13NO2 |
| DL-tert-Leucine | C6H13NO2 |
| 5,5,5-Trifluoro-DL-leucine | C6H10F3NO2 |
| (S)-(−)-1-[N-(1-Ethoxycarbonyl-3-phenylpropyl)-N-trifluoroacetyl]-L-lysine | C20H27F3N2O5 |
| β-Lys-OH | |
| DL-5-Hydroxylysine | C6H14N2O3 |

TABLE 1-continued

| Modified Amino Acid Residue | Abbreviation |
| --- | --- |
| (5R)-5-Hydroxy-L-lysine | C6H14N2O3 |
| 6-azido-L-norleucine | |
| Nle-OH | |
| D-Nle-OH | |
| D-Norleucine | C6H13NO2 |
| L-Norleucine | C6H13NO2 |
| DL-Norleucine | C6H13NO2 |
| 5-azido-L-norvaline | |
| Nva-OH | |
| D-Nva-OH | |
| D-Norvaline | C5H11NO2 |
| DL-Norvaline | C5H11NO2 |
| (S)-5-Azido-2-aminopentanoic acid | |
| Orn-OH | |
| Orn(2-Cl-Z)-OH | |
| Orn-OH | |
| D-Ornithine | C5H12N2O2 |
| L-Ornithine | C5H12N2O2 |
| DL-Ornithine | C5H12N2O2 |
| 3-Acetamidobenzoic acid | C9H9NO3 |
| 4-Acetamidobenzoic acid | C9H9NO3 |
| 4-Acetamido-2-methylbenzoic acid | C10H11NO3 |
| N-Acetylanthranilic acid | C9H9NO3 |
| 3-Aminobenzoic acid | C7H7NO2 |
| 3-Aminobenzoic acid | C7H7NO2 |
| 4-Aminobenzoic acid | C7H7NO2 |
| 4-Aminobenzoic acid | C7H7NO2 |
| 4-Aminobenzoic acid | C7H7NO2 |
| 4-Aminobenzoic acid | |
| 4-Aminobenzoic acid | |
| 4-Aminobenzoic acid | |
| 2-Aminobenzophenone-2'-carboxylic acid | C14H11NO3 |
| 2-Amino-4-bromobenzoic acid | C7H6BrNO2 |
| 2-Amino-5-bromobenzoic acid | C7H6BrNO2 |
| 3-Amino-2-bromobenzoic acid | C7H6BrNO2 |
| 3-Amino-4-bromobenzoic acid | C7H6BrNO2 |
| 3-Amino-5-bromobenzoic acid | C7H6BrNO2 |
| 4-Amino-3-bromobenzoic acid | C7H6BrNO2 |
| 5-Amino-2-bromobenzoic acid | C7H6BrNO2 |
| 2-Amino-3-bromo-5-methylbenzoic acid | C8H8BrNO2 |
| 2-Amino-3-chlorobenzoic acid | C7H6ClNO2 |
| 2-Amino-4-chlorobenzoic acid | C7H6ClNO2 |
| 2-Amino-5-chlorobenzoic acid | C7H6ClNO2 |
| 2-Amino-5-chlorobenzoic acid | C7H6ClNO2 |
| 2-Amino-6-chlorobenzoic acid | C7H6ClNO2 |
| 3-Amino-2-chlorobenzoic acid | C7H6ClNO2 |
| 3-Amino-4-chlorobenzoic acid | C7H6ClNO2 |
| 4-Amino-2-chlorobenzoic acid | C7H6ClNO2 |
| 4-Amino-3-chlorobenzoic acid | C7H6ClNO2 |
| 5-Amino-2-chlorobenzoic acid | C7H6ClNO2 |
| 5-Amino-2-chlorobenzoic acid | C7H6ClNO2 |
| 4-Amino-5-chloro-2-methoxybenzoic acid | C8H8ClNO3 |
| 2-Amino-5-chloro-3-methylbenzoic acid | C8H8ClNO2 |
| 3-Amino-2,5-dichlorobenzoic acid | C7H5Cl2NO2 |
| 4-Amino-3,5-dichlorobenzoic acid | C7H5Cl2NO2 |
| 2-Amino-4,5-difluorobenzoic acid | C7H5F2NO2 |
| 2-Amino-4,5-dimethoxybenzoic acid | C9H11NO4 |
| 4-(2-Aminoethyl)benzoic acid | C9H11NO2 |
| 2-Amino-4-fluorobenzoic acid | C7H6FNO2 |
| 2-Amino-5-fluorobenzoic acid | C7H6FNO2 |
| 2-Amino-6-fluorobenzoic acid | C7H6FNO2 |
| 2-Amino-6-fluorobenzoic acid | C7H6FNO2 |
| 4-Amino-2-fluorobenzoic acid | C7H6FNO2 |
| 2-Amino-5-hydroxybenzoic acid | C7H7NO3 |
| 3-Amino-4-hydroxybenzoic acid | C7H7NO3 |
| 4-Amino-3-hydroxybenzoic acid | C7H7NO3 |
| 2-Amino-5-iodobenzoic acid | C7H6INO2 |
| 5-Aminoisophthalic acid | C8H7NO4 |
| 2-Amino-3-methoxybenzoic acid | C8H9NO3 |
| 2-Amino-4-methoxybenzoic acid | C8H9NO3 |
| 2-Amino-5-methoxybenzoic acid | C8H9NO3 |
| 3-Amino-2-methoxybenzoic acid | C8H9NO3 |
| 3-Amino-4-methoxybenzoic acid | C8H9NO3 |
| 3-Amino-5-methoxybenzoic acid | C8H9NO3 |
| 4-Amino-2-methoxybenzoic acid | C8H9NO3 |
| 4-Amino-3-methoxybenzoic acid | C8H9NO3 |
| 5-Amino-2-methoxybenzoic acid | C8H9NO3 |
| 2-Amino-3-methylbenzoic acid | C8H9NO2 |
| 2-Amino-5-methylbenzoic acid | C8H9NO2 |
| 2-Amino-6-methylbenzoic acid | C8H9NO2 |
| 3-(Aminomethyl)benzoic acid | C8H9NO2 |
| 3-Amino-2-methylbenzoic acid | C8H9NO2 |
| 3-Amino-4-methylbenzoic acid | C8H9NO2 |
| 4-(Aminomethyl)benzoic acid | C8H9NO2 |
| 4-Amino-2-methylbenzoic acid | C8H9NO2 |
| 4-Amino-3-methylbenzoic acid | C8H9NO2 |
| 5-Amino-2-methylbenzoic acid | C8H9NO2 |
| 3-Amino-2-naphthoic acid | C11H9NO2 |
| 6-Amino-2-naphthoic acid | C11H9NO2 |
| 2-Amino-3-nitrobenzoic acid | C7H6N2O4 |
| 2-Amino-5-nitrobenzoic acid | C7H6N2O4 |
| 2-Amino-5-nitrobenzoic acid | C7H6N2O4 |
| 4-Amino-3-nitrobenzoic acid | C7H6N2O4 |
| 5-Amino-2-nitrobenzoic acid | C7H6N2O4 |
| 3-(4-Aminophenyl)propionic acid | C9H11NO2 |
| 3-Aminophthalic acid | C8H7NO4 |
| 4-Aminophthalic acid | C8H7NO4 |
| 3-Aminosalicylic acid | C7H7NO3 |
| 4-Aminosalicylic acid | C7H7NO3 |
| 5-Aminosalicylic acid | C7H7NO3 |
| 5-Aminosalicylic acid | C7H7NO3 |
| 2-Aminoterephthalic acid | C8H7NO4 |
| 2-Amino-3,4,5,6-tetrafluorobenzoic acid | C7H3F4NO2 |
| 4-Amino-2,3,5,6-tetrafluorobenzoic acid | C7H3F4NO2 |
| (R)-2-Amino-1,2,3,4-tetrahydronaphthalene-2-carboxylic acid | C11H13NO2 |
| (S)-2-Amino-1,2,3,4-tetrahydro-2-naphthalenecarboxylic acid | C11H13NO2 |
| 2-Amino-3-(trifluoromethyl)benzoic acid | C8H6F3NO2 |
| 2-Amino-3-(trifluoromethyl)benzoic acid | C8H6F3NO2 |
| 3-Amino-5-(trifluoromethyl)benzoic acid | C8H6F3NO2 |
| 5-Amino-2,4,6-triiodoisophthalic acid | C8H4I3NO4 |
| 2-Amino-3,4,5-trimethoxybenzoic acid | C10H13NO5 |
| 2-Anilinophenylacetic acid | C14H13NO2 |
| 2-Abz-OH | |
| 3-Abz-OH | |
| 4-Abz-OH | |
| 2-aminomethylbenzoic acid | |
| 3-aminomethylbenzoic acid | |
| 4-aminomethylbenzoic acid | |
| tert-Butyl 2-aminobenzoate | C11H15NO2 |
| tert-Butyl 3-aminobenzoate | C11H15NO2 |
| tert-Butyl 4-aminobenzoate | C11H15NO2 |
| 4-(Butylamino)benzoic acid | C11H15NO2 |
| 2,3-Diaminobenzoic acid | C7H8N2O2 |
| 3,4-Diaminobenzoic acid | C7H8N2O2 |
| 3,5-Diaminobenzoic acid | C7H8N2O2 |
| 3,5-Diaminobenzoic acid | C7H8N2O2 |
| 3,5-Dibromoanthranilic acid | C7H5Br2NO2 |
| 3,5-Dichloroanthranilic acid | C7H5Cl2NO2 |
| 4-(Diethylamino)benzoic acid | C11H15NO2 |
| 4,5-Difluoroanthranilic acid | C7H5F2NO2 |
| 4-(Dimethylamino)benzoic acid | C9H11NO2 |
| 4-(Dimethylamino)benzoic acid | C9H11NO2 |
| 3,5-Dimethylanthranilic acid | C9H11NO2 |
| 5-Fluoro-2-methoxybenzoic acid | C8H7FO3 |
| 2-Abz-OH | |
| 3-Abz-OH | |
| 4-Abz-OH | |
| 3-aminomethylbenzoic acid | |
| 4-aminomethylbenzoic acid | |
| 4-(2-hydrazino)benzoic acid | |
| 3-Hydroxyanthranilic acid | C7H7NO3 |
| 3-Hydroxyanthranilic acid | C7H7NO3 |
| Methyl 3-aminobenzoate | C8H9NO2 |
| 3-(Methylamino)benzoic acid | C8H9NO2 |
| 4-(Methylamino)benzoic acid | C8H9NO2 |
| Methyl 2-amino-4-chlorobenzoate | C8H8ClNO2 |
| Methyl 2-amino-4,5-dimethoxybenzoate | C10H13NO4 |
| 4-Nitroanthranilic acid | C7H6N2O4 |
| N-Phenylanthranilic acid | C13H11NO2 |
| N-Phenylanthranilic acid | C13H11NO2 |
| Sodium 4-aminosalicylate | C7H6NNaO3 |
| DL-β-phenylalanine | |
| β-Alanine | C3H7NO2 |

TABLE 1-continued

| Modified Amino Acid Residue | Abbreviation |
|---|---|
| 3-Amino-3-(3-bromophenyl)propionic acid | C9H10BrNO2 |
| 3-Aminobutanoic acid | C4H9NO2 |
| cis-2-Amino-3-cyclopentene-1-carboxylic acid | C6H9NO2 |
| DL-3-Aminoisobutyric acid | C4H9NO2 |
| DL-β-Aminoisobutyric acid | C4H9NO2 |
| (R)-3-Amino-2-phenylpropionic acid | C9H11NO2 |
| 3-Amino-4,4,4-trifluorobutyric acid | C4H6F3NO2 |
| β-Ala-OH | |
| (±)-3-amino-4-(4-biphenylyl)butyric acid | |
| cis-3-aminocyclohexanecarboxylic acid | |
| (1S,3R)-(+)-3-aminocyclopentanecarboxylic acid | |
| (2R,3R)-3-amino-2-hydroxy-4-phenylbutyric acid | |
| (2S,3R)-3-amino-2-hydroxy-4-phenylbutyric acid | |
| 2-aminomethylphenylacetic acid | |
| (R)-3-amino-2-methylpropionic acid | |
| (S)-3-amino-2-methylpropionic acid | |
| (R)-3-amino-4-(2-naphthyl)butyric acid | |
| (S)-3-amino-4-(2-naphthyl)butyric acid | |
| (R)-3-amino-5-phenylpentanoic acid | |
| (S)-3-amino-5-phenylpentanoic acid | |
| (R)-3-amino-2-phenylpropionic acid | |
| (R)-4-bromo-β-Phe-OH | |
| (S)-4-bromo-β-Phe-OH | |
| (R)-4-chloro-β-Homophe-OH | |
| (S)-4-chloro-β-Homophe-OH | |
| (R)-4-chloro-β-Phe-OH | |
| (S)-4-chloro-β-Phe-OH | |
| (S)-2-cyano-β-Homophe-OH | |
| (R)-4-cyano-β-Homophe-OH | |
| (S)-4-cyano-β-Homophe-OH | |
| (R)-3-cyano-β-Phe-OH | |
| (R)-4-cyano-β-Phe-OH | |
| (S)-4-cyano-β-Phe-OH | |
| (R)-3,4-dimethoxy-β-Phe-OH | |
| (S)-3,4-dimethoxy-β-Phe-OH | |
| (S)-γ,γ-diphenyl-β-Homoala-OH | |
| (R)-4-fluoro-β-Phe-OH | |
| (S)-4-fluoro-β-Phe-OH | |
| β-Gln-OH | |
| β-Glu-OH | |
| β-Homoala-OH | |
| β-Homoala-OH | |
| β-Homoarg-OH | |
| β-Homogln-OH | |
| β-Homoglu-OH | |
| β-Homohyp-OH | |
| β-Homoile-OH | |
| β-Homoleu-OH | |
| β-Homolys-OH | |
| β-Homomet-OH | |
| β-Homophe-OH | |
| β3-Homopro-OH | |
| β-Homoser-OH | |
| β-Homothr-OH | |
| β-Homotrp-OH | |
| β-Homotrp-OH | |
| β-Homotyr-OH | |
| (S)-4-iodo-β-Homophe-OH | |
| β-Leu-OH | |
| D-β-Leu-OH | |
| β-Lys-OH | |
| (R)-3-methoxy-β-Phe-OH | |
| (S)-3-methoxy-β-Phe-OH | |
| (R)-4-methoxy-β-Phe-OH | |
| (S)-4-methyl-β-Homophe-OH | |
| (R)-2-methyl-β-Phe-OH | |
| (S)-2-methyl-β-Phe-OH | |
| (R)-3-methyl-β-Phe-OH | |
| (S)-3-methyl-β-Phe-OH | |
| (R)-4-methyl-β-Phe-OH | |
| (S)-4-methyl-β-Phe-OH | |
| β-Phe-OH | |
| D-β-Phe-OH | |
| (R)-4-(4-pyridyl)-β-Homoala-OH | |
| (S)-4-(4-pyridyl)-β-Homoala-OH | |
| (S)-2-(trifluoromethyl)-β-Homophe-OH | |
| (S)-2-(trifluoromethyl)-β-Homophe-OH | |
| (S)-3-(trifluoromethyl)-β-Homophe-OH | |
| (R)-4-(trifluoromethyl)-β-Homophe-OH | |
| (S)-2-(trifluoromethyl)-β-Phe-OH | |
| (R)-3-(trifluoromethyl)-β-Phe-OH | |
| (S)-3-(trifluoromethyl)-β-Phe-OH | |
| (R)-4-(trifluoromethyl)-β-Phe-OH | |
| (S)-4-(trifluoromethyl)-β-Phe-OH | |
| (R)-β-Tyr-OH | |
| (S)-β-Tyr-OH | |
| Ethyl 3-(benzylamino)propionate | C12H17NO2 |
| β-Ala-OH | |
| cis-3-aminocyclohexanecarboxylic acid | |
| (S)-3-amino-5-hexenoic acid | |
| (R)-3-amino-2-methylpropionic acid | |
| (S)-3-amino-2-methylpropionic acid | |
| (R)-3-amino-4-(2-naphthyl)butyric acid | |
| (S)-3-amino-4-(2-naphthyl)butyric acid | |
| (S)-3-amino-6-phenyl-5-hexenoic acid | |
| (R)-3-amino-5-phenyl-pentanoic acid | |
| (S)-3-amino-5-phenyl-pentanoic acid | |
| (S)-3-cyano-β-Homophe-OH | |
| (S)-3,4-difluoro-β-Homophe-OH | |
| (S)-γ,γ-diphenyl-β-Homoala-OH | |
| (R)-4-fluoro-β-Homophe-OH | |
| β-Gln-OH | |
| β-Gln-OH | |
| β-Glu-OH | |
| β-Homoala-OH | |
| β-Homoarg-OH | |
| β-Homogln-OH | |
| β-Homogln-OH | |
| β-Homoglu-OH | |
| β-Homohyp-OH | |
| β-Homoile-OH | |
| β-Homoleu-OH | |
| β-Homolys-OH | |
| β-Homomet-OH | |
| β-Homophe-OH | |
| D-β-Homophe-OH | |
| L-β3-homoproline | |
| β-Homoser-OH | |
| β-Homothr-OH | |
| β-Homotrp-OH | |
| β-Homotyr-OH | |
| β-Leu-OH | |
| (S)-2-methyl-β-Homophe-OH | |
| (S)-3-methyl-β-Homophe-OH | |
| β-Phe-OH | |
| β-D-Phe-OH | |
| (R)-4-(3-pyridyl)-β-Homoala-OH | |
| (S)-3-(trifluoromethyl)-β-Homophe-OH | |
| β-Glutamic acid | C5H9NO4 |
| L-β-Homoalanine | C4H9NO2 |
| L-β-Homoglutamic acid | C6H11NO4 |
| L-β-Homoglutamine | C6H12N2O3 |
| L-β-Homohydroxyproline | C6H11NO3 |
| L-β-Homoisoleucine | C7H15NO2 |
| L-β-Homoleucine | C7H15NO2 |
| DL-β-Homoleucine | C7H15NO2 |
| L-β-Homolysine | C7H16N2O2 |
| L-β-Homomethionine | C6H13NO2S |
| DL-β-Homomethionine | C6H13NO2S |
| L-β-Homophenylalanine | C10H13NO2 |
| DL-β-Homophenylalanine | C10H13NO2 |
| 'L-β-Homoproline' | C6H11NO2 |
| L-β-Homoserine | C4H9NO3 |
| L-β-Homothreonine | C5H11NO3 |
| L-β-Homotryptophan | C12H14N2O2 |
| L-β-Homotyrosine | C10H13NO3 |
| L-β-Leucine | C6H13NO2 |
| DL-β-Leucine | C6H13NO2 |
| DL-β-Phenylalanine | C9H11NO2 |
| (R)-(−)-Pyrrolidine-3-carboxylic acid | C5H9NO2 |
| (S)-(+)-Pyrrolidine-3-carboxylic acid | C5H9NO2 |
| D-β-Dab-OH | |
| β-Ala-OH | |
| β-Dab-OH | |
| β-Dab-OH | |
| D-β-Dab-OH | |

TABLE 1-continued

| Modified Amino Acid Residue | Abbreviation |
|---|---|
| DL-β-Homoalanine | |
| β-Homoala-OH | |
| β-D-Homoala-OH | |
| β-Homotrp-OH | |
| D-Allylglycine | C5H9NO2 |
| N-[Bis(methylthio)methylene]glycine | |
| allyl-Gly-OH | |
| D-allyl-Gly-OH | |
| Chg-OH | |
| D-Chg-OH | |
| D-cyclopropylglycine | |
| L-cyclopropylglycine | |
| iminodiacetic acid | |
| (2-indanyl)-Gly-OH | |
| (±)-α-phosphonoglycine | |
| propargyl-Gly-OH | |
| (R)-2-thienylglycine | |
| (S)-2-thienylglycine | |
| (R)-3-thienylglycine | |
| (S)-3-thienylglycine | |
| (2S,3R,4S)-α-(Carboxycyclopropyl)glycine | C6H9NO4 |
| N-(2-Carboxyphenyl)glycine | C9H9NO4 |
| N-(Chloroacetyl)glycine | |
| D-α-Cyclohexylglycine | C8H15NO2 |
| L-α-Cyclopropylglycine | C5H9NO2 |
| Di-tert-butyl-iminodicarboxylate | C10H19NO4 |
| Ethyl acetamidocyanoacetate | C7H10N2O3 |
| allyl-Gly-OH | |
| D-allyl-Gly-OH | |
| N-4-aminobutyl-Gly-OH | |
| N-(2-aminoethyl)-Gly-OH | |
| N-4-piperidylglycine | |
| N-(2,4-dimethoxybenzyl)-Gly-OH | |
| iminodiacetic acid | |
| (2-indanyl)-Gly-OH | |
| propargyl-Gly-OH | |
| D-propargyl-Gly-OH | |
| trans-N-(2-Furfurylideneacetyl)glycine | C9H9NO4 |
| N-(2-Furfurylideneacetyl)glycine | |
| N-(2-Furoyl)glycine | C7H7NO4 |
| N-(2-Hydroxyethyl)iminodiacetic acid | C6H11NO5 |
| N-(4-Hydroxyphenyl)glycine | C8H9NO3 |
| Iminodiacetic acid | C4H7NO4 |
| N-Lauroylsarcosine | |
| L-α-Neopentylglycine | C7H15NO2 |
| N-(Phosphonomethyl)glycine | C3H8NO5P |
| L-C-Propargylglycine | C5H7NO2 |
| Sarcosine | C3H7NO2 |
| D-Chg-OH | |
| α-Phosphonoglycine | |
| (±)-α-Phosphonoglycine | |
| L-Abrine | C12H14N2O2 |
| N-Me-Aib-OH | |
| N-Me-Ala-OH | |
| N-Me-D-Ala-OH | |
| N-Me-Ile-OH | |
| N-Me-Leu-OH | |
| N-Me-D-Leu-OH | |
| N-Me-Phe-OH | |
| N-Me-Ser-OH | |
| N-Me-Thr-OH | |
| N-Me-Tyr-OH | |
| N-Me-Val-OH | |
| N-Me-Aib-OH | |
| N-Me-Ala-OH | |
| N-Me-D-Ala-OH | |
| N-Me-Ile-OH | |
| N-Me-Leu-OH | |
| N-Me-D-Leu-OH | |
| N-Me-Nle-OH | |
| N-Me-Phe-OH | |
| N-Me-D-Phe-OH | |
| N-Me-Ser-OH | |
| N-Me-Thr-OH | |
| N-Me-Val-OH | |
| N-Methyl-L-alanine | C4H9NO2 |
| N-Methyl-L-isoleucine | C7H15NO2 |
| N-Methyl-L-leucine | C7H15NO2 |
| N-Methyl-L-phenylalanine | C10H13NO2 |
| N-Methyl-L-proline | C6H11NO2 |
| Z-N-Me-Aib-OH | |
| Z-N-Me-Ala-OH | C12H15NO4 |
| Z-N-Me-Leu-OH | C15H21NO4 |
| Z-N-Me-Val-OH | C14H19NO4 |
| D-penicillamine | |
| Pen-OH | |
| D-Pen-OH | |
| D-Penicillamine | C5H11NO2S |
| L-Penicillamine | C5H11NO2S |
| DL-Penicillamine | C5H11NO2S |
| D-Penicillamine disulfide | C10H20N2O4S2 |
| (4R)-4-benzyl-Pyr-OH | |
| (4R)-4-(2-bromobenzyl)-Pyr-OH | |
| (4R)-4-(4-bromobenzyl)-Pyr-OH | |
| (4R)-4-(4-methylbenzyl)-Pyr-OH | |
| (R)-5-oxopyrrolidine-2-carboxylic acid | |
| (S)-5-oxopyrrolidine-2-carboxylic acid | |
| Ethyl (R)-(−)-2-pyrrolidone-5-carboxylate | C7H11NO3 |
| Ethyl (S)-(+)-2-pyrrolidone-5-carboxylate | C7H11NO3 |
| L-Pyroglutamic acid | C5H7NO3 |
| D-Pyroglutamic acid | |
| N-Benzoyl-(2R,3S)-3-phenylisoserine | C16H15NO4 |
| D-Cycloserine | C3H6N2O2 |
| L-Isoserine | C3H7NO3 |
| DL-Isoserine | C3H7NO3 |
| DL-3-Phenylserine | C9H11NO3 |
| L-allo-Threonine | C4H9NO3 |
| 5-Fluoro-L-tryptophan | C11H11FN2O2 |
| 5-Fluoro-DL-tryptophan | C11H11FN2O2 |
| 5-Fluoro-DL-tryptophan | C11H11FN2O2 |
| 5-Hydroxy-L-tryptophan | C11H12N2O3 |
| 5-Methoxy-DL-tryptophan | C12H14N2O3 |
| 5-Methyl-DL-tryptophan | C12H14N2O2 |
| 3-Amino-L-tyrosine | C9H12N2O3 |
| Tyr(3,5-I2)-OH | |
| 3-Chloro-L-tyrosine | C9H10ClNO3 |
| Tyr(3-NO2)-OH | |
| Tyr(3,5-I2)-OH | |
| α-Methyl-DL-tyrosine | C10H13NO3 |
| 3-Nitro-L-tyrosine | C9H10N2O5 |
| 3-Nitro-L-tyrosine | |
| 3-Nitro-L-tyrosine | |
| DL-o-Tyrosine | C9H11NO3 |
| DL-m-Tyrosine | C9H11NO3 |
| 3-Fluoro-DL-valine | C5H10FNO2 |
| (R)-(+)-α-Methylvaline | C6H13NO2 |
| (S)-(−)-α-Methylvaline | C6H13NO2 |
| 3-(3,4-dimethoxyphenyl)-D-alanine | |
| 2-fluoro-DL-phenylalanine | |
| 4-fluoro-DL-phenylalanine | |
| 4-Amino-L-phenylalanine | C9H12N2O2 |
| 4-azido-Phe-OH | |
| Bpa-OH | |
| D-Bpa-OH | |
| 4-tert-butyl-Phe-OH | |
| 4-tert-butyl-D-Phe-OH | |
| 4-amino-L-phenylalanine | |
| rac-β2-homophenylalanine | |
| (S)-4-methoxy-β-Phe-OH | |
| pentafluoro-D-phenylalanine | |
| pentafluoro-L-phenylalanine | |
| Phe(4-Br)-OH | |
| D-Phe(4-Br)-OH | |
| Phe(2-CF3)-OH | |
| D-Phe(2-CF3)-OH | |
| Phe(3-CF3)-OH | |
| D-Phe(3-CF3)-OH | |
| Phe(4-CF3)-OH | |
| D-Phe(4-CF3)-OH | |
| Phe(2-Cl)-OH | |
| D-Phe(2-Cl)-OH | |
| Phe(2,4-Cl2)-OH | |
| D-Phe(2,4-Cl2)-OH | |
| D-Phe(3-Cl)-OH | |
| Phe(3,4-Cl2)-OH | |
| D-Phe(3,4-Cl2)-OH | |

TABLE 1-continued

| Modified Amino Acid Residue | Abbreviation |
|---|---|
| Phe(4-Cl)-OH | |
| D-Phe(4-Cl)-OH | |
| Phe(2-CN)-OH | |
| D-Phe(2-CN)-OH | |
| Phe(3-CN)-OH | |
| D-Phe(3-CN)-OH | |
| Phe(4-CN)-OH | |
| D-Phe(4-CN)-OH | |
| Phe(2-Me)-OH | |
| D-Phe(2-Me)-OH | |
| Phe(3-Me)-OH | |
| D-Phe(3-Me)-OH | |
| Phe(4-Me)-OH | |
| D-Phe(4-Me)-OH | |
| Phe(4-NH2)-OH | |
| Phe(4-NO2)-OH | |
| D-Phe(4-NO2)-OH | |
| Phe(2-F)-OH | |
| D-Phe(2-F)-OH | |
| Phe(3-F)-OH | |
| D-Phe(3-F)-OH | |
| Phe(3,4-F2)-OH | |
| D-Phe(3,4-F2)-QH | |
| Phe(3,5-F2)-OH | |
| Phe(4-F)-OH | |
| D-Phe(4-F)-OH | |
| Phe(4-I)-OH | |
| D-Phe(4-I)-OH | |
| 4-Borono-D-phenylalanine | C9H12BNO4 |
| 4-Borono-L-phenylalanine | C9H12BNO4 |
| 4-Borono-DL-phenylalanine | C9H12BNO4 |
| p-Bromo-DL-phenylalanine | C9H10BrNO2 |
| 4-Bromo-L-phenylalanine | C9H10BrNO2 |
| β-phenyl-D-phenylalanine | |
| 4-Chloro-L-phenylalanine | C9H10ClNO2 |
| DL-3,5-Difluorophenylalanine | C9H9F2NO2 |
| 3,4-Dihydroxy-L-phenylalanine | C9H11NO4 |
| 3-(3,4-Dimethoxyphenyl)-L-alanine | C11H15NO4 |
| o-Fluoro-DL-phenylalanine | C9H10FNO2 |
| m-Fluoro-DL-phenylalanine | C9H10FNO2 |
| p-Fluoro-D-phenylalanine | C9H10FNO2 |
| p-Fluoro-D-phenylalanine | C9H10FNO2 |
| p-Fluoro-L-phenylalanine | C9H10FNO2 |
| p-Fluoro-DL-phenylalanine | C9H10FNO2 |
| 4-Fluoro-D-phenylalanine | C9H10FNO2 |
| 4-Fluoro-L-phenylalanine | C9H10FNO2 |
| Bpa-OH | |
| D-Bpa-OH | |
| pentafluoro-L-phenylalanine | |
| Phe(2-guanidino)-OH | |
| Phe(4-Br)-OH | |
| Phe(2-CF3)-OH | |
| D-Phe(2-CF3)-OH | |
| Phe(3-CF3)-OH | |
| D-Phe(3-CF3)-OH | |
| Phe(4-CF3)-OH | |
| D-Phe(4-CF3)-OH | |
| Phe(2-Cl)-OH | |
| D-Phe(2-Cl)-OH | |
| Phe(2,4-Cl2)-OH | |
| D-Phe(2,4-Cl2)-OH | |
| Phe(3,4-Cl2)-OH | |
| D-Phe(3,4-Cl2)-OH | |
| Phe(4-Cl)-OH | |
| D-Phe(4-Cl)-OH | |
| Phe(2-CN)-OH | |
| D-Phe(2-CN)-OH | |
| Phe(3-CN)-OH | |
| D-Phe(3-CN)-OH | |
| Phe(4-CN)-OH | |
| Phe(2-Me)-OH | |
| Phe(3-Me)-OH | |
| D-Phe(3-Me)-OH | |
| Phe(4-Me)-OH | |
| Phe(4-NO2)-OH | |
| D-Phe(4-NO2)-OH | |
| Phe(2-F)-OH | |
| D-Phe(2-F)-OH | |
| Phe(3-F)-OH | |
| D-Phe(3-F)-OH | |
| Phe(3,4-F2)-OH | |
| Phe(3,5-F2)-OH | |
| Phe(4-F)-OH | |
| D-Phe(4-F)-OH | |
| Phe(4-I)-OH | |
| D-Phe(4-I)-OH | |
| 4-(phosphonomethyl)-Phe-OH | |
| 6-Hydroxy-DL-DOPA | C9H11NO5 |
| 4-(Hydroxymethyl)-D-phenylalanine | C10H13NO3 |
| N-(3-Indolylacetyl)-L-phenylalanine | C19H18N2O3 |
| p-Iodo-D-phenylalanine | C9H10INO2 |
| 4-Iodo-L-phenylalanine | |
| α-Methyl-D-phenylalanine | C10H13NO2 |
| α-Methyl-L-phenylalanine | C10H13NO2 |
| α-Methyl-DL-phenylalanine | C10H13NO2 |
| α-Methyl-DL-phenylalanine | |
| 4-Nitro-D-phenylalanine | |
| 4-Nitro-L-phenylalanine | C9H10N2O4 |
| 4-Nitro-DL-phenylalanine | C9H10N2O4 |
| (S)-(+)-4-Nitrophenylalanine | |
| 2-(Trifluoromethyl)-D-phenylalanine | C10H10F3NO2 |
| 2-(Trifluoromethyl)-L-phenylalanine | C10H10F3NO2 |
| 3-(Trifluoromethyl)-D-phenylalanine | C10H10F3NO2 |
| 3-(Trifluoromethyl)-L-phenylalanine | C10H10F3NO2 |
| 4-(Trifluoromethyl)-D-phenylalanine | C10H10F3NO2 |
| 3,3',5-Triiodo-L-thyronine | |
| L-Phe chloromethyl ketone | |
| D-2-Amino-2-phenylacetamide | C8H10N2O |
| Phg-OH | |
| D-Phg-OH | |
| 2-(piperazino)-2-(3,4-dimethoxyphenyl)acetic acid | |
| 2-(piperazino)-2-(2-fluorophenyl)acetic acid | |
| 2-(piperazino)-2-(3-fluorophenyl)acetic acid | |
| 2-(piperazino)-2-(4-methoxyphenyl)acetic acid | |
| 2-(piperazino)-2-(3-pyridyl)acetic acid | |
| 2-(piperazino)-2-[4-(trifluoromethyl)phenyl]acetic acid | |
| L-(+)-2-Chlorophenylglycine | C8H8ClNO2 |
| (±)-2-Chlorophenylglycine | C8H8ClNO2 |
| (±)-4-Chlorophenylglycine | C8H8ClNO2 |
| (R)-(−)-2-(2,5-Dihydrophenyl)glycine | C8H11NO2 |
| (R)-(−)-N-(3,5-Dinitrobenzoyl)-α-phenylglycine | C15H11N3O7 |
| N-(3,5-Dinitrobenzoyl)-D-α-phenylglycine | C15H11N3O7 |
| (S)-(+)-N-(3,5-Dinitrobenzoyl)-α-phenylglycine | C15H11N3O7 |
| N-(3,5-Dinitrobenzoyl)-DL-α-phenylglycine | C15H11N3O7 |
| 2,2-Diphenylglycine | C14H13NO2 |
| 2-Fluoro-DL-α-phenylglycine | C8H8FNO2 |
| 4-Fluoro-D-α-phenylglycine | C8H8FNO2 |
| 4-Fluoro-L-α-phenylglycine | C8H8FNO2 |
| 4-Fluoro-DL-α-phenylglycine | C8H8FNO2 |
| Phg-OH | |
| D-Phg-OH | |
| 4-Hydroxy-D-phenylglycine | C8H9NO3 |
| 4-Hydroxy-L-phenylglycine | C8H9NO3 |
| Methyl 2-(piperazino)-2-(4-pyridyl)acetate | |
| 2-Phenylglycine | C8H9NO2 |
| D-(−)-α-Phenylglycine | C8H9NO2 |
| D-(−)-α-Phenylglycine | C8H9NO2 |
| DL-α-Phenylglycine | C8H9NO2 |
| L-(+)-α-Phenylglycine | C8H9NO2 |
| N-Phenylglycine | C8H9NO2 |
| (R)-(−)-2-Phenylglycine | |
| (S)-(+)-2-Phenylglycine | |
| 2-Phenylglycinonitrile | C8H8N2 |
| 2-(Trifluoromethyl)-DL-phenylglycine | C9H8F3NO2 |
| 3-(Trifluoromethyl)-DL-phenylglycine | C9H8F3NO2 |
| 4-(Trifluoromethyl)-L-phenylglycine | C9H8F3NO2 |
| Phg-OH | |
| D-Phg-OH | |
| trans-1-Acetyl-4-hydroxy-L-proline | C7H11NO4 |
| N-[3-(Acetylthio)-(2S)-methylpropionyl]-L-proline | C11H17NO4S |
| (R)-α-Allyl-proline | C8H13NO2 |
| (S)-α-Allyl-proline | C8H13NO2 |
| (R)-α-allyl-Pro-OH | |
| (S)-α-allyl-Pro-OH | |
| α-allyl-DL-Pro-OH | |
| cis-4-azido-L-proline | |

TABLE 1-continued

| Modified Amino Acid Residue | Abbreviation |
|---|---|
| (R)-α-benzyl-Pro-OH | |
| (S)-α-benzyl-Pro-OH | |
| α-benzyl-DL-Pro-OH | |
| α-(2-bromobenzyl)-DL-Pro-OH | |
| α-(4-bromobenzyl)-DL-Pro-OH | |
| (R)-α-(4-tert-butylbenzyl)-Pro-OH | |
| (S)-α-(4-tert-butylbenzyl)-Pro-OH | |
| α-(2-chlorobenzyl)-DL-Pro-OH | |
| α-(3-chlorobenzyl)-DL-Pro-OH | |
| (R)-4-(3,4-difluorobenzyl)-L-proline | |
| α-(diphenylmethyl)-DL-Pro-OH | |
| (R)-α-(4-fluorobenzyl)-Pro-OH | |
| (S)-α-(4-fluorobenzyl)-Pro-OH | |
| α-(4-fluorobenzyl)-DL-Pro-OH | |
| cis-4-amino-L-proline | |
| trans-4-amino-L-proline | |
| cis-4-hydroxy-D-proline | |
| cis-4-hydroxy-L-proline | |
| cis-4-hydroxy-L-proline | |
| trans-4-hydroxy-L-proline | |
| Hyp-OH | |
| α-Me-DL-Pro-OH | |
| α-(4-methylbenzyl)-DL-Pro-OH | |
| α-(1-naphthylmethyl)-DL-Pro-OH | |
| 2-piperidinecarboxylic acid | |
| 2-piperidinecarboxylic acid | |
| (R)-(+)-2-piperidinecarboxylic acid | |
| Pip-OH | |
| α-propyl-DL-Pro-OH | |
| α-(2-propynyl)-L-proline | |
| (R)-4-(2-propynyl)-L-proline | |
| trans-4-(p-tosyloxy)-L-proline | |
| (R)-4-[2-(trifluoromethyl)benzyl]-L-proline | |
| (R)-4-[4-(trifluoromethyl)benzyl]-L-proline | |
| (R)-α-(4-trifluoromethylbenzyl)-Pro-OH | |
| (S)-α-(4-trifluoromethylbenzyl)-Pro-OH | |
| 3,4-Dehydro-L-proline | C5H7NO2 |
| 3,4-Dehydro-DL-proline | C5H7NO2 |
| 3,4-Dehydro-DL-proline | C5H7NO2 |
| Hyp-OH | |
| Hyp(tBu)-OH | |
| Pip-OH | |
| D-Pip-OH | |
| cis-3-Hydroxy-DL-proline | C5H9NO3 |
| cis-4-Hydroxy-D-proline | C5H9NO3 |
| cis-4-Hydroxy-L-proline | C5H9NO3 |
| trans-4-Hydroxy-D-proline | C5H9NO3 |
| trans-4-Hydroxy-L-prolineure | C5H9NO3 |
| trans-4-Hydroxy-L-proline | C5H9NO3 |
| L-4-Hydroxy-proline | |
| L-4-Hydroxyproline | |
| (S)-(+)-Methyl indoline-2-carboxylate | C10H11NO2 |
| α-Methyl-L-proline | C6H11NO2 |
| (S)-1-Z-4-oxopyrrolidine-2-carboxylic acid | C13H13NO5 |
| L-Pipecolic acid | C6H11NO2 |
| L-Pipecolic acid Proline homolog | C6H11NO2 |
| Pipecolinic acid | C6H11NO2 |
| D-Pipecolinic acid | C6H11NO2 |
| Hyp-OH | |
| Albizziin | C4H9N3O3 |
| (S)-α-Amino-γ-butyrolactone | C4H7NO2 |
| DL-2-Aminocaprylic acid | C8H17NO2 |
| 7-Aminocephalosporanic acid | C10H12N2O5S |
| 4-Aminocinnamic acid predominantly trans | C9H9NO2 |
| (S)-(+)-α-Aminocyclohexanepropionic acid | C9H17NO2 |
| (R)-Amino-(4-hydroxyphenyl)acetic acid | |
| 5-Aminolevulinic acid | C5H9NO3 |
| 4-Amino-nicotinic acid | C6H6N2O2 |
| 3-Aminophenylacetic acid | C8H9NO2 |
| 4-Aminophenylacetic acid | C8H9NO2 |
| 2-Amino-2-phenylbutyric acid | C10H13NO2 |
| 4-(4-Aminophenyl)butyric acid | C10H13NO2 |
| 2-(4-Aminophenylthio)acetic acid | C8H9NO2S |
| DL-α-Amino-2-thiopheneacetic acid | C6H7NO2S |
| 5-Aminovaleric acid | C5H11NO2 |
| 8-Benzyl (S)-2-aminooctanedioate | C15H21NO4 |
| Aad-OH | |
| 4-amino-1-methylpyrrole-2-carboxylic acid | |
| 4-aminotetrahydrothiopyran-4-carboxylic acid | |
| (1R,3S,4S)-2-azabicyclo[2.2.1]heptane-3-carboxylic acid | |
| 1-L-azetidine-2-carboxylic acid | |
| 1-azetidine-3-carboxylic acid | |
| 4-aminopiperidine-4-carboxylic acid | |
| diaminoacetic acid | |
| Inp-OH | |
| (R)-Nip-OH | |
| DL-Nip-OH | |
| (S)-4-oxopiperidine-2-carboxylic acid | |
| 2-(4-piperazino)-2-(4-fluorophenyl)acetic acid | |
| 2-(4-piperazino)-2-phenylacetic acid | |
| 4-piperidineacetaldehyde | |
| 4-piperidylacetic acid | |
| (−)-L-thioproline | |
| Tic-OH | |
| D-Tic-OH | |
| Tle-OH | |
| 3-piperidinecarboxylic acid | |
| L-(+)-Canavanine | C5H12N4O3 |
| (±)-Carnitine | |
| Chlorambucil | C14H19Cl2NO2 |
| L-Citrulline | C6H13N3O3 |
| 2,6-Diaminopimelic acid | C7H14N2O4 |
| 2,6-Diaminopimelic acid | C7H14N2O4 |
| meso-2,3-Diaminosuccinic acid | C4H8N2O4 |
| 4-(Dimethylamino)cinnamic acid | C11H13NO2 |
| 4-(Dimethylamino)phenylacetic acid | C10H13NO2 |
| Ethyl (S)-piperidine-3-carboxylate | |
| Ethyl piperazinoacetate | C8H16N2O2 |
| 4-[2-aminoethyl]piperazin-1-ylacetic acid | |
| (R)-4-amino-5-phenylpentanoic acid | |
| (S)-azetidine-2-carboxylic acid | |
| azetidine-3-carboxylic acid | |
| Freidinger's lactam | |
| guvacine | |
| Inp-OH | |
| (R)-Nip-OH | |
| DL-Nip-OH | |
| 4-phenyl-piperidine-4-carboxylic acid | |
| 1-piperazineacetic acid | |
| 4-piperidineacetic acid | |
| (R)-piperidine-2-carboxylic acid | |
| (S)-piperidine-2-carboxylic acid | |
| (R)-1,2,3,4-tetrahydronorharmane-3-carboxylic acid | |
| Tic-OH | |
| D-Tic-OH | |
| (−)-Glutathione, oxidized | C20H32N6O12S2 |
| Iminodiacetic acid | C4H7NO4 |
| Indoline-2-carboxylic acid | C9H9NO2 |
| DL-Kynurenine | C10H12N2O3 |
| Lithium L-aziridine-2-carboxylate | C3H4LiNO2 |
| Methyl 4-aminobutyrate | C5H11NO2 |
| (S)-2-Piperazinecarboxylic acid | C5H10N2O2 |
| 2-(1-Piperazinyl)acetic acid | C6H12N2O2 |
| (R)-(−)-3-Piperidinecarboxylic acid | C6H11NO2 |
| 2-Pyrrolidone-5-carboxylic acid | C5H7NO3 |
| (R)-(+)-2-Pyrrolidone-5-carboxylic acid | C5H7NO3 |
| (R)-1,2,3,4-Tetrahydro-3-isoquinolinecarboxylic acid | C10H11NO2 |
| (S)-1,2,3,4-Tetrahydro-3-isoquinolinecarboxylic acid | C10H11NO2 |
| L-4-Thiazolidinecarboxylic acid | C4H7NO2S |
| (4R)-(−)-2-Thioxo-4-thiazolidinecarboxylic acid | C4H5NO2S2 |
| hydrazinoacetic acid | |
| 3,3',5-Triiodo-L-thyronine | C15H12I3NO4 |
| Tle-OH | |
| L-Allysine ethylene acetal | C8H15NO4 |
| 12-Aminododecanoic acid | C12H25NO2 |
| 2-Aminoheptanoic acid | C7H15NO2 |
| 7-Aminoheptanoic acid | C7H15NO2 |
| 2-Aminohexadecanoic acid | C16H33NO2 |
| 6-Aminohexanoic acid | C6H13NO2 |
| (R)-3-Amino-5-hexynoic acid | C6H9NO2 |
| (S)-3-Amino-5-hexynoic acid | C6H9NO2 |
| 4-Amino-3-hydroxybutyric acid | C4H9NO3 |
| (R)-3-Amino-2-(hydroxymethyl)propionic acid | C4H9NO3 |
| (S)-3-Amino-2-(hydroxymethyl)propionic acid | C4H9NO3 |
| 5-Aminolevulinic acid | C5H9NO3 |

TABLE 1-continued

| Modified Amino Acid Residue | Abbreviation |
|---|---|
| 3-Amino-3-(3-methoxyphenyl)propionic acid | C10H13NO3 |
| (R)-2-(Aminomethyl)-3-methylbutyric acid | C6H13NO2 |
| (S)-2-(Aminomethyl)-3-methylbutyric acid | C6H13NO2 |
| 8-Aminooctanoic acid | C8H17NO2 |
| (R)-3-Aminopentanoic acid | C5H9NO2 |
| (S)-3-Aminopentanoic acid | C5H9NO2 |
| (S)-(−)-2-Amino-4-pentenoic acid | C5H9NO2 |
| 11-Aminoundecanoic acid | C11H23NO2 |
| 11-Aminoundecanoic acid | C11H23NO2 |
| 5-Aminovaleric acid | C5H11NO2 |
| (S)-(−)-2-Azido-6-aminohexanoic acid | |
| 12-Ado-OH | |
| 7-Ahp-OH | |
| 6-Ahx-OH | |
| 6-Ahx-OH | |
| (R)-3-amino-5-hexenoic acid | |
| (S)-3-amino-5-hexenoic acid | |
| (S)-2-amino-5-hexynoic acid | |
| (R)-3-amino-5-hexynoic acid | |
| (S)-3-amino-5-hexynoic acid | |
| (2R,3R)-3-amino-2-methyl-3-(4-chlorophenyl)propionic acid | |
| (2S,3S)-3-amino-2-methyl-3-(4-chlorophenyl)propionic acid | |
| (R)-4-amino-6-methylheptanoic acid | |
| (2R,3R)-3-amino-2-methyl-3-phenylpropionic acid | |
| (2S,3S)-3-amino-2-methyl-3-phenylpropionic acid | |
| (R)-2-aminooctanedioic acid | |
| (S)-2-aminooctanedioic acid | |
| (R)-4-amino)-5-phenylpentanoic acid | |
| 8-Aoc-OH | |
| 11-Aun-OH | |
| 5-Ava-OH | |
| GABA-OH | |
| 3-(Diethylamino)propionic acid | C7H15NO2 |
| 4-(Dimethylamino)butyric acid | C6H13NO2 |
| 12-Ado-OH | |
| 7-Ahp-OH | |
| 6-Ahx-OH | |
| 8-Aoc-OH | |
| 11-Aun-OH | |
| 5-Ava-OH | |
| GABA-OH | |
| 4-(Methylamino)butyric acid | C5H11NO2 |
| 12-(Methylamino)dodecanoic acid | C13H27NO2 |
| Methyl 6-aminohexanoate | C7H15NO2 |
| R(−)-γ-Vinyl GABA | C6H11NO2 |
| 6-Aminohexanoic acid | |
| 2-Amino-3-mercapto-N-(prop-2-ynyl)propionamide | |
| 2-Amino-N-(3-azidopropyl)-3-mercaptopropionamide | |
| Azidohomoalanine | |
| D-propargylglycine | |
| L-propargylglycine | |
| Lys(N3)-OH | |
| 4-azidophenylalanine | |
| Phe(N3)-OH; p-azidophenylalanine; phenylalanine-azide | |
| Azidohomoalanine | |
| D-propargylglycine | |
| D-Pra-OH | |
| L-propargylglycine | |
| Lys(N3)-OH | |
| azidolysine; lys(azide); lysine azide | |
| TBTA, Tris[(1-benzyl-1H-1,2,3-triazol-4-yl)methyl] amine | |
| (piperidin-3-yl)acetic acid | |
| 3-(piperidine-4-yl)-propionic acid | |
| 4-(piperidine-4-yl)-butanoic acid | |
| 4-carboxymethylpiperidine | |
| (R)-(+)-piperidine-2-carboxylic acid | |
| D-(+)-pipecolic acid | |
| (R)-nipecotic acid | |
| (RS)-piperidine-2-carboxylic acid | |
| DL-pipecolic acid | |
| (S)-(−)-piperidine-2-carboxylic acid | |
| L-(−)-pipecolic acid | |
| (S)-(−)-piperidine-2-carboxylic acid | |
| (S)-azetidine-2-carboxylic acid | |
| (S)-nipecotic acid | |
| 1-amino-1,2,3,4-tetrahydro-naphthalene-1-carboxylic acid | |
| 1-aminoindan-1-carboxylic acid | |
| 1-pyrrolidine-3-carboxylic acid | |
| 2-amino-1,2,3,4-tetrahydro-naphthalene-2-carboxylic acid | |
| 2-carboxypiperazine | |
| 3-azabicyclo[3.1.0]hexane-2-carboxylic acid | |
| 3-carboxypiperidine | |
| (RS)-nipecotic acid | |
| 4-amino-(1-carboxymethyl) piperidine | |
| 4-phenylpiperidine-4-carboxylic acid | |
| azetidine-3-carboxylic acid | |
| L-indoline-2-carboxylic acid | |
| piperidine-4-carboxylic acid | |
| isonipecotic acid | |
| (4-carboxymethyl)-piperidine | |
| (R)-(+)-piperidine-2-carboxylic acid | |
| D-(+)-pipecolic acid | |
| (R)-nipecotic acid | |
| (RS)-piperidine-2-carboxylic acid | |
| DL-pipecolic acid | |
| (S)-azetidine-2-carboxylic acid | |
| (S)-nipecotic acid | |
| 1-amino-1,2,3,4-tetrahydro-naphthalene-1-carboxylic acid | |
| 1-aminoindan-1-carboxylic acid | |
| 1-pyrrolidine-3-carboxylic acid | |
| 2-amino-1,2,3,4-tetrahydro-naphthalene-2-carboxylic acid | |
| 2-aminothiazole-4-acetic acid | |
| 2-carboxypiperazine | |
| 3-azabicyclo[3.1.0]hexane-2-carboxylic acid | |
| 3-carboxypiperidine | |
| (RS)-nipecotic acid | |
| 4-(2-aminoethyl)-(1-carboxy-methyl)piperazine | |
| 4-amino-(1-carboxymethyl) piperidine | |
| 4-phenylpiperidine-4-carboxylic acid | |
| azetidine-3-carboxylic acid | |
| L-indoline-2-carboxylic acid | |
| piperidine-4-carboxylic acid | |
| isonipecotic acid | |
| N-(piperidine-4-yl)-L-proline | |
| 3-aminopiperidine | |
| 3-hydroxy-1,2,3,6-tetrahydropyridine | |
| Nα-Me-Arg-OH | |
| Nα-methyl-4-chloro-D-phenylalanine | |
| D-Me(4-Cl-Phe)-OH | |
| Nα-methyl-D-alanine | |
| D-MeAla-OH | |
| Nα-methyl-D-glutamic acid | |
| D-MeGlu-OH | |
| Nα-methyl-D-leucine | |
| D-MeLeu-OH | |
| Nα-methyl-D-phenylalanine | |
| D-MePhe-OH | |
| Nα-methyl-D-tryptophan | |
| D-MeTrp-OH | |
| Nα-methyl-D-valine | |
| D-MeVal-OH | |
| Nα-methyl-DL-tryptophan | |
| DL-MeTrp-OH | |
| Nα-methyl-DL-tryptophan | |
| DL-MeTrp-OH | |
| Nα-methyl-L-alanine | |
| MeAla-OH | |
| Nα-methyl-L-glutamic acid | |
| MeGlu-OH | |
| Nα-methyl-L-leucine | |
| MeLeu-OH | |
| Nα-methyl-L-norleucine | |
| MeNle-OH | |
| Nα-methyl-L-norvaline | |
| MeNva-OH | |
| Nα-methyl-L-phenylalanine | |
| MePhe-OH | |
| Nα-methyl-L-tryptophan | |

TABLE 1-continued

| Modified Amino Acid Residue | Abbreviation |
|---|---|
| MeTrp-OH | |
| Nα-methyl-L-valine | |
| MeVal-OH | |
| Nα-methyl-Nε-2-chlorobenzyl-oxycarbonyl-L-lysine | |
| MeLys(2-Cl-Z)-OH | |
| Nα-methyl-N-im-D-histidine | |
| D-MeHis-OH | |
| Nα-methyl-N-im-L-histidine | |
| MeHis-OH | |
| Nα-methyl-D-tyrosine | |
| D-MeTyr-OH | |
| Nα-methyl-L-serine | |
| MeSer-OH | |
| Nα-methyl-L-threonine | |
| Boc-MeThr-OH | |
| Nα-methyl-L-threonine | |
| MeThr-OH | |
| Nα-methyl-L-tyrosine | |
| MeTyr-OH | |
| Nα-methylglycine | |
| sarcosine; Sar-OH | |
| N-Me-4-methoxy-Phe-OH | |
| N-Me-Tyr(Me)-OH | |
| MeGlu-OH | |
| N-α-methyl-L-glutamic acid | |
| Nα-Me-Arg-OH | |
| Nα-methyl-L-arginine | |
| Nα-methyl-4-chloro-D-phenylalanine | |
| D-Me(4-Cl-Phe)-OH | |
| Nα-methyl-4-chloro-L-phenylalanine | |
| Me-(4-Cl-Phe)-OH | |
| Nα-methyl-D-alanine | |
| D-MeAla-OH | |
| Nα-methyl-D-glutamic acid | |
| D-MeGlu-OH | |
| Nα-methyl-D-glutamic acid | |
| D-MeGlu-OH | |
| Nα-methyl-D-leucine | |
| D-MeLeu-OH | |
| Nα-methyl-D-phenylalanine | |
| D-MePhe-OH | |
| Nα-methyl-D-valine | |
| D-MeVal-OH | |
| Nα-methyl-DL-tryptophan | |
| DL-MeTrp-OH | |
| Nα-methyl-L-alanine | |
| MeAla-OH | |
| Nα-methyl-L-aspartic acid | |
| MeAsp-OH | |
| Nα-methyl-L-glutamic acid | |
| MeGlu-OH | |
| Nα-methyl-L-leucine | |
| MeLeu-OH | |
| Nα-methyl-L-norleucine | |
| MeNle-OH | |
| Nα-methyl-L-norvaline | |
| MeNva-OH | |
| Nα-methyl-L-phenylalanine | |
| MePhe-OH | |
| Nα-methyl-L-phenylglycine | |
| MePhg-OH | |
| Nα-methyl-L-tryptophan | |
| MeTrp-OH | |
| Nα-methyl-L-valine | |
| MeVal-OH | |
| Nα-methyl-L-lysine | |
| MeLys-OH | |
| Nα-methyl-N-im-L-histidine | |
| MeHis-OH | |
| Nα-methyl-D-tyrosine | |
| D-MeTyr-OH | |
| Nα-methyl-L-serine | |
| MeSer-OH | |
| Nα-methyl-L-threonine | |
| MeThr-OH | |
| Nα-methyl-L-tyrosine | |
| MeTyr-OH | |
| Nα-methyl-L-serine | |
| MeSer-OH | |
| Nα-methyl-L-threonine | |
| MeThr-OH | |
| Nα-methyl-L-tyrosine | |
| MeTyr-OH | |
| Nα-methylglycine | |
| sarcosine; Sar-OH | |
| Nα-methyl-L-proline | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

TABLE 2

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |

| | Abbreviation | |
|---|---|---|
| Amino Acid Residue | Three-Letter Code | One-Letter Code |
| Threonine | Thr | T |
| Tryptophan | Trp | W |
| Tyrosine | Tyr | Y |
| Valine | Val | V |

What is claimed is:

1. A method of downregulating G-alpha-Q signaling in a cell, comprising introducing into the cell a peptide comprising the amino acid sequence HQDYAEALANPIKHVSL-Nle-DQR (SEQ ID NO:1).

2. The method of claim 1, wherein the peptide further comprises from one to six additional amino acids, $X_{22}$, $X_{23}$, $X_{24}$, $X_{25}$, $X_{26}$ and $X_{27}$, wherein
   $X_{22}$ is A or any nonnatural amino acid or any amino acid listed in Table 2;
   $X_{23}$ is R or any nonnatural amino acid or any amino acid listed in Table 2;
   $X_{24}$ is Q or any nonnatural amino acid or any amino acid listed in Table 2;
   $X_{25}$ is L or any nonnatural amino acid or any amino acid listed in Table 2;
   $X_{26}$ is A or any nonnatural amino acid or any amino acid listed in Table 2; and
   $X_{27}$ is A or any nonnatural amino acid or any amino acid listed in Table 2.

3. A method of treating a cancer associated with a Gαq mutation in a subject in need thereof, comprising introducing to the subject an effective amount of a peptide comprising the amino acid sequence HQDYAEALANPIKHVSL-Nle-DQR (SEQ ID NO:1).

4. The method of claim 3, wherein the peptide further comprises from one to six additional amino acids, $X_{22}$, $X_{23}$, $X_{24}$, $X_{25}$, $X_{26}$ and $X_{27}$, wherein
   $X_{22}$ is A or any nonnatural amino acid or any amino acid listed in Table 2;
   $X_{23}$ is R or any nonnatural amino acid or any amino acid listed in Table 2;
   $X_{24}$ is Q or any nonnatural amino acid or any amino acid listed in Table 2;
   $X_{25}$ is L or any nonnatural amino acid or any amino acid listed in Table 2;
   $X_{26}$ is A or any nonnatural amino acid or any amino acid listed in Table 2; and
   $X_{27}$ is A or any nonnatural amino acid or any amino acid listed in Table 2.

5. The method of claim 1, wherein the peptide further comprises amino acids YIP$X_{28}$D at the amino terminus, wherein $X_{28}$ is a nonnatural amino acid.

6. The method of claim 5, wherein the peptide is YIP$X_{28}$DHQDYA $X_{28}$ALANPIKHVSLMDQRARALAA and wherein $X_{28}$ is a nonnatural amino acid.

7. The method of claim 1, wherein the peptide further comprises a protein transduction domain (PTD) at the amino and/or carboxy terminus.

8. The method of claim 7, wherein the protein transduction domain is selected from the group consisting of GRKKRRQRRPPQ (SEQ ID NO: 18), RQIKIWFQNRRMKWKK (SEQ ID NO: 19), GWTLNSAGGYLLGKINLKALAALAKKI (SEQ ID NO: 21), RRRRRRRRR (SEQ ID NO: 22), RRRRRRR (SEQ ID NO: 23), KETWWETWWTWWSQPKKKRKV (SEQ ID NO: 24), YGRKKRRQRRR (SEQ ID NO: 25), YARAAARQARA (SEQ ID NO: 26), KETWWETWWTEWS (SEQ ID NO: 27), GWTLNSAGYLLGKINLKALAALAKKIL (SEQ ID NO: 28), Cre recombinase, DAATATRGRSAASRPTERPRAPARSASRPRRPVE (SEQ ID NO: 29), KMTRAQRRAAARRNRRWTAR (SEQ ID NO: 30) and any combination thereof.

9. The method of claim 1, wherein an alphahelical transmembrane domain is added to the peptide with one or more PEG linkers.

10. The method of claim 1, wherein a lipid is added to the peptide with one or more PEG linkers.

11. The method of claim 10, wherein the lipid is selected from the group consisting of palmitic acid, myristic acid and farnesylic acid.

12. The method of claim 11, wherein the peptide is Palm-PEG-PEG-HQDYAEALANPIKHVSL-Nle-DQRARQLAA.

13. The method of claim 1, wherein the cell is in a subject.

14. The method of claim 13, wherein the subject is a human.

15. The method of claim 3, wherein the cancer is uveal melanoma.

16. A method of identifying a test substance having the ability to inhibit G-alpha-q activity, comprising:
   a) contacting a peptide comprising the amino acid sequence HQDYAEALANPIKHVSL-Nle-DQRARQLAA (SEQ ID NO: 4) and further comprising a TAMRA label with G-alpha-q and GDP and aluminum fluoride and determining a baseline fluorescence polarization value; and;

b) contacting the peptide of (a) with G-alpha-q and GDP, aluminum fluoride and the test substance and determining a fluorescence polarization value, wherein a fluorescence polarization value of (b) that is lower than the fluorescence polarization value of (a) identifies the test substance as having the ability to inhibit G-alpha-q activity.

17. A method of identifying a test substance having the ability to increase G-alpha-q activity, comprising:

a) contacting a peptide comprising the amino acid sequence HQDYAEALANPIKHVSL-Nle-DQRARQ-LAA (SEQ ID NO:4) and further comprising a TAMRA label with G-alpha-q and GDP and aluminum fluoride and determining a baseline fluorescence polarization value; and b) contacting the peptide of (a) with G-alpha-q, GDP, aluminum fluoride and the test substance and determining a fluorescence polarization value, wherein a fluorescence polarization value of (b) that is greater than the fluorescence polarization value of (a) identifies the test substance as having the ability to increase G-alpha-q activity.

\* \* \* \* \*

UNITED STATES PATENT AND TRADEMARK OFFICE
CERTIFICATE OF CORRECTION

PATENT NO. : 9,540,620 B2  
APPLICATION NO. : 14/398678  
DATED : January 10, 2017  
INVENTOR(S) : Sondek et al.

Page 1 of 1

It is certified that error appears in the above-identified patent and that said Letters Patent is hereby corrected as shown below:

In the Specification

Column 14, Line 41: Please correct "other Ga" to read -- other Gα --

Column 22, Line 16: Please correct "other Ga" to read -- other Gα --

Signed and Sealed this  
Eighteenth Day of July, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 41

<210> SEQ ID NO 1
<211> LENGTH: 21
<212> TYPE: PRT
<213> ORGANISM: Artificial
<220> FEATURE:
<223> OTHER INFORMATION: G-alpha-Q signalling downregulating peptide
      sequence
<220> FEATURE:
<221> NAME/KEY: MISC_FEATURE
<222> LOCATION: (2)..(2)
<223> OTHER INFORMATION: Xaa can be Q, any naturally occurring amino
      acid, or any nonnatural amino acid, for example, as listed in
      Table 1
<220> FEATURE:
<221> NAME/KEY: MISC_FEATURE
<222> LOCATION: (3)..(3)
<223> OTHER INFORMATION: Xaa can be D, any naturally occurring amino
      acid, or any nonnatural amino acid, for example, as listed in
      Table 1
<220> FEATURE:
<221> NAME/KEY: MISC_FEATURE
<222> LOCATION: (6)..(6)
<223> OTHER INFORMATION: Xaa can be E, any naturally occurring amino
      acid, or any nonnatural amino acid, for example, as listed in
      Table 1
<220> FEATURE:
<221> NAME/KEY: MISC_FEATURE
<222> LOCATION: (8)..(8)
<223> OTHER INFORMATION: Xaa can be L, any naturally occurring amino
      acid, or any nonnatural amino acid, for example, as listed in
      Table 1
<220> FEATURE:
<221> NAME/KEY: MISC_FEATURE
<222> LOCATION: (9)..(9)
<223> OTHER INFORMATION: Xaa can be I, A or N, any naturally occurring
      amino acid, or any nonnatural amino acid, for example, as listed
      in Table 1
<220> FEATURE:
<221> NAME/KEY: MISC_FEATURE
<222> LOCATION: (13)..(13)
<223> OTHER INFORMATION: Xaa can be K, any naturally occurring amino
      acid, or any nonnatural amino acid, for example, as listed in
      Table 1
<220> FEATURE:
<221> NAME/KEY: MISC_FEATURE
<222> LOCATION: (17)..(17)
<223> OTHER INFORMATION: Xaa can be L, any naturally occurring amino
      acid, or any nonnatural amino acid, for example, as listed in
      Table 1
<220> FEATURE:
<221> NAME/KEY: MISC_FEATURE
<222> LOCATION: (18)..(18)
<223> OTHER INFORMATION: Xaa can be M, norleucine, or any nonnatural
      amino acid, for example, as listed in Table 1

<400> SEQUENCE: 1

His Xaa Xaa Tyr Ala Xaa Ala Xaa Xaa Asn Pro Ile Xaa His Val Ser
1               5                   10                  15

Xaa Xaa Asp Gln Arg
            20
```

```
<210> SEQ ID NO 2
<211> LENGTH: 21
<212> TYPE: PRT
<213> ORGANISM: Artificial
<220> FEATURE:
<223> OTHER INFORMATION: G-alpha-Q signaling downregulating peptide
      sequence

<400> SEQUENCE: 2

His Gln Asp Tyr Ala Glu Ala Leu Ile Asn Pro Ile Lys His Val Ser
1               5                   10                  15

Leu Met Asp Gln Arg
            20

<210> SEQ ID NO 3
<211> LENGTH: 27
<212> TYPE: PRT
<213> ORGANISM: Artificial
<220> FEATURE:
<223> OTHER INFORMATION: G-alpha-Q signaling downregulating peptide
      sequence

<400> SEQUENCE: 3

His Gln Asp Tyr Ala Glu Ala Leu Ile Asn Pro Ile Lys His Val Ser
1               5                   10                  15

Leu Met Asp Gln Arg Ala Arg Gln Leu Ala Ala
            20                  25

<210> SEQ ID NO 4
<211> LENGTH: 27
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (18)..(18)
<223> OTHER INFORMATION: Xaa is norleucine

<400> SEQUENCE: 4

His Gln Asp Tyr Ala Glu Ala Leu Ala Asn Pro Ile Lys His Val Ser
1               5                   10                  15

Leu Xaa Asp Gln Arg Ala Arg Gln Leu Ala Ala
            20                  25

<210> SEQ ID NO 5
<211> LENGTH: 27
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (2)..(2)
<223> OTHER INFORMATION: Xaa can be any nonnatural amino acid listed in
      Table 1
<220> FEATURE:
<221> NAME/KEY: MISC_FEATURE
<222> LOCATION: (6)..(6)
<223> OTHER INFORMATION: Xaa can be any nonnatural amino acid listed in
      Table 1
<220> FEATURE:
<221> NAME/KEY: MISC_FEATURE
<222> LOCATION: (18)..(18)
<223> OTHER INFORMATION: Xaa is norleucine
```

```
<400> SEQUENCE: 5

His Xaa Asp Tyr Ala Xaa Ala Leu Ala Asn Pro Ile Lys His Val Ser
1               5                   10                  15

Leu Xaa Asp Gln Arg Ala Arg Gln Leu Ala Ala
            20                  25

<210> SEQ ID NO 6
<211> LENGTH: 27
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (18)..(18)
<223> OTHER INFORMATION: Xaa is norleucine
<220> FEATURE:
<221> NAME/KEY: MISC_FEATURE
<222> LOCATION: (21)..(21)
<223> OTHER INFORMATION: Xaa can be any nonnatural amino acid listed in
      Table 1
<220> FEATURE:
<221> NAME/KEY: MISC_FEATURE
<222> LOCATION: (25)..(25)
<223> OTHER INFORMATION: Xaa can be any nonnatural amino acid listed in
      Table 1

<400> SEQUENCE: 6

His Gln Asp Tyr Ala Glu Ala Leu Ala Asn Pro Ile Lys His Val Ser
1               5                   10                  15

Leu Xaa Asp Gln Xaa Ala Arg Gln Xaa Ala Ala
            20                  25

<210> SEQ ID NO 7
<211> LENGTH: 27
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (13)..(13)
<223> OTHER INFORMATION: Xaa can be any nonnatural amino acid listed in
      Table 1
<220> FEATURE:
<221> NAME/KEY: MISC_FEATURE
<222> LOCATION: (17)..(17)
<223> OTHER INFORMATION: Xaa can be any nonnatural amino acid listed in
      Table 1
<220> FEATURE:
<221> NAME/KEY: MISC_FEATURE
<222> LOCATION: (18)..(18)
<223> OTHER INFORMATION: Xaa is norleucine

<400> SEQUENCE: 7

His Gln Asp Tyr Ala Glu Ala Leu Ala Asn Pro Ile Xaa His Val Ser
1               5                   10                  15

Xaa Xaa Asp Gln Arg Ala Arg Gln Leu Ala Ala
            20                  25

<210> SEQ ID NO 8
<211> LENGTH: 27
<212> TYPE: PRT
<213> ORGANISM: Artificial
<220> FEATURE:
<223> OTHER INFORMATION: G-alpha-Q signaling downregulating peptide
      sequence
```

```
<220> FEATURE:
<221> NAME/KEY: MISC_FEATURE
<222> LOCATION: (17)..(17)
<223> OTHER INFORMATION: Xaa can be any nonnatural amino acid listed in
      Table 1
<220> FEATURE:
<221> NAME/KEY: MISC_FEATURE
<222> LOCATION: (18)..(18)
<223> OTHER INFORMATION: Xaa is norleucine
<220> FEATURE:
<221> NAME/KEY: MISC_FEATURE
<222> LOCATION: (21)..(21)
<223> OTHER INFORMATION: Xaa can be any nonnatural amino acid listed in
      Table 1

<400> SEQUENCE: 8

His Gln Asp Tyr Ala Glu Ala Leu Ala Asn Pro Ile Lys His Val Ser
1               5                   10                  15

Xaa Xaa Asp Gln Xaa Ala Arg Gln Leu Ala Ala
            20                  25

<210> SEQ ID NO 9
<211> LENGTH: 27
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (13)..(13)
<223> OTHER INFORMATION: Xaa can be any nonnatural amino acid listed in
      Table 1
<220> FEATURE:
<221> NAME/KEY: MISC_FEATURE
<222> LOCATION: (18)..(18)
<223> OTHER INFORMATION: Xaa is norleucine
<220> FEATURE:
<221> NAME/KEY: MISC_FEATURE
<222> LOCATION: (20)..(20)
<223> OTHER INFORMATION: Xaa can be any nonnatural amino acid listed in
      Table 1

<400> SEQUENCE: 9

His Gln Asp Tyr Ala Glu Ala Leu Ala Asn Pro Ile Xaa His Val Ser
1               5                   10                  15

Leu Xaa Asp Xaa Arg Ala Arg Gln Leu Ala Ala
            20                  25

<210> SEQ ID NO 10
<211> LENGTH: 27
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (3)..(3)
<223> OTHER INFORMATION: Xaa can be any nonnatural amino acid listed in
      Table 1
<220> FEATURE:
<221> NAME/KEY: MISC_FEATURE
<222> LOCATION: (17)..(17)
<223> OTHER INFORMATION: Xaa can be any nonnatural amino acid listed in
      Table 1
<220> FEATURE:
<221> NAME/KEY: MISC_FEATURE
<222> LOCATION: (18)..(18)
<223> OTHER INFORMATION: Xaa is norleucine
```

```
<400> SEQUENCE: 10

His Gln Xaa Tyr Ala Glu Ala Leu Ala Asn Pro Ile Lys His Val Ser
1               5                   10                  15

Xaa Xaa Asp Gln Arg Ala Arg Gln Leu Ala Ala
            20                  25

<210> SEQ ID NO 11
<211> LENGTH: 26
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (6)..(6)
<223> OTHER INFORMATION: Xaa can be any nonnatural amino acid listed in
      Table 1
<220> FEATURE:
<221> NAME/KEY: MISC_FEATURE
<222> LOCATION: (13)..(13)
<223> OTHER INFORMATION: Xaa can be any nonnatural amino acid listed in
      Table 1
<220> FEATURE:
<221> NAME/KEY: MISC_FEATURE
<222> LOCATION: (18)..(18)
<223> OTHER INFORMATION: Xaa is norleucine

<400> SEQUENCE: 11

His Gln Asp Tyr Ala Xaa Ala Leu Ala Asn Pro Ile Xaa His Val Ser
1               5                   10                  15

Leu Xaa Asp Gln Arg Ala Arg Gln Leu Ala
            20                  25

<210> SEQ ID NO 12
<211> LENGTH: 27
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (3)..(3)
<223> OTHER INFORMATION: Xaa can be any nonnatural amino acid listed in
      Table 1
<220> FEATURE:
<221> NAME/KEY: MISC_FEATURE
<222> LOCATION: (18)..(18)
<223> OTHER INFORMATION: Xaa is norleucine
<220> FEATURE:
<221> NAME/KEY: MISC_FEATURE
<222> LOCATION: (21)..(21)
<223> OTHER INFORMATION: Xaa can be any nonnatural amino acid listed in
      Table 1

<400> SEQUENCE: 12

His Gln Xaa Tyr Ala Glu Ala Leu Ala Asn Pro Ile Lys His Val Ser
1               5                   10                  15

Leu Xaa Asp Gln Xaa Ala Arg Gln Leu Ala Ala
            20                  25

<210> SEQ ID NO 13
<211> LENGTH: 27
<212> TYPE: PRT
<213> ORGANISM: Artificial
<220> FEATURE:
<223> OTHER INFORMATION: G-alpha-Q signaling downregulating peptide
      sequence
```

-continued

```
<220> FEATURE:
<221> NAME/KEY: MISC_FEATURE
<222> LOCATION: (6)..(6)
<223> OTHER INFORMATION: Xaa can be any nonnatural amino acid listed in
      Table 1
<220> FEATURE:
<221> NAME/KEY: MISC_FEATURE
<222> LOCATION: (18)..(18)
<223> OTHER INFORMATION: Xaa is norleucine
<220> FEATURE:
<221> NAME/KEY: MISC_FEATURE
<222> LOCATION: (21)..(21)
<223> OTHER INFORMATION: Xaa can be any nonnatural amino acid listed in
      Table 1

<400> SEQUENCE: 13

His Gln Asp Tyr Ala Xaa Ala Leu Ala Asn Pro Ile Lys His Val Ser
1               5                   10                  15

Leu Xaa Asp Gln Xaa Ala Arg Gln Leu Ala Ala
            20                  25

<210> SEQ ID NO 14
<211> LENGTH: 27
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (3)..(3)
<223> OTHER INFORMATION: Xaa can be any nonnatural amino acid listed in
      Table 1
<220> FEATURE:
<221> NAME/KEY: MISC_FEATURE
<222> LOCATION: (13)..(13)
<223> OTHER INFORMATION: Xaa can be any nonnatural amino acid listed in
      Table 1
<220> FEATURE:
<221> NAME/KEY: MISC_FEATURE
<222> LOCATION: (18)..(18)
<223> OTHER INFORMATION: Xaa is norleucine

<400> SEQUENCE: 14

His Gln Xaa Tyr Ala Glu Ala Leu Ala Asn Pro Ile Xaa His Val Ser
1               5                   10                  15

Leu Xaa Asp Gln Arg Ala Arg Gln Leu Ala Ala
            20                  25

<210> SEQ ID NO 15
<211> LENGTH: 27
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (6)..(6)
<223> OTHER INFORMATION: Xaa can be any nonnatural amino acid listed in
      Table 1
<220> FEATURE:
<221> NAME/KEY: MISC_FEATURE
<222> LOCATION: (17)..(17)
<223> OTHER INFORMATION: Xaa can be any nonnatural amino acid listed in
      Table 1
<220> FEATURE:
<221> NAME/KEY: MISC_FEATURE
<222> LOCATION: (18)..(18)
<223> OTHER INFORMATION: Xaa is norleucine
```

-continued

<400> SEQUENCE: 15

His Gln Asp Tyr Ala Xaa Ala Leu Ala Asn Pro Ile Lys His Val Ser
1               5                   10                  15

Xaa Xaa Asp Gln Arg Ala Arg Gln Leu Ala Ala
            20                  25

<210> SEQ ID NO 16
<211> LENGTH: 5
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (4)..(4)
<223> OTHER INFORMATION: Xaa can be any nonnatural amino acid, for
      example, as listed in Table 1

<400> SEQUENCE: 16

Tyr Ile Pro Xaa Asp
1               5

<210> SEQ ID NO 17
<211> LENGTH: 32
<212> TYPE: PRT
<213> ORGANISM: Artificial
<220> FEATURE:
<223> OTHER INFORMATION: G-alpha-Q signaling downregulating peptide
      sequence
<220> FEATURE:
<221> NAME/KEY: MISC_FEATURE
<222> LOCATION: (4)..(4)
<223> OTHER INFORMATION: Xaa can be any nonnatural amino acid listed in
      Table 1
<220> FEATURE:
<221> NAME/KEY: MISC_FEATURE
<222> LOCATION: (11)..(11)
<223> OTHER INFORMATION: Xaa can be any nonnatural amino acid listed in
      Table 1

<400> SEQUENCE: 17

Tyr Ile Pro Xaa Asp His Gln Asp Tyr Ala Xaa Ala Leu Ala Asn Pro
1               5                   10                  15

Ile Lys His Val Ser Leu Met Asp Gln Arg Ala Arg Ala Leu Ala Ala
            20                  25                  30

<210> SEQ ID NO 18
<211> LENGTH: 12
<212> TYPE: PRT
<213> ORGANISM: Artificial
<220> FEATURE:
<223> OTHER INFORMATION: Protein transduction domain sequence

<400> SEQUENCE: 18

Gly Arg Lys Lys Arg Arg Gln Arg Arg Pro Pro Gln
1               5                   10

<210> SEQ ID NO 19
<211> LENGTH: 16
<212> TYPE: PRT
<213> ORGANISM: Artificial
<220> FEATURE:
<223> OTHER INFORMATION: Protein transduction domain sequence

<400> SEQUENCE: 19

Arg Gln Ile Lys Ile Trp Phe Gln Asn Arg Arg Met Lys Trp Lys Lys
1               5                   10                  15

```
<210> SEQ ID NO 20
<211> LENGTH: 6
<212> TYPE: PRT
<213> ORGANISM: Artificial
<220> FEATURE:
<223> OTHER INFORMATION: Protein transduction domain sequence

<400> SEQUENCE: 20

Pro Phe Val Tyr Leu Ile
1               5

<210> SEQ ID NO 21
<211> LENGTH: 27
<212> TYPE: PRT
<213> ORGANISM: Artificial
<220> FEATURE:
<223> OTHER INFORMATION: Protein transduction domain sequence

<400> SEQUENCE: 21

Gly Trp Thr Leu Asn Ser Ala Gly Gly Tyr Leu Leu Gly Lys Ile Asn
1               5                   10                  15

Leu Lys Ala Leu Ala Ala Leu Ala Lys Lys Ile
            20                  25

<210> SEQ ID NO 22
<211> LENGTH: 9
<212> TYPE: PRT
<213> ORGANISM: Artificial
<220> FEATURE:
<223> OTHER INFORMATION: Protein transduction domain sequence

<400> SEQUENCE: 22

Arg Arg Arg Arg Arg Arg Arg Arg Arg
1               5

<210> SEQ ID NO 23
<211> LENGTH: 7
<212> TYPE: PRT
<213> ORGANISM: Artificial
<220> FEATURE:
<223> OTHER INFORMATION: Protein transduction domain sequence

<400> SEQUENCE: 23

Arg Arg Arg Arg Arg Arg Arg
1               5

<210> SEQ ID NO 24
<211> LENGTH: 21
<212> TYPE: PRT
<213> ORGANISM: Artificial
<220> FEATURE:
<223> OTHER INFORMATION: Protein transduction domain sequence

<400> SEQUENCE: 24

Lys Glu Thr Trp Trp Glu Thr Trp Trp Thr Trp Trp Ser Gln Pro Lys
1               5                   10                  15

Lys Lys Arg Lys Val
            20

<210> SEQ ID NO 25
<211> LENGTH: 11
<212> TYPE: PRT
<213> ORGANISM: Artificial
<220> FEATURE:
<223> OTHER INFORMATION: Protein transduction domain sequence
```

```
<400> SEQUENCE: 25

Tyr Gly Arg Lys Lys Arg Arg Gln Arg Arg Arg
1               5                   10

<210> SEQ ID NO 26
<211> LENGTH: 11
<212> TYPE: PRT
<213> ORGANISM: Artificial
<220> FEATURE:
<223> OTHER INFORMATION: Protein transduction domain sequence

<400> SEQUENCE: 26

Tyr Ala Arg Ala Ala Ala Arg Gln Ala Arg Ala
1               5                   10

<210> SEQ ID NO 27
<211> LENGTH: 13
<212> TYPE: PRT
<213> ORGANISM: Artificial
<220> FEATURE:
<223> OTHER INFORMATION: Protein transduction domain sequence

<400> SEQUENCE: 27

Lys Glu Thr Trp Trp Glu Thr Trp Trp Thr Glu Trp Ser
1               5                   10

<210> SEQ ID NO 28
<211> LENGTH: 27
<212> TYPE: PRT
<213> ORGANISM: Artificial
<220> FEATURE:
<223> OTHER INFORMATION: Protein transduction domain sequence

<400> SEQUENCE: 28

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 29
<211> LENGTH: 34
<212> TYPE: PRT
<213> ORGANISM: Artificial
<220> FEATURE:
<223> OTHER INFORMATION: Protein transduction domain sequence

<400> SEQUENCE: 29

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 30
<211> LENGTH: 20
<212> TYPE: PRT
<213> ORGANISM: Artificial
<220> FEATURE:
<223> OTHER INFORMATION: Protein transduction domain sequence
```

```
<400> SEQUENCE: 30

Lys Met Thr Arg Ala Gln Arg Arg Ala Ala Arg Arg Asn Arg Arg
1               5                   10                  15

Trp Thr Ala Arg
            20

<210> SEQ ID NO 31
<211> LENGTH: 21
<212> TYPE: PRT
<213> ORGANISM: Artificial
<220> FEATURE:
<223> OTHER INFORMATION: Alphahelical transmembrane domain sequence

<400> SEQUENCE: 31

Ile Ile Ser Val Tyr Cys Val Thr Ser Ile Ile Leu Pro Val Phe Phe
1               5                   10                  15

Phe Val Ala Ser Phe
            20

<210> SEQ ID NO 32
<211> LENGTH: 28
<212> TYPE: PRT
<213> ORGANISM: Artificial
<220> FEATURE:
<223> OTHER INFORMATION: Alphahelical transmembrane domain sequence

<400> SEQUENCE: 32

Phe Val Ile Tyr Met Phe Val Val His Phe Thr Ile Pro Met Ile Ile
1               5                   10                  15

Ile Phe Phe Cys Tyr Gly Gln Leu Val Phe Thr Val
            20                  25

<210> SEQ ID NO 33
<211> LENGTH: 24
<212> TYPE: PRT
<213> ORGANISM: Artificial
<220> FEATURE:
<223> OTHER INFORMATION: Alphahelical transmembrane domain sequence

<400> SEQUENCE: 33

Gln Ala Tyr Ala Ile Ala Ser Ser Ile Val Ser Phe Tyr Val Pro Leu
1               5                   10                  15

Val Ile Met Val Phe Val Tyr Ser
            20

<210> SEQ ID NO 34
<211> LENGTH: 27
<212> TYPE: PRT
<213> ORGANISM: Artificial
<220> FEATURE:
<223> OTHER INFORMATION: G-alpha-q activity increasing peptide sequence
<220> FEATURE:
<221> NAME/KEY: MISC_FEATURE
<222> LOCATION: (18)..(18)
<223> OTHER INFORMATION: Xaa is norleucine

<400> SEQUENCE: 34

His Gln Asp Tyr Ala Glu Ala Leu Ala Asn Pro Ile Lys His Val Ser
1               5                   10                  15

Leu Xaa Asp Gln Arg Ala Arg Gln Leu Ala Ala
            20                  25
```

```
<210> SEQ ID NO 35
<211> LENGTH: 27
<212> TYPE: PRT
<213> ORGANISM: Artificial
<220> FEATURE:
<223> OTHER INFORMATION: G-alpha-Q signalling downregulating peptide
      sequence

<400> SEQUENCE: 35

His Gln Asp Tyr Ala Glu Ala Leu Ala Asn Pro Ile Lys His Val Ser
1               5                   10                  15

Leu Met Asp Gln Arg Ala Arg Gln Leu Ala Ala
            20                  25

<210> SEQ ID NO 36
<211> LENGTH: 4
<212> TYPE: PRT
<213> ORGANISM: Artificial
<220> FEATURE:
<223> OTHER INFORMATION: CaaX box sequence

<400> SEQUENCE: 36

Cys Ala Ile Leu
1

<210> SEQ ID NO 37
<211> LENGTH: 27
<212> TYPE: PRT
<213> ORGANISM: Artificial
<220> FEATURE:
<223> OTHER INFORMATION: PLC-beta-3 peptide sequence

<400> SEQUENCE: 37

His Gln Asp Tyr Ala Glu Ala Leu Ile Asn Pro Ile Lys His Val Ser
1               5                   10                  15

Leu Met Asp Gln Arg Ala Arg Gln Leu Ala Ala
            20                  25

<210> SEQ ID NO 38
<211> LENGTH: 25
<212> TYPE: PRT
<213> ORGANISM: Artificial
<220> FEATURE:
<223> OTHER INFORMATION: PLC-beta-3 peptide sequence

<400> SEQUENCE: 38

His Gln Asp Tyr Ala Glu Ala Leu Ile Asn Pro Ile Lys His Val Ser
1               5                   10                  15

Leu Met Asp Gln Arg Ala Arg Gln Leu
            20                  25

<210> SEQ ID NO 39
<211> LENGTH: 13
<212> TYPE: PRT
<213> ORGANISM: Artificial
<220> FEATURE:
<223> OTHER INFORMATION: PLC-beta-3 peptide sequence

<400> SEQUENCE: 39

His Gln Asp Tyr Ala Glu Ala Leu Ile Asn Pro Ile Lys
1               5                   10

<210> SEQ ID NO 40
<211> LENGTH: 10
<212> TYPE: PRT
<213> ORGANISM: Artificial
```

```
<220> FEATURE:
<223> OTHER INFORMATION: PLC-beta-3 peptide sequence

<400> SEQUENCE: 40

His Gln Asp Tyr Ala Glu Ala Leu Ile Asn
1               5                   10

<210> SEQ ID NO 41
<211> LENGTH: 25
<212> TYPE: PRT
<213> ORGANISM: Artificial
<220> FEATURE:
<223> OTHER INFORMATION: p63RhoGEF peptide sequence

<400> SEQUENCE: 41

Gln Arg Asp Phe Leu Asn Ala Leu Gln Ser Pro Ile Glu Tyr Gln Arg
1               5                   10                  15

Arg Glu Ser Gln Thr Asn Ser Leu Gly
            20                  25
```